(12) United States Patent
Borody

(10) Patent No.: US 11,166,990 B2
(45) Date of Patent: Nov. 9, 2021

(54) METHODS AND COMPOSITIONS FOR TREATING ULCERATIVE COLITIS

(71) Applicant: Finch Therapeutics Holdings LLC, Somerville, MA (US)

(72) Inventor: Thomas Julius Borody, Five Dock (AU)

(73) Assignee: Finch Therapeutics Holdings LLC, Somerville, MA (US)

( * ) Notice: Subject to any disclaimer, the term of this patent is extended or adjusted under 35 U.S.C. 154(b) by 0 days.

(21) Appl. No.: 16/510,579

(22) Filed: Jul. 12, 2019

(65) Prior Publication Data

US 2020/0016218 A1   Jan. 16, 2020

Related U.S. Application Data

(60) Provisional application No. 62/697,796, filed on Jul. 13, 2018, provisional application No. 62/697,810, filed on Jul. 13, 2018.

(51) Int. Cl.
| | |
|---|---|
| *A61K 35/742* | (2015.01) |
| *A61K 9/08* | (2006.01) |
| *A61K 9/19* | (2006.01) |
| *A61K 9/16* | (2006.01) |

(52) U.S. Cl.
CPC ............ *A61K 35/742* (2013.01); *A61K 9/08* (2013.01); *A61K 9/16* (2013.01); *A61K 9/19* (2013.01)

(58) Field of Classification Search
CPC combination set(s) only.
See application file for complete search history.

(56) References Cited

U.S. PATENT DOCUMENTS

| | | |
|---|---|---|
| 3,192,116 A | 6/1965 | Mose et al. |
| 3,320,130 A | 5/1967 | Henry |
| 3,713,836 A | 1/1973 | Carlsson |
| 4,098,728 A | 7/1978 | Rosenblatt |
| 4,309,782 A | 1/1982 | Paulin |
| 4,332,790 A | 6/1982 | Sozzi et al. |
| 4,335,107 A | 6/1982 | Snoeyenbos et al. |
| 4,452,779 A | 6/1984 | Cockerill |
| 4,536,409 A | 8/1985 | Farrell et al. |
| 4,657,762 A | 4/1987 | Mikkola et al. |
| 4,710,379 A | 12/1987 | Kawai et al. |
| 4,892,731 A | 1/1990 | Arai et al. |
| 4,975,286 A | 12/1990 | Hechter |
| 5,213,807 A | 5/1993 | Chemburkar et al. |
| 5,266,315 A | 11/1993 | Taguchi et al. |
| 5,443,826 A | 8/1995 | Borody |
| 5,728,380 A | 3/1998 | Allen et al. |
| 5,800,821 A | 9/1998 | Acheson et al. |
| 5,837,238 A | 11/1998 | Casas et al. |
| 5,858,356 A | 1/1999 | Wolf et al. |
| 5,902,578 A | 5/1999 | Halpin-Dohnalek et al. |
| 5,902,743 A | 5/1999 | Luchansky et al. |
| 6,087,386 A | 7/2000 | Chen et al. |
| 6,162,464 A | 12/2000 | Jacob et al. |
| 6,245,740 B1 | 6/2001 | Goldenberg et al. |
| 6,284,274 B1 | 9/2001 | Merrill et al. |
| 6,428,783 B1 | 8/2002 | Khachatrian et al. |
| 6,479,051 B1 | 11/2002 | Bruce |
| 6,514,531 B1 | 2/2003 | Alaux et al. |
| 6,645,530 B1 | 11/2003 | Borody |
| 6,649,397 B1 | 11/2003 | Nakamura |
| 6,756,032 B1 | 6/2004 | Tepper et al. |
| 6,926,907 B2 | 8/2005 | Plachetka |
| 6,979,674 B1 | 12/2005 | Goldenberg et al. |
| 6,984,513 B2 | 1/2006 | Brown et al. |
| 7,018,629 B2 | 3/2006 | Jacob et al. |
| 7,374,753 B1 | 5/2008 | Farmer et al. |
| 7,541,091 B2 | 6/2009 | Sisson et al. |
| 7,749,509 B2 | 7/2010 | Cobb et al. |
| 7,763,276 B1 | 7/2010 | Shodai et al. |
| 7,799,341 B2 | 9/2010 | Porzio et al. |
| 7,815,956 B2 | 10/2010 | Lee et al. |
| 7,846,475 B2 | 12/2010 | Shiraishi et al. |
| 7,888,062 B1 | 2/2011 | Garner et al. |
| 7,998,510 B2 | 8/2011 | Caswell |
| 8,168,171 B2 | 5/2012 | Mogna et al. |
| 8,460,648 B2 | 6/2013 | Borody |

(Continued)

FOREIGN PATENT DOCUMENTS

| | | |
|---|---|---|
| AU | 2001276160 B2 | 6/2007 |
| CA | 1333564 | 12/1994 |

(Continued)

OTHER PUBLICATIONS

"Autoimmune Disease List," *American Autoimmune Related Diseases Association*, pp. 1-4 (2017) <https://www.aarda.org/diseaselist/>.

"Certain infectious and parasitic diseases (A00-B99)," *International Statistical Classification of Diseases and Related Health Problems, 10th Revision (ICD-10)—WHO Version*, Chapter 1, pp. 1 (2016) <www.apps.who.int/classifications/icd 0/browse/2016/en#II>.

"Spore-Forming Gram-Positive Bacilli: *Bacillus* and *Clostridium* Species," *Jawetz, Melnick, & Adelberg's Medical Microbiology*, 26th Edition, Chapter 11, pp. 1-15 (2012).

(Continued)

*Primary Examiner* — Heidi Reese
(74) *Attorney, Agent, or Firm* — Arnold & Porter Kaye Scholer LLP; David Marsh; Scott Douglas

(57) ABSTRACT

The present disclosure provides methods and pharmaceutical compositions for treating ulcerative colitis (UC) in a subject in need thereof. In particular, the compositions described here comprise or are designed based on fecal bacteria associated with FMT-based UC treatment success or failure. Also provided are methods for screening patients for their suitability for a fecal bacteria-based UC treatment. Further provided are methods for screening fecal donors for optimized source materials for producing a fecal bacteria-based pharmaceutical composition.

20 Claims, No Drawings

(56) References Cited

U.S. PATENT DOCUMENTS

| | | |
|---|---|---|
| 8,586,029 B2 | 11/2013 | Kasper et al. |
| 8,637,297 B2 | 1/2014 | Fernandez et al. |
| 8,658,153 B2 | 2/2014 | Daube et al. |
| 8,771,673 B2 | 7/2014 | Cobb et al. |
| 9,040,036 B2 | 5/2015 | Borody |
| 9,050,358 B2 | 6/2015 | Borody |
| 9,308,226 B2 | 4/2016 | Borody |
| 9,320,763 B2 | 4/2016 | Borody |
| 9,408,872 B2 | 8/2016 | Borody |
| 9,468,658 B2 | 10/2016 | Borody |
| 9,572,841 B2 | 2/2017 | Borody |
| 9,572,842 B2 | 2/2017 | Borody |
| 9,610,308 B2 | 4/2017 | Borody |
| 9,623,056 B2 | 4/2017 | Borody |
| 9,719,144 B2 | 8/2017 | Krajmalnik-Brown et al. |
| 2001/0014322 A1 | 8/2001 | Chen et al. |
| 2002/0013270 A1 | 1/2002 | Bolte |
| 2002/0022019 A1 | 2/2002 | Laulund |
| 2002/0039599 A1 | 4/2002 | Lin et al. |
| 2003/0092163 A1 | 5/2003 | Collins et al. |
| 2003/0092724 A1 | 5/2003 | Kao et al. |
| 2003/0147858 A1 | 8/2003 | Renaud et al. |
| 2004/0062757 A1 | 4/2004 | Finegold |
| 2004/0167062 A1 | 8/2004 | Bolte |
| 2004/0170617 A1 | 9/2004 | Finegold |
| 2004/0223956 A1 | 11/2004 | Naidu et al. |
| 2006/0076536 A1 | 4/2006 | Barshied |
| 2006/0099197 A1 | 5/2006 | Farmer |
| 2006/0115465 A1 | 6/2006 | Macfarlane et al. |
| 2006/0177424 A1 | 8/2006 | Cobb et al. |
| 2006/0275223 A1 | 12/2006 | Burr |
| 2007/0059296 A1 | 3/2007 | Chen |
| 2008/0254009 A1 | 10/2008 | Finegold |
| 2008/0299197 A1 | 12/2008 | Toneguzzo et al. |
| 2010/0112003 A1 | 5/2010 | Collins et al. |
| 2010/0178349 A1 | 7/2010 | Kolter et al. |
| 2010/0178413 A1 | 7/2010 | Gorris |
| 2010/0184785 A1 | 7/2010 | Kolter et al. |
| 2010/0222311 A1 | 9/2010 | Thommes et al. |
| 2010/0226866 A1 | 9/2010 | Yamashiro et al. |
| 2010/0233278 A1 | 9/2010 | Ookawa et al. |
| 2010/0239667 A1 | 9/2010 | Hemmingsen et al. |
| 2010/0247489 A1 | 9/2010 | Saur-Brosch et al. |
| 2010/0247665 A1 | 9/2010 | Takahashi |
| 2010/0255231 A1 | 10/2010 | Chau et al. |
| 2010/0255307 A1 | 10/2010 | Gonze et al. |
| 2010/0278930 A1 | 11/2010 | Okumura et al. |
| 2010/0285164 A1 | 11/2010 | Schaible et al. |
| 2010/0289164 A1 | 11/2010 | Porzio et al. |
| 2010/0297031 A1 | 11/2010 | Ubeda Perez et al. |
| 2011/0008554 A1 | 1/2011 | Chen et al. |
| 2011/0045222 A1 | 2/2011 | Peters |
| 2011/0081320 A1 | 4/2011 | Westall et al. |
| 2011/0200570 A1 | 8/2011 | Mosbaugh et al. |
| 2011/0218216 A1 | 9/2011 | Vivek et al. |
| 2012/0020941 A1 | 1/2012 | Wacklin et al. |
| 2012/0039853 A1 | 2/2012 | Corveleyn et al. |
| 2012/0064133 A1 | 3/2012 | Chauhan et al. |
| 2012/0087895 A1 | 4/2012 | Mazmanian et al. |
| 2012/0183612 A1 | 7/2012 | Brogmann et al. |
| 2012/0252775 A1 | 10/2012 | Finegold |
| 2013/0045274 A1 | 2/2013 | Hlavka |
| 2013/0195804 A1 | 8/2013 | Borody |
| 2013/0259899 A1 | 10/2013 | Allen-Vercoe et al. |
| 2013/0316394 A1 | 11/2013 | Stimpson |
| 2014/0065132 A1 | 3/2014 | Hsiao et al. |
| 2014/0086877 A1 | 3/2014 | Hlavka |
| 2014/0147417 A1 | 5/2014 | Sadowsky et al. |
| 2014/0147425 A1 | 5/2014 | Henn et al. |
| 2014/0234260 A1 | 8/2014 | Borody |
| 2014/0255351 A1 | 9/2014 | Berstad et al. |
| 2014/0328803 A1 | 11/2014 | McKenzie et al. |
| 2014/0341921 A1 | 11/2014 | Honda et al. |
| 2014/0342438 A1 | 11/2014 | Allen-Vercoe et al. |
| 2014/0363397 A1 | 12/2014 | Allen-Vercoe et al. |
| 2014/0363398 A1 | 12/2014 | Jones et al. |
| 2015/0044173 A1 | 2/2015 | Jones et al. |
| 2015/0050246 A1 | 2/2015 | Jones et al. |
| 2015/0093360 A1 | 4/2015 | McKenzie et al. |
| 2015/0143557 A1 | 5/2015 | Honda et al. |
| 2015/0152484 A1 | 6/2015 | Krajmalnik-Brown et al. |
| 2015/0190435 A1 | 7/2015 | Henn et al. |
| 2015/0224152 A1 | 8/2015 | Littman et al. |
| 2015/0238544 A1 | 8/2015 | Jones et al. |
| 2015/0238545 A1 | 8/2015 | Borody |
| 2015/0238546 A1 | 8/2015 | Borody |
| 2015/0297642 A1 | 10/2015 | Borody |
| 2015/0306144 A1 | 10/2015 | Borody |
| 2015/0306155 A1 | 10/2015 | Borody |
| 2015/0306156 A1 | 10/2015 | Borody |
| 2015/0374761 A1 | 12/2015 | Sadowsky et al. |
| 2016/0089363 A1 | 3/2016 | Borody |
| 2016/0151429 A1 | 6/2016 | Borody |
| 2016/0151431 A1 | 6/2016 | Borody |
| 2016/0151432 A1 | 6/2016 | Borody |
| 2016/0151433 A1 | 6/2016 | Borody |
| 2016/0158294 A1 | 6/2016 | Von Maltzahn et al. |
| 2016/0279178 A1 | 9/2016 | Borody |
| 2016/0279179 A1 | 9/2016 | Borody |
| 2016/0339065 A1 | 11/2016 | Adams et al. |
| 2017/0216378 A1 | 8/2017 | Honda et al. |
| 2017/0246220 A1 | 8/2017 | Sato et al. |
| 2017/0348360 A1 | 12/2017 | Borody |
| 2018/0153943 A1 | 6/2018 | Borody |
| 2018/0256652 A1 | 9/2018 | Borody |
| 2019/0015460 A1 | 1/2019 | Borody |
| 2019/0015461 A1 | 1/2019 | Borody |
| 2019/0015462 A1 | 1/2019 | Borody |
| 2019/0046589 A1 | 2/2019 | Borody |

FOREIGN PATENT DOCUMENTS

| | | |
|---|---|---|
| CA | 2 391 422 A1 | 1/2004 |
| CN | 1561387 A | 1/2005 |
| CN | 101496819 A | 8/2009 |
| CN | 201441672 U | 4/2010 |
| DE | 2 134 179 A1 | 1/1973 |
| EP | 0 303 426 A2 | 2/1989 |
| EP | 0 456 418 A2 | 11/1991 |
| EP | 0 433 299 B1 | 5/1998 |
| EP | 1 514 572 A2 | 3/2005 |
| EP | 1 514 572 A3 | 11/2006 |
| EP | 1 800 688 A1 | 6/2007 |
| EP | 1 514 572 B1 | 12/2008 |
| EP | 2 823 822 B1 | 10/2016 |
| FR | 1275 M | 5/1962 |
| FR | 2427 M | 3/1964 |
| FR | 2828 M | 10/1964 |
| FR | 5528 M | 11/1967 |
| FR | 2 244 464 A1 | 4/1975 |
| GB | 1271674 A | 4/1972 |
| JP | 64-67192 | 3/1989 |
| JP | H05-306221 A | 11/1993 |
| JP | H07-242539 A | 9/1995 |
| JP | H07-242557 A | 9/1995 |
| JP | 3 144 556 B2 | 3/2001 |
| JP | 2004-501095 | 1/2004 |
| JP | 2005-118544 A | 5/2005 |
| JP | 2008-106066 | 5/2008 |
| JP | 2010-513359 | 4/2010 |
| JP | 2010-520234 A | 6/2010 |
| KR | 10-0913405 B1 | 8/2009 |
| WO | WO 90/01335 A1 | 2/1990 |
| WO | WO 95/33046 A1 | 12/1995 |
| WO | WO 96/11014 A1 | 4/1996 |
| WO | WO 98/13068 A1 | 4/1998 |
| WO | WO 00/07571 A2 | 2/2000 |
| WO | WO 00/015760 | 3/2000 |
| WO | WO 00/42168 A2 | 7/2000 |
| WO | WO 02/07741 A1 | 1/2002 |
| WO | WO 03/033681 A2 | 4/2003 |
| WO | WO 2005/017095 A2 | 2/2005 |
| WO | WO 2006/127355 A2 | 11/2006 |
| WO | WO 2008/077614 A2 | 7/2008 |

(56) References Cited

FOREIGN PATENT DOCUMENTS

| | | |
|---|---|---|
| WO | WO 2008/105715 A2 | 9/2008 |
| WO | WO 2008/117266 A2 | 10/2008 |
| WO | WO 2008/117267 A2 | 10/2008 |
| WO | WO 2008/077614 A3 | 1/2009 |
| WO | WO 2009/024429 A2 | 2/2009 |
| WO | WO 2009/026306 A2 | 2/2009 |
| WO | WO 2009/055362 A1 | 4/2009 |
| WO | WO 2010/040020 A1 | 4/2010 |
| WO | WO 2011/033310 A1 | 3/2011 |
| WO | WO 2011/094027 A1 | 8/2011 |
| WO | WO 2011/110347 A2 | 9/2011 |
| WO | WO 2011/151941 A1 | 12/2011 |
| WO | WO 2012/013861 A2 | 2/2012 |
| WO | WO 2012/016287 A2 | 2/2012 |
| WO | WO 2012/045150 A1 | 4/2012 |
| WO | WO 2012/122478 A1 | 9/2012 |
| WO | WO 2012/016287 A3 | 11/2012 |
| WO | WO 2013/037067 A1 | 3/2013 |
| WO | WO 2013/090825 A1 | 6/2013 |
| WO | WO 2014/070014 A1 | 5/2014 |
| WO | WO 2014/078911 A1 | 5/2014 |
| WO | WO 2014/152338 A1 | 9/2014 |
| WO | WO 2014/152484 A1 | 9/2014 |
| WO | WO 2015/006355 A2 | 1/2015 |
| WO | WO 2015/051323 A1 | 4/2015 |
| WO | WO 2015/077794 A1 | 5/2015 |
| WO | WO 2015/095241 A2 | 6/2015 |
| WO | WO 2015/124637 A1 | 8/2015 |
| WO | WO 2016/133450 A1 | 2/2016 |
| WO | WO 2016/183577 A1 | 11/2016 |
| WO | WO 2016/191356 A1 | 12/2016 |
| WO | WO 2017/075098 A1 | 5/2017 |
| WO | WO 2017/152137 A2 | 9/2017 |

OTHER PUBLICATIONS

"ARGF—'Autologous Rehabilitation of Gastrointestinal Flora,'" Medipex Report for Medilink NW, pp. 1-42, n.d., Web, Feb. 10, 2012 <http://www.bacteriotherapy.org/docs/medipex-report. pelf>.
"Frequently Asked Questions about Clostridium difficile for Healthcare Providers," Healthcare-associated Infections (HAis), Centers for Disease Control and Prevention, pp. 1-6, Nov. 25, 2010, updated Mar. 6, 2012, Web, May 19, 2014 <http://www.cdc.gov/HAI/organisms/cdiff/Cdiff faqs HCP.html>.
"Functional Anatomy of Prokaryotic and Eukaryotic Cells," printed Mar. 16, 2017 <http://classes.midlandstech.edu/carterp/courses/bio225/chap04/lecture2.htm>.
"Monilia," Def. 1, Stedman's Medical Dictionary, n.d., Web, Nov. 22, 2005.
"Probiotic," Def. 1, MSN Encarta—Dictionary, Encarta, n.d., Web, Dec. 1, 2005.
Aas et al., "Recurrent Clostridium difficile Colitis: Case Series Involving 18 Patients Treated with Donor Stool Administered via a Nasogastric Tube," *Clinical Infectious Diseases*, 36(5):580-585 (2003).
Abrams, "Open-Label, Uncontrolled Trial of Bowel Sterilization and Repopulation with Normal Bowel Flora for Treatment of Inflammatory Bowel Disease," *Current Therapeutic Research*, 58(12):1001-1012 (1997).
Acha et al., "Changes of viability and composition of the *Escherichia coli* flora in faecal samples during long time storage," Journal of Microbiological Methods, Elsevier, 63(3):229-238 (2005).
Agrawal et al., "'Global warming' to *Mycobacterium avium* subspecies paratuberculosis," *Future Microbial*, 9(7):829-832 (2014).
Agrawal et al., "A Long-Term Follow-Up Study of the Efficacy and Safety of Fecal Microbiota Transplant (FMT) for Recurrent/Severe/Complicated *C. difficile* Infection (CDI) in the Elderly," *Gastroenterol*, 146(5)(Suppl 1):S42-43 (2014).
Aitken et al., "Demonstration of Intracellular *Mycobacterium* Species in Crohn's Disease Using Novel Technologies," Poster Presentation—2015 ACG Annual Scientific Meeting, Honolulu, Hawaii, USA (2015).
Akao et al., "A Purgative Action of Barbaloin Is Induced by *Eubacterium* sp. Strain BAR, a Human Intestinal Anaerobe, Capable of Transforming Barbaloin to Aloe-EmodinAnthrone," Biol. Pharm., 19(1):136-138 (1996).
Al-Eidan et al., "Clostridium difficile-associated diarrhoea in hospitalised patients," *J Clin. Pharm. Ther.*, 25(2):101-109 (2000).
Al-Nassir et al., "Comparison of Clinical and Microbiological Response to Treatment of Clostridium difficile-Associated Disease with Metronidazole and Vancomycin," *Clin Infect Dis.*, 47(1):56-62 (2008).
Anand et al., "Epidemiology, clinical manifestations, and outcome of Clostridium difficile-associated diarrhea," *Am J Gastroenterol.*, 89(4):519-23 (1994).
Ananthakrishnan et al., "Excess hospitalisation burden associated with Clostridium difficile in patients with inflammatory bowel disease," *Gut*, 57(2):205-210 (2007).
Anderson et al., "Systematic review: faecal microbiota transplantation in the management of inflammatory bowel disease," *Aliment. Pharmacol. Ther.*, 36:503-16 (2012).
Andoh et al., "Terminal restriction fragment polymorphisum analyses of fecal microbiota in five siblings including two with ulcerative colitis," *Journal of Clinical Gastroenterology*, 2:343-345 (2009).
Andrews et al., "'Putting back the bugs': Bacterial Treatment Relieves Chronic Constipation and Symptoms of Irritable Bowel Syndrome," *Med. J Aust.*, 159(9):633-634 (1993).
Andrews et al., "Bacteriotherapy for Chronic Constipation—A Long Term Follow-Up," *Gastroenterol*, 108:A563 Abstract (1995).
Andrews et al., "Chronic Constipation (CC) may be reversed by Bacteriotherapy," *Gastroenterol*, 106:A459 (1994).
Andrews et al., "Chronic constipation reversed by restoration of bowel flora. A case and a hypothesis," *European Journal of Gastroenterology & Hepatology*, 4:245-247 (1992).
Anorexia nervosa, Encyclopedia Index A, health AtoZ, Medical Network, Inc., pp. 1-7, n.d., Web, Nov. 23, 2005 <http://www.healthatoz.com/healthatoz/Atoz/ency/anorexia_nervosa.jsp>.
Arkkila et al., "Fecal Bacteriotherapy for Recurrent *Clostridium difficile* Infection," *Gastroenterology*, 138(5):SI-S5 (2010).
Aroniadis et al., "Intestinal Microbiota and the Efficacy of Fecal Microbiota Transplantation in Gastrointestinal Disease," *Gastroenterology and Hepatology*, 10(4): 230-7 (2014).
Aroniadis et al., "Long-Term Follow-up Study of Fecal Microbiota Transplantation (FMT) for Severe or Complicated *Clostridium difficile* Infection (CDI)," *Gastroenterol*, 144(Suppl 1):S185 (2013).
Atarashi et al., "Induction of Colonic Regulatory T Cells by Indigenous *Clostridium* Species," *Science*, 331(6015):337-341, published online Dec. 23, 2010.
Atarashi et al., "$T_{reg}$ induction by a rationally selected mixture of *Clostridia* strains from the human microbiota," *Nature*, 500(7461):232-236 (2013).
Atarashi et al., "WS/PP-064-03 Regulation of colonic regulatory T cells by *Clostridium* species," *International Immunology*, 22(Suppl 1, Part 3), pp. 1-3 (2010).
Atarashi et al., WS-064 Mucosal immunity: homeostasis, 14thICIC Abstractbook, 14th International Congress of immunology, pp. iii131-iii133 (2010).
Autism, Health Encyclopedia—Diseases and Conditions, The Health Scout Network, pp. 1-5, n.d., Web, Nov. 22, 2005 <www.healthscout.com>.
Autism, Treatment, Prognosis, Healthcommunities.com, Inc., pp. 1-4, n.d., Web. Jan. 28, 2009 <http://www.neurologychannel.com/common/PrintPage.php>.
Autism: Mayo Clinic.com, Mayo Foundation for Medical Education and Research, pp. 1-7, May 31, 2008, Web. Jan. 28, 2009 <http://www.mayoclinic.com/print/autism/DS00348/METHOD=print&DSECTION=all>.
Backhed et al., "Host-bacterial mutualism in the human intestine," *Science*, 307(5717):1915-1920 (2005).
Backhed et al., "Mechanisms underlying the resistance to diet-induced obesity in germ-free mice," *PNAS USA*, 104(3):979-984 (2007).
Backhed et al., "The gut microbiota as an environmental factor that regulates fat storage," *PNAS USA*, 101(44):15718-15723 (2004).

(56) References Cited

OTHER PUBLICATIONS

Bakken et al., "Fecal bacteriotherapy for recurrent Clostridium difficile infection," *Anaerobe*, 15(6):285-289 (2009).
Bakken et al., "Treating Clostridium difficile Infection with Fecal Microbiota Transplantation," *Clinical Gastroenterology and Hepatology*, 9(12):1044-1049 (2011).
Bartlett et al., "Clinical recognition and diagnosis of Clostridium difficile infection," *Clin Infect Dis.*, 46(Suppl 1):S12-S18 (2008).
Bartlett, "Clostridium difficile-associated Enteric Disease," *Curr Infect Dis Rep.*, 4(6):477-483 (2002).
Belkaid et al., "Natural regulatory T cells in infectious disease," *Nature Immunology*, 6(4):353-360 (2005).
Bengmark et al., "Bioecological control of inflammatory bowel disease," *Clinical Nutrition*, 26(2):169-181 (2007).
Bennet et al., "Treatment of ulcerative colitis by implantation of normal colonic flora," *Lancet*, 333(8630):164 (1989).
Benson et al., "Changing epidemiology of Clostridium difficile-associated disease in children," *Infect Control Hosp Epidemiol.*, 28(11):1233-1235 (2007).
Bergey's Manual of Systematic Bacteriology, Second Edition, vol. Three, The Firmicutes, pp. 1-16 (2009).
Blaser et al., "What are the consequences of the disappearing human microbiota?" *Nat. Rev. Microbial.*, 7(12):887-894 (2009).
Blaser, "Who are we? Indigenous microbes and the ecology of human diseases," *EMBO Rep*, 7(10):956-960 (2006).
Bolte, "Autism and Clostridium tetani," Medical Hypotheses, 51(2):133-144 (1998).
Bolte, Therapies for Gastrointestinal and Neurological Disorders, U.S. Appl. No. 60/214,813, filed Jun. 28, 2000.
Borody et al., "Fecal microbiota transplantation in gastrointestinal disease: 2015 update and the road ahead," Expert Review of Gastroenterology and Hepatology, 9(11):1379-1391 (2015).
Borody et al., "Anti-MAP Rescues Anti-TNF Failures for Over 4 Years," *Gastroenterol*, 136(5)Suppl 1:A-681 (2009).
Borody et al., "Anti-MAP Therapy for Pediatric Crohn's Disease," *Am J Gastroenterol*, 108 (Suppl 1):S516 (2013).
Borody et al., "Anti-MAP Therapy in the Treatment of Active Crohn's Disease," *J Gastroenterol & Hepatol*, 20(Suppl):A2 (2005).
Borody et al., "Anti-mycobacterial therapy in Crohn's disease heals mucosa with longitudinal scars," *Digestive & Liver Disease*, 39(5):438-444 (2007).
Borody et al., "Anti-*Mycobacterium avium* SS *Paratuberculosis* (MAP) Therapy and Fistula Closure in Patients with Severe Crohn's Disease," *Am J Gast, Al* 0J:S440 (2006).
Borody et al., "Bacteriotherapy in Chronic Fatigue Syndrome (CFS): A retrospective review," *AmJGastro*, 107(SJ):A1481 (2012).
Borody et al., "Bacteriotherapy Using Fecal Flora: toying with human motions" *J Clin. Gastroenterol.*, 38(6):475-483 (2004).
Borody et al., "Bowel-flora alteration: a potential cure for inflammatory bowel disease and irritable bowel syndrome?" *Med. J Aust.*, 150:604 (1989).
Borody et al., "Changes in Crohn's Disease Activity Index and C-Reactive Protein Levels During Anti-MAP Therapy," *AM J Gastro*, 104(S3):A1293 (2009).
Borody et al., "*Clostridium difficile* Complicating Inflammatory Bowel Disease: Pre-and Post-Treatment Findings," *Gastroenterol*, J 34(4)Suppl 1:A-361 (2008).
Borody et al., "Could fecal microbiota transplantation cure all Clostridium difficile infections?," *Future Microbial*, 9:1-3 (2014).
Borody et al., "*Entamoeba histolytica*: another cause of Crohn's Disease," *AM J Gastro*, 104(S3):A990 (2009).
Borody et al., "Faecal bacteriotherapy (FB) for chronic *C. difficile* (Cd) syndromes," *J Gastroenterol Hepatol*, 1 8(Suppl.):B8 (Abstract) (2003).
Borody et al., "Fecal bacteriotherapy in the treatment of recurrent C. difficile infection," *UpToDate*, pp. 1-6 (2006).
Borody et al., "Fecal Microbiota Transplantation (FMT) in Multiple Sclerosis (MS)," *AMJGastro*, 106(S2):A942 (2011).
Borody et al., "Fecal microbiota transplantation and emerging applications," *Nat. Rev. Gastroenterol. Hepatol.*, 9(2):88-96 (2011).

Borody et al., "Fecal microbiota transplantation for *Clostridium difficile* infection: A surgeon's perspective" *Seminars in Colon and Rectal Surgery*, 25:163-166 (2014).
Borody et al., "Fecal microbiota transplantation in gastrointestinal diseases—What practicing physicians should know," *Polish Archives of Internal Medicine*, 125(11):852-858 (2015).
Borody et al., "Fecal microbiota transplantation in the treatment of recurrent Clostridium difficile infection," *UpToDate*, pp. 1-4, (2015).
Borody et al., "Fecal Microbiota Transplantation in Ulcerative Colitis: Review of 24 Years Experience," *Am J Gastro*, 107(Supp 1):A1644 (2012).
Borody et al., "Fecal microbiota transplantation: a new standard treatment option for *Clostridium difficile* infection," *Expert Rev Anti Infect Ther.*, 11(5):447-449 (2013).
Borody et al., "Fecal microbiota transplantation: current status and future directions," *Expert Review of Gastroenterology & Hepatology*, 5(6):653-655 (2011).
Borody et al., "Fecal Microbiota Transplantation: Expanding Horizons for *Clostridium difficile* Infections and Beyond," *Antibiotics*, 4:254-266 (2015).
Borody et al., "Fecal Microbiota Transplantation: Indications, Methods, Evidence, and Future Directions," *Curr Gastroenterol Rep*, 15:337-344 (2013).
Borody et al., "Fecal Microbiota Transplantation: Techniques, Applications, and Issues," *Gastroenterol Clin North Am*, 41:781-803 (2012).
Borody et al., "Irritable Bowel Syndrome and *Dientamoeba fragilis*," *ASM Sydney National Conference*, pp. 4-5 (2002).
Borody et al., "Is Crohn's Disease Ready for Fecal Microbiota Transplantation?," *J Clin Gastroenterol*, 48(7):582-583 (2014).
Borody et al., "Myoclonus-dystonia affected by GI Microbiota?," *AM J Gastro*, 106(S2):A940 (2011).
Borody et al., "Novel appearance of healing mucosa following anti-*Mycobacterium avium paratuberculosis* therapy for Crohn's disease," *J Gastroenterol Hepatol*, 19(Suppl) :A210 (2004).
Borody et al., Reversal of Idiopathic Thrombocytopenic Purpura [ITP] with Fecal Microbiota Transplantation [FMT], *AM J Gastro*, 106(S2):A941 (2011).
Borody et al., "Reversal of Inflammatory Bowel Disease (IBD) with Recurrent Faecal Microbiota Transplants (FMT)," *AM J Gastro*, 106(S2):A979 (2011).
Borody et al., "Severe recurrent Crohn's Disease of ileocolonic anastomosis and antimicrobial (anti-mycobacterial therapy)," *Gut*, 55:1211 (2006).
Borody et al., "The GI Microbiome and its Role in Chronic Fatigue Syndrome: a Summary of Bacteriotherapy," ACNEM Journal, 31(3):3-8 (2012).
Borody et al., "Therapeutic faecal microbiota transplantation: current status and future developments," *Curr Opin Gastroenterol*, 30:97-105 (2014).
Borody et al., "Treatment of chronic constipation and colitis using human probiotic infusions," *Proceedings of Prebiotics and Probiotics and the New Foods Conference*, 2-4:228 Abstract (2001).
Borody et al., "Treatment of First-time Clostridium difficile Infection with Fecal Microbiota Transplantation," Poster Presentation, *2015 ACG Annual Scientific Meeting*, Honolulu, Hawaii, USA (2015).
Borody et al., "Treatment of Severe Constipation Improves Parkinson's Disease (PD) Symptoms," *AM J Gastro*, 104(S3):A999 (2009).
Borody et al., "Treatment of Severe Crohn's Disease (CD)—Using Rifabutin-Macrolide-Clofazimine Combination: Results at 30-37 Months," *Gastroenterology*, 118(4):A1334 Abstract (2000).
Borody et al., Treatment of Severe Crohn's Disease Using Rifabutin-Macrolide-Clofazimine Combination—Results at 38-43 Months, *J Gastroenterol & Hepatol*, 15(Suppl.):J102 (2000).
Borody et al., "Treatment of Severe Crohn's disease using antimycobacterial triple therapy—approaching a cure?," *Digest Liver Dis*, 34(1):29-38 (2002).
Borody et al., "Treatment of ulcerative colitis using fecal bacteriotherapy," *J Clin. Gastroenterol.*, 37(1):42-47 (2003).
Borody, "Bacteriotherapy for Chronic Fatigue Syndrome—A Long Term Follow-Up Study," *Proceedings of ACMA Complementary Medicine Sydney*, p. 1 (1995).

(56) References Cited

OTHER PUBLICATIONS

Borody, "Flora Power—Fecal Bacteria Cure Chronic C. difficile Diarrhoea," *Am J Gastroenterol*, 95(11):3028-3029 (2000).
Borody, "Is the Infected Patient too 'Difficile' to Treat?," The Australian Society for Microbiology 2009 Perth, SY03 & SY03. I, p. 27 & 56, (2009).
Borody, "Letter to the Editor—Response to Drs. Famularo et al.," *AJG*, 96(7):2262-2264 (2001).
Borriello, "Clostridial Disease of the Gut" Clinical Infectious Diseases, The University of Chicago, 20(Suppl 2):S242-S250 (1995).
Bowden et al., "Pseudomembraneous enterocolitis: mechanism of restoring floral homeostasis," *Am Surg.*, 47(4):178-183 (1981).
Brandt et al., "Endoscopic Fecal Microbiota Transplantation: "First-Line" Treatment for Severe Clostridium difficile Infection?" *J Clin. Gastroenterol.*, 45(8): 655-657 (2011).
Brandt et al., "Fecal microbiota transplantation for recurrent *Clostridium difficile* infection," *JClin Gastroenterol.*, 45(Suppl):S159-S167 (2011).
Brandt et al., "Long-Term Follow-Up Study of Fecal Microbiota Transplantation (FMT) for Ulcerative Colitis (UC)," Am. J. Gastroenterol., 107(Suppl 1):S657 (2012).
Brandt et al., Safety of Fecal Microbiota Transplantation (FMT) in Immunocompromised (Ie) Patients with Inflammatory Bowel Disease (IBD), *Am J Gastroenterol*, 108(Suppl 1): S556 (2013).
Browne et al., "Culturing of 'unculturable' human microbiota reveals novel taxa and extensive sporulation," *Nature*, 533(7604):543-546 (2016).
Bueche et al., "Quantification of Endospore-Forming Firmicutes by Quantitative PCR with the Functional Gene spo0A," *Applied and Environmental Microbiology*, 79(17):5302-5312 (2013).
Cammarota et al., "Randomised clinical trial: faecal microbiota transplantation by colonoscopy vs. vancomycin for the treatment of recurrent Clostridium difficile infection," Alimentary Pharmacology & Therapeutics, 41(9):835-843 (2015).
Cammorata et al., "Review article: biofile formation by Helicobacter pylori as a target for eradication of resistant infection," Aliment Pharmacol Ther, 36:222-30 (2012).
Campbell et al., "The many faces of Crohn's Disease: Latest concepts in etiology," *OJIM*, 2(2):107-115 (2012).
Cano et al., "Revival and identification of bacterial spores in 25-40 million year old Dominican Amber Science," Science, 268(5213):1060-1064 (1995).
Cato et al., "*Clostridium oroticum* comb. nov. amended description," *International Journal of Systematic Bacteriology*, 17(1):9-13 (1968).
Celik et al., "Factors influencing the stability of freeze-dried stress-resilient and stress-sensitive strains of bifidobacteria," J. Dairy Sci., 96(6):3506-16 (2013).
Center for Disease Control, "Severe Clostridium difficile-associated disease in populations previously at low risk-four states, 2005." *Morbidity and Mortality Weekly Report*, 54(47):1201-1205 (2005).
Chamberlain et al., "MAP-associated Crohn's Disease, MAP, Koch's postulates, causality and Crohn's Disease," *Digestive and Liver Disease*, 39:790-794 (2007).
Chamberlin et al., "Primary treatment of Crohn's disease: combined antibiotics taking center stage," *Expert Rev. Clin. Immunol.*, 7(6):751-760 (2011).
Chang et al., "Decreased diversity of the fecal Microbiome in recurrent Clostridium difficile-associated diarrhea," *J. Infect. Dis.*, 197(3):435-438 (2008).
Chen et al., "A mouse model of Clostridium difficile-associated disease," *Gastroenterology*, 135(6):1984-1992 (2008).
Cherif et al., "Thuricin 7: a novel bacteriocin produced by Bacillus thuringiensis BMG1.7, a new strain isolated from soil," Letters in Applied Microbiology, 32:243-7 (2001).
Chibani-Chennoufi et al., "In Vitro and In Vivo Bacteriolytic Activities of *Escherichia coli* Phages: Implications for Phage Therapy," *Antimicrobial Agents and Chemotherapy*, 48(7):2558-2569 (2004).
Choi et al., "Fecal Microbiota Transplantation: Current Applications, Effectiveness, and Future Perspectives," Clin. Endosc., 49:257-265 (2016).

Chopra et al., "Recent epidemiology of Clostridium difficile infection during hematopoietic stem cell transplantation," *Clin Transplant.*, 25(1):E82-E87 (2011).
Chu et al., "Profiling Living Bacteria Informs Preparation of Fecal Microbiota Transplantations," *PLOS One*, 1-16 (2017).
Citron et al., "In Vitro Activities of CB-183,315, Vancomycin, and Metronidazole against 556 Strains of *Clostridium difficile*, 445 Other Intestinal Anaerobes, and 56 *Enterobacteriaceae* Species," *Antimicrob Agents Chemother.*, 56(3):1613-1615 (2012).
Claesson et al., "Comparison of two next-generation sequencing technologies for resolving highly complex microbiota composition using tandem variable 16S rRNA gene regions," *Nucleic Acids Research*, 38(22):1-13 (2010).
Clancy et al., "Anti-MAP Therapy Induces and Maintains Remission in Severe Crohn's Disease," *Ann NY Acad Sci*, p. 1 (2005).
Claus et al., "Colonization-induced host-gut microbial metabolic interaction," *MBio*, 2(2):e00271-00210 (2011).
Claus et al., "Systemic multicompartmental effects of the gut microbiome on mouse metabolic phenotypes," *Mal. Syst. Biol.*, 4(1):219 (2008).
Cohen et al., "Clinical practice guidelines for Clostridium difficile infection in adults: 2010 update by the society for healthcare epidemiology of America (SHEA) and the infectious diseases society of America (IDSA)," *Infect Control Hosp Epidemiol.*, 31(5):431-55 (2010).
Collins et al., "The Phylogeny of the Genus *Clostridium*: Proposal of Five New Genera and Eleven New Species Combinations," *International Journal of Systematic Bacteriology*, pp. 812-826 (1994).
U.S. Appl. No. 12/843,409, filed Jul. 26, 2010.
Crohn's Disease, Prevention, Health Guide A-Z, WebMDHealth, pp. 1-2, n.d., Web, Oct. 23, 2005 <http://mywebmd.com/hw/inflammatory.sub.--bowel/uf6012.asp>.
Crowther, "Transport and Storage of Faeces for Bacteriological Examination," Journal of Applied Bacteriology, 34(2):477-483 (1971).
Cutolo et al., "Fecal feedings as a therapy in *Staphylococcus enterocolitis,*" NY State J Med, 59:3831-3833 (1959).
Dale et al., "Molecular interactions between bacterial symbionts and their hosts," *Cell*, 126(3):453-465 (2006).
Dan et al., "Comparison of preservation media and freezing conditions for storage of specimens of faeces," J. Med Microbiology, 28:151-154 (1989).
De Giulio et al., "Use of Alginate and Cryo-Protective Sugars to Improve the Viability of Lactic Acid Bacteria After Freezing and Freeze-Drying," World Journal of Microbiology & Biotechnology, 21:739-746 (2005).
Defang et al., "In vitro and in vivo evaluation of two extended release preparations of combination metformin and glipizide," *Drug Develop. & Indust. Pharm.*, 31:677-685 (2005).
Definition of Kit, Merriam-Webster, pp. 1-10., Web., 2019 <https://www.merriam-webster.com/dictionary/kit>.
Dendukuri et al., "Probiotic therapy for the prevention and treatment of Clostridium difficile-associated diarrhea: a systematic review," *CMAJ*, 173(2):167-170 (2005).
Derwent Abstract Accession No. 98-230427/20, WO 98/13068 A, (Kuperman VB) Apr. 2, 1998.
Dethlefsen et al., "An ecological and evolutionary perspective on human-microbe mutualism and disease," *Nature*, 449(7164):811-818 (2007).
Dewhirst et al., "Phylogeny of the Defined Murine Microbiota: Altered Schaedler Flora," *Applied and Environmental Microbiology*, 65(8):3287-3292 (1999).
DuPont "The search for effective treatment of Clostridium difficile infection," *N Engl J Med.*, 364(5):473-475 (2011).
Eckburg et al., "Diversity of the human intestinal microbial flora," *Science*, 308(5728):1635-1638 (2005).
Eiseman et al., "Fecal enema as an adjunct in the treatment of pseudomembranous enterocolitis," *Surgery*, 44(5):854-859 (1958).
Eller et al., "Anaerobic Roll Tube Media for Nonselective Enumeration and Isolation and Bacteria in Human Feces," Applied Microbiology, 22(4):522-529 (1971).
Extended European Search Report dated Apr. 3, 2014, in European Patent Application No. 11813951.8.

(56) References Cited

OTHER PUBLICATIONS

Extended European Search Report dated Mar. 16, 2018, in European Patent Application No. 17203052.0.
Extended European Search Report dated Nov. 30, 2016, in European Patent Application No. 16193790.9.
Faust et al., "Treatment of recurrent pseudomembranous colitis (RPMC) with stool transplantationHerewith (ST): Report of six (6) cases," *Can J Gastroenterol.*, 1 6:A43 (2002).
Fenton et al., "Pseudomembranous colitis associated with antibiotic therapy—an emerging entity," *Can Med Assoc J*, 111(10):1110-1111 (1974).
Floch et al., "Probiotics and Dietary Fiber, The Clinical Coming of Age of Intestinal Microecology," J. Clin. Gastroenterology, 27(2):99-100 (1998).
Floch, "Fecal Bacteriotherapy, Fecal Transplant, and the Microbiome," J. Clin. Gastroenterol., 44(8):529-530 (2010).
Flotterod et al., "Refractory Clostridium difficile infection. Untraditional treatment of antibiotic-induced colitis," *Tidsskr nor Laegeforen*, 111:1364-1365 (1991).
Frank et al., "Molecular-phylogenetic characterization of microbial community imbalances in human inflammatory bowel diseases," *PNAS*, 104(34):13780-13785 (2007).
Frantzen et al., "Empirical evaluation of preservation methods for faecal DNA," *Molecular Ecology*, 7(10):1423-1428 (1998).
Freeman et al., "The changing epidemiology of Clostridium difficile infections," *Clin Microbial. Rev.*, 23(3):529-549 (2010).
Frese et al., "The evolution of host specialization in the vertebrate gut symbiont Lactobacillus reuteri," *PloS Genet.*, 7(2):e1001314 (2011).
Gaboriau-Routhiau et al., "The Key Role of Segmented Filamentous Bacteria in the Coordinated Maturation of Gut Helper T Cell Responses," *Immunity*, 31(4):677-689 (2009).
Garborg et al., "Results of faecal donor instillation therapy for recurrent Clostridium difficile-associated diarrhoea," *Scand J Infect Dis.*, 42(11-12):857-61 (2010).
Garey et al., "Meta-analysis to assess risk factors for recurrent Clostridium difficile infection," *J Hosp. Infect.*, 70(4):298-304 (2008).
Gerding, "Management of Clostridium difficile infection: thinking inside and outside the box," *Clin Infect Dis.*, 51(11):1306-13 (2010).
Geuking et al., "Intestinal Bacterial Colonization Induces Mutualistic Regulatory T Cell Responses," *Immunity*, 34:794-806 (2011).
Gitlin et al., "*Mycobacterium avium* ss *paratuberculosis*-associated Diseases: Piecing the Crohn's Puzzle Together," *J Clin Gastroenterol*, 46(8):649-655 (2012).
Gough et al., "Systematic review of intestinal microbiota transplantation (fecal bacteriotherapy) for recurrent Clostridium difficile infection," *Clin. Infect. Dis.*, 53(10):994-1002 (2011).
Grehan et al., "Durable alteration of the colonic microbiota by the administration of donor fecal flora," *Journal of Clinical Gastroenterology*, 44(8):551-561 (2010).
Guarner et al., "Gut flora in health and disease," *Lancet*, 361(9356):512-519 (2003).
Gustafsson et al., "The Effect of Faecal Enema on Five Microflora-Associated Characteristics in Patients with Antibiotic-Associated Diarrhoea," *Scandinavian Journal of Gastroenterology*, 34:580-586 (1999).
Gustafsson et al., "Faecal Short-Chain Fatty Acids in Patients with Antibiotic-Associated Diarrhoea, before and after Faecal Enema Treatment," *Scand J Gastroenterol*, 33:721-727 (1998).
Hamilton et al., "Change in microbial community composition of in patients with recalcitrant Clostridium difficile colitis treated with fecal bacteriotherapy," International Human Microbiome Congress, Poster and Presentation, Vancouver, ON, Canada, Mar. 9-11, 2011.
Hamilton et al., "High-throughput DNA sequence analysis reveals stable engraftment of gut microbiota following transplantation of gut microbiota following transplantation of previously frozen fecal bacteria," Gut Microbes, 4(2):1-11 (2013).

Hamilton et al., "Standardized Frozen Preparation for Transplantation of Fecal Microbiota for Recurrent Clostridium difficile Infection," Article and Supplementary Material, *Am. J. Gastroenterol.*, 107(5):761-767 (2012).
Hayashi et al., "Phylogenetic Analysis of the Human Gut Microbiota Using 16S rDNA Clone Libraries and Strictly Anaerobic Culture-Based Methods," *Microbial. Immunol.*, 46(8):535-548 (2002).
Hecker et al., "Fecal Microbiota Transplantation by Freeze-Dried Oral Capsules for Recurrent Clostridium difficile Infection," *Open Forum Infect Dis*, 3(2): 1-2 (2016).
Hellemans et al., "Fecal transplantation for recurrent Clostridium difficile colitis, an underused treatment modality," *Acta Gastroenterol Belg.*, 72(2):269-70 (2009).
Henriksson et al., "Probiotics under the regulatory microscope," *Expert Opin. Drug Saf*, 4(6):1-9 (2005).
Hensel et al., "Vagal Ascent and Distribution of 125 I-Tetanus Toxin after Injection into the Anterior Wall of the Stomach," Naunyn-Schmiedeberg's Arch. Pharmacol, 276:395-402 (1973).
Honda et al., "Regulation of T Cell Responses by Intestinal Commensal Bacteria," *Journal of Intestinal Microbiology*, vol. 25, 2nd Edition:104 (2011).
Hongliang et al., "Freeze-dried, Capsulized Fecal Microbiota Transplantation for Relapsing Clostridium difficile Infection," *Journal of Clinical Gastroenterology*, 43(6):537-538 (2015).
Hooper et al., "How host-microbial interactions shape the nutrient environment of the mammalian intestine," *Annu. Rev. Nutr.*, 22:283-307 (2002).
Hope et al., "Sporadic colorectal cancer-role of the commensal microbiota," *FEMS Microbial. Lett.*, 244:1-7 (2005).
Hota et al., "Determining Mortality Rates Attributable to Clostridium difficile Infection," *Emerg. Infect. Dis.*, 18(2):305-307 (2012).
Hota et al., "Oral Vancomycin Followed by Fecal Transplant Versus Tapering Oral Vancomycin," U.S. National Institutes of Health, Clinical Study No. NCT01226992, Oct. 20, 2010, last updated Jan. 14, 2013, Web, May 20, 2014, pp. 1-4 <http://clinicaltrials.gov/ct2/show/NCT01226992>.
Hsu et al., "IL-10 Potentiates Differentiation of Human Induced Regulatory T Cells via STAT3 and Foxol," *The Journal of Immunology*, 3665-3674 (2015).
Hu et al., "Prospective derivation and validation of a clinical prediction rule for recurrent Clostridium difficile infection," *Gastroenterology*, 136:1206-1214 (2009).
Huang et al., "Once-daily propranolol extended-release tablet dosage form: formulation design and in vitro/in vivo investigation," *European J of Pharm. & Biopharm.*, 58:607-614 (2004).
Huttenhower et al., "Structure, function and diversity of the healthy human microbiome," The Human Microbiome Project Consortium, *Nature*, 486:207-214 (2012).
Immunology in the 21st Century: Defeating Infection, Autoimmunity, Allergy, and Cancer, ICI 2010 Wrap-up Report, 14th International Congress of Immunology, pp. 1 (2010).
Inflammatory Bowel Disease Facts, Disease Prevention and Treatment Strategies, Crohn's Disease and Inflammatory Bowel Disease (IBD), HealingWithNutrition.com, pp. 1-4, n.d., Web, Oct. 23, 2005 <http://www.HealingWithNutrition.com/disease/inflambowel/chrohns.html>.
Information Disclosure Statement filed Nov. 28, 2017, in U.S. Appl. No. 15/487,553
International Preliminary Examination Report completed Nov. 19, 2002, in International Application No. PCT/AU2001/000907, 19 pgs.
International Preliminary Report on Patentability completed Dec. 12, 2012, in International No. PCT/AU2011/000987, 35 pgs.
International Preliminary Report on Patentability completed Mar. 12, 2015, in International Application No. PCT/AU2013/001362, 29 pgs.
International Preliminary Report on Patentability dated Sep. 10, 2013, in International Application No. PCT/US2012/028484, 10 pgs.
International Search Report and Written Opinion (WO) dated Feb. 2, 2018 in International Application No. PCT/US2017 /055618.
International Search Report and Written Opinion (WO) dated Feb. 2, 2018 in International Application No. PCT/US2017/056131.

(56) References Cited

OTHER PUBLICATIONS

International Search Report and Written Opinion (WO) dated Feb. 21, 2018 in International Application No. PCT/US2017/056129.
International Search Report and Written Opinion (WO) dated Jan. 17, 2018, in International Application No. PCT/US2017 /045092.
International Search Report and Written Opinion (WO) dated Jan. 31, 2018 in International Application PCT/US2017/056126.
International Search Report and Written Opinion dated Aug. 17, 2018, in International Application No. PCT/US2018/034673.
International Search Report and Written Opinion dated Aug. 2, 2018, in International Application No. PCT/US2018/026074.
International Search Report and Written Opinion dated Jul. 30, 2018, in International Application No. PCT/US2018/026080.
International Search Report and Written Opinion dated Aug. 8, 2016, in International Application No. PCT/US2016/032695, 10 pgs.
International Search Report and Written Opinion dated Feb. 5, 2014, in International Application No. PCT/AU2013/001362, 17 pgs.
International Search Report and Written Opinion dated Jan. 5, 2017, in International Application No. PCT/US2016/058938.
International Search Report and Written Opinion dated Jul. 31, 2014, in International Application No. PCT/US2014/027391, 16 pgs.
International Search Report and Written Opinion dated Oct. 28, 2011, in International No. PCT/AU2011/000987, 18 pgs.
International Search Report dated Aug. 10, 2012, in International Application No. PCT/US2012/028484, 7 pgs.
International Search Report dated Jul. 29, 2014, in International Application No. PCT/AU2014/000478, 7 pgs.
International Search Report dated Sep. 22, 2017, in International Application No. PCT/US2017/040591, 12 pgs.
Irrgang et al., "The historical Development ofMutaflor therapy," Ardeypharm GmbH, pp. 1-38 (1988) <http://www.ardeypharm.de/pdfs/en/mutaflor_historical_e.pdf?>.
Irritable Bowel Syndrome (IBS), Health A to Z, InteliHealth, pp. 1-4, n.d., Web, Oct. 23, 2005 <http://www.intelihealth.com>.
Issa et al., "Clostridium difficile and Inflammatory Bowel Disease," *Inflamm Bowel Dis.*, 14(10):1432-1442 (2008).
Issa et al., "Impact of Clostridium difficile on inflammatory bowel disease," *Clin. Gastroenterol. Hepatol.*, 5(3):345-351 (2007).
Itoh et al., "Characterization of clostridia isolated from faeces of limited flora mice and their effect on caecal size when associated with germ-free mice," *Laboratory Animals*, 19:111-118 (1985).
Itoh et al., "Intestinal bacteria antagonistic to *Clostridium difficile* in mice," *Laboratory Animals*, 21:20-25 (1987).
Ivanov et al., "Specific Microbiota Direct the Differentiation of IL-17-Producing T-Helper Cells in the Mucosa of the Small Intestine," *Cell Host & Microbe*, 4:337-349 (2008).
Jacob et al., "Single Delivery of High-Diversity Fecal Microbiota Preparation by Colonoscopy Is Safe and Effective in Increasing Microbial Diversity in Active Ulcerative Colitis," *Inflamm Bowel Dis.*, 0(0):1-9 (2017).
Janeway et al., "Adaptive Immunity to Infection," *Immunobiology*, 6th Edition, Chapter 10, pp. 414 (2005).
Janeway, Jr. et al., "Autoimmune responses are directed against self antigens," *Immunobiology: The Immune System in Health and Disease*, 5th Edition, pp. 1-4 (2001).
Jarvis et al., "National point prevalence of Clostridium difficile in US health care facility inpatients, 2008," *Am. J. Infect. Control*, 37:263-270 (2009).
Johnson et al., "Interruption of Recurrent Clostridium difficile-Associated Diarrhea Episodes by Serial Therapy with Vancomycin and Rifaximin," *Clin. Infect. Dis.*, 44(6):846-848 (2007).
Johnson et al., "Rifaximin Redux: Treatment of recurrent Clostridium difficile infections with Rifaximin immediately post-vancomycin treatment," *Anaerobe*, 15(6):290-291 (2009).
Kageyama et al., "Emendation of genus Collinsella and proposal of *Collinsella stercoris* sp. nov. and *Collinsella intestinalis* sp. nov.,'' International Journal of Systematic and Evolutionary Microbiology, 50:1767-1774 (2000).

Kageyama et al., "Phylogenetic and phenotypic evidence for the transfer of Eubacterium aerofaciens to the genus *Collinsella* as *Collinsella aerofaciens* gen. nov., comb. nov.," International Journal of Systematic Bacteriology, 49:557-565 (1999).
Kakihana et al., "Fecal microbiota transplantation for patients with steriod-resistant acute graft-versus-host disease of the gut," *Blood*, 128(16):2083-2088 (2016).
Kamboj et al., "Relapse versus reinfection: surveillance of Clostridium difficile infection," *Clininfect Dis.*, 53(10):1003-1006 (2011).
Kang et al., "Microbiota Transfer Therapy alters gut ecosystem and improves gastrointestinal and autism symptoms: an open-label study," Microbiome, 5:10, 16 pages (2017).
Karas et al., "A review of mortality due to Clostridium difficile infection," *J Infect.*, 61(1):1-8 (2010).
Kassam et al., "Fecal transplant via retention enema for refractory or recurrent Clostridium difficile infection," *Arch Intern Med.*, 172(2): 191-193 (2012).
Kelly et al., "Commensal gut bacteria: mechanisms of immune modulation," *Trends in Immunology*, 26(6):326-333 (2005).
Kelly et al., "Clostridium difficile—more difficult than ever," *N. Engl. J. Med.*, 359(18):1932-1940 (2008).
Kelly et al., "Clostridium difficile colitis," *N Engl. J Med.*, 330(4):257-62 (1994).
Kelly et al., "Fecal Microbiota Transplant for Treatment of *Clostridium difficile* Infection in Immunocompromised Patients," *Am J Gastroenterol*, 109:1065-1071 (2014).
Kelly et al., "Fecal microbiota transplantation for relapsing Clostridium difficile infection in 26 patients: methodology and results," *J Clin. Gastroenterol.*, 46(2): 145-149 (2012).
Keynan et al., "The Role of Regulatory T Cells in Chronic and Acute Viral Infections," *Clinical Infectious Diseases*, 46:1046-1052 (2008).
Khanna et al., "A Novel Microbiome Therapeutic Increases Gut Microbial Diversity and Prevents Recurrent Clostridium difficile Infection," The Journal of Infectious Diseases, 214:173-81 (2016).
Khanna et al., "The epidemiology of community-acquired Clostridium difficile infection: a population-based study," *Am J Gastroenterol.*, 107(1):89-95 (2012).
Khanna et al., "The growing incidence and severity of Clostridium difficile infection in inpatient and outpatient settings," *Expert Rev Gastroenterol Hepatol.*, 4(4):409-16 (2010).
Kharidia et al., "The Activity of a Small Lytic Peptide PTP-7 on *Staphylococcus aureus* Biofilms," *J Microbial.*, 49(4):663-668 (2011).
Khomts et al., "Changes in the composition of the human fecal microbiome after bacteriotherapy for recurrent Clostridium difficile-associated diarrhea," *J Clin. Gastroenterol.*, 44(5):354-360 (2010).
Khomts et al., "Therapeutic transplantation of the distal gut microbiota," *Mucosal Immunol.*, 4(1):4-7 (2011).
Kim et al., "Effect of Rifampin on the Plasma Concentration and the Clinical Effect of Haloperidol Concomitantly Administered to Schizophrenic Patients," Journal of Clinical Psychopharmacology, 16(3):247-252 (1996).
Kim et al., "In Vitro Culture Conditions for Maintaining a Complex Population of Human Gastrointestinal Tract Microbiota," Journal of Biomedicine and Biotechnology, 2011(Article ID 838040):1-10 (2011) <http://www.hindawi.com/journals/bmri/2011/838040/>.
Klaenhammer, "Bacteriocins of lactic acid bacteria," Biochimie, 70:337-49 (1988).
Kleiman et al., "Comparison of two coprological methods for the veterinary diagnosis of fasciolosis," *Arquivo Brasileiro de Medicina Veterinaria e Zootccnica*, 55(2):181-185 (2005).
Kobashi et al., "Metabolism of Sennosides by Human Intestinal Bacteria," Journal of Medicinal Plant Research, 40(3):225-236 (1980).
Koch, "What size should a bacterium be? A question of scale," Annu. Rev. Microbial., 50:317-48 (1996).
Krogius-Kurikka et al., "Sequence analysis of percent G+C fraction libraries of human faecal bacterial DNA reveals a high number of *Antinobacteria*," *BMC Microbiology*, 9(68):1-13 (2009).
Kuijper et al. "Update of Clostridium difficile Infection due to PCR Ribotype 027 in Europe, 2008," *Euro. Surveill.*, 13(31):Article 5 (2008).

(56) References Cited

OTHER PUBLICATIONS

Kuksal et al., "Formulation and In Vitro, In Vivo Evaluation of Extended-release Matrix Tablet of Zidovudine: Influence of Combination of Hydrophilic and Hydrophobic Matrix Formers," *AAPS Pharm.*, 7(1):E1-E9 (2006).
Kunde et al., "Safety, Tolerability, and Clinical Response After Fecal Transplantation in Children and Young Adults With Ulcerative Colitis," *JPNG*, 56(6):597-601 (2013).
Kyne et al., "Association between antibody response to toxin A and protection against recurrent Clostridium difficile diarrhea," *Lancet*, 357(9251):189-93 (2001).
Kyne et al., "Asymptomatic carriage of Clostridium difficile and serum levels of IgG antibody against toxin A," *N Engl J Med.*, 342(6):390-397 (2000).
Kyne et al., "Factors associated with prolonged symptoms and severe disease due to Clostridium difficile," *Age and Ageing*, 28(2):107-13 (1999).
Kysela et al., "Serial analysis of V6 ribosomal sequence tags (SARST-V6): a method for efficient, high-throughput analysis of microbial community composition," *Environmental Microbiology*, 7(3):356-364 (2005).
Labbe et al., "Clostridium difficile infections in a Canadian tertiary care hospital before and during a regional epidemic associated with the BI/NAPI/027 strain," *Antimicrob Agents Chemother.*, 52(9):3180-7 (2008).
Lamontagne et al., "Impact of emergency colectomy on survival of patients with fulminant Clostridium difficile colitis during an epidemic caused by a hypervirulent strain," *Ann. Surg.*, 245(2):267-272 (2007).
Larsen et al., "Gut Microbiota in Human Adults with Type 2 Diabetes Differs from Non-Diabetic Adults," PLoS One, 5(2): e9085-e9095 (2010).
Lau et al., "Bacteraemia caused by *Anaerotruncus colihominis* and emended description of the species," *JClin Pathol*, 59:748-752 (2006).
Lawson et al., "*Anaerotruncus colihominis* gen. nov., sp. nov., from human faeces," *International Journal of Systematic and Evolutionary Microbiology*, 54:413-417 (2004).
Lawson et al., "Anaerotruncus," *Bergey's Manual of Systematics of Archae and Bacteria*, pp. 1-4 (2009).
Lee et al., "Prioritizing candidate disease genes by network-based boosting of genome-wide association data," Genome Research, 21(1):1109-1121 (2011).
Lee et al., "The outcome and long-term follow-up of 94 patients with recurrent and refractory *Clostridium difficile* infection using single to multiple fecal microbiota transplantationHerewith vie retention enema," *European Journal Clinical Microbiology Infect Dis.*, 33:1425-1428 (2014).
Lee, "A Prospective Randomized Multi-Centre Trial of Fresh vs. Frozen-and-Thawed Human Biotherapy (Fecal Transplant) for Recurrent Clostridium difficile Infection," U.S. National Institutes of Health, Clinical Study No. NCT01398969, pp. 1-4, last updated Feb. 27, 2014, Web, May 20, 2014 <http://clinicaltrials.gov/ct2/show/NCT01398969>.
Leis et al., "Fecal microbiota transplantation: A 'How-To' guide for nurses," *Collegian*, 22:445-451 (2015).
Leslie et al., "Trehalose and Sucrose Protect Both Membranes and Proteins in Intact Bacteria during Drying," Applied and Environmental Microbiology, 61:3592-3597 (1995).
Lewis et al., "Stool form scale as a useful guide to intestinal transit time," *Scand. J. Gastroenterol.*, 32(9):920-924 (1997).
Ley et al.,"Ecological and evolutionary forces shaping microbial diversity in the human intestine," *Cell*, 124:837-848 (2006).
Ley et al., "Evolution of mammals and their gut microbes," *Science*, 320(5883): 1647-1651 (2008).
Ley et al., "Microbial ecology: human gut microbes associated with obesity," *Nature*, 444(7122):1022-3 (2006).
Ley et al., "Worlds within worlds: evolution of the vertebrate gut microbiota," *Nat. Rev. Microbial.*, 6(10):776-788 (2008).

Lin et al., "Twelve Week Storage Trial of Microbial Viability in Lyophilized and Frozen Fecal Microbiota Preparations," Poster Presentation—Digestive Disease Week 2015, Washington, D.C. USA.
Longstreth, "Irritable bowel syndrome: A multibillion-dollar problem," Gastroenterology, 109(6):2029-2031 (1995).
Loo et al., "A predominantly clonal multi institutional outbreak of Clostridium difficile-associated diarrhea with high morbidity and mortality," *N Engl J Med*, 353(23):2442-9 (2005).
Loo et al., "Host and pathogen factors for Clostridium difficile infection and colonization," *N Engl J Med*, 365(18):1693-703 (2011).
Louie et al., "Fidaxomicin versus vancomycin for Clostridium difficile infection," *N Engl. J. Med.*, 364(5):422-431 (2011).
Louie et al.,"Home-based fecal flora infusion to arrest multiply-recurrent C. difficile infection," ICAAC/IDSA Conference, Abstract #K-4201 (2008).
Louis et al., "Diversity, metabolism and microbial ecology of butyrate-producing bacteria from the human large intestine," *FEMS Microbiology Letters*, 294:1-8 (2009).
Lu, "Taboo transplant: How new poo defeats superbugs," Science News, 1:90-91 (2011).
Ludwig et al., "Taxonomic outline of the phylumFirmicutes," Bergey's Manual of Systematic Bacteriology, 3:15-17 (2009).
Lund-Tonnesen et al., "Clostridium difficile-associated diarrhea treated with homologous faeces," *Tidsskr nor Lageforen*, 118:1027-1030 (1998).
MacConnachie et al., "Faecal transplant for recurrent Clostridium difficile-associated diarrhoea: a UK case series," *QJM*, 102 (11):781-784 (2009).
MacDonald et al., "Formation of Ursodeoxycholic Acid from Chenodeoxycholic Acid by a 7b-Hydroxysteroid Dehydrogenase-Elaborating Eubacterium aerofaciens Strain Cocultured with 7a-Hydroxysteroid Dehydrogenase-Elaborating Organisms," Applied and Environmental Microbiology, 44(5):1187-1195 (1982).
Macpherson et al., "Induction of Protective IgA by Intestinal Dendritic Cells Carrying Commensal Bacteria," *Science*, 303:1662-1665 (2004).
Madsen, "The use of probiotics in gastrointestinal disease," Can J Gastroenterol, 15(12):817-22 (2001).
Maizels et al., "Regulatory T cells in Infection," *Advances in Immunology*, Chapter 3, 112:73-136 (2011).
Manichanh et al., "Reshaping the gut microbiome with bacterial transplantation and antibiotic intake," Genome Research20:1411-1419 (2010).
Marchesi et al., "The normal intestinal microbiota," *Curr. Opin. Infect. Dis.*, 20(5):508-513 (2007).
Martin, "Development and Delivery of a Treatment for Clostridium difficile," *Bacteriotherapy*, pp. 1-2, n.d., Web, Feb. 10, 2012 <www.bacteriotherapy.org>.
Martin-Dejardin et al., "A way to follow the viability of encapsulated Bifidobacterium bifidum subjected to a freeze-drying process in order to target the colon: Interest of flow cytometry," European Journal of Pharmaceutical Sciences, 49:166-74 (2013).
Maslowski et al., "Diet, gut microbiota and immune responses," *Nat Immunol.*, 12(1):5-9 (2011).
McDonald et al., "An Epidemic, Toxin Gene-Variant Strain of Clostridium difficile," *N Engl J Med.*, 353(23):2433-41 (2005).
McDonald et al., "Clostridium difficile Infection in Patients Discharged from US Short-stay Hospitals, 1996-2003" *Emerg. Infect. Dis*, 12(3):409-415 (2006).
McFarland et al., "Breaking the Cycle: Treatment Strategies for 163 Cases of Recurrent Clostridium difficile Disease," *Am. J. Gastroenterol.*, 97(7):1769-1775 (2002).
McFarland et al., "Implications of the changing face of Clostridium difficile disease for health care practitioners," *Am J Infect Control.*, 35(4):237-253 (2007).
McFarland et al., "Meta-Analysis of Probiotics for the Prevention of Antibiotic Associated Diarrhea and the Treatment of Clostridium difficile Disease," *Am J Gastroenterol.*, 101(4):812-22 (2006).
McFarland et al., "Nosocomial Acquisition of Clostridium Difficile Infection," *N Engl J Med.*, 320(4):204-210 (1989).

(56) References Cited

OTHER PUBLICATIONS

McFarland et al., "Recurrent Clostridium Difficile Disease: Epidemiology and Clinical Characteristics," *Infect Control Hosp Epidemiol.*, 20(1):43-50 (1999).

McFarland et al., "Renewed interest in a difficult disease: Clostridium difficile infections—epidemiology and current treatment strategies," *Curr Opin Gastroenterol.*, 25(1):24-35 (2008).

Miller et al., "Health care-associated Clostridium difficile infection in Canada: patient age and infecting strain type are highly predictive of severe outcome and mortality," Clin Infect Dis., 50(2):194-201 (2010).

Miller et al., "Long-term follow-up of patients with fulminant Clostridium difficile colitis," *J Gastrointest. Surg.*, 13(5):956-959 (2009).

Miller et al., "Morbidity, mortality, and healthcare burden of nosocomial Clostridium difficile-associated diarrhea in Canadian hospitals," *Infect Control Hosp Epidemiol.*, 23(3):137-40 (2002).

Miller, "The fascination with probiotics for Clostridium difficile infection: lack of evidence for prophylactic or therapeutic efficacy," *Anaerobe*, 15(6):281-284 (2009).

Moayyedi et al., "Fecal Microbiota Transplantation Induces Remission in Patients With Active Ulcerative Colitis in a Randomized Controlled Trial," Gastroenterology, 149(1):102-9 (2015).

Molecular Studies in Autism, 2004 Funding Cycle, Cure Autism Now, Cure Autism Now Foundation, pp. 1-7 (2005) <www.cureautismnow.org>.

Momose et al., "16S rRNA gene sequence-based analysis of clostridia related to conversion of germfree mice to the normal state," *Journal of Applied Microbiology*, 107:2088-2097 (2009).

Morris et al., "Clostridium difficile Colitis: An Increasingly Aggressive Iatrogenic Disease?" *Arch Surg.*, 137(10):1096-1100 (2002).

Mucosal immunity: homeostasis (WS-064): Chairpersons: Toshiaki Ohteki, Makoto Iwata, *International Immunology*, 22:Suppl 1 Pt. 3, 1-9 (2010).

Mullard, "Microbiology: The Inside Story," *Nature*, 453:578-580 (2008).

Murai et al., "Interleukin 10 acts on regulatory T cells to maintain expression of the transcription factor Foxp3 and suppressive function in mice with colitis," *Nat Immunol.*, pp. 1-20 (2009).

Mutaflor, "Brief Summary of Therapeutic Principles," Ardeypharm GmbH 0796 D-58313 Herdecke Germany, 6 pgs (2006).

Mutaflor, "For Functional and Inflammatory Bowel Diseases for Extraintestinal Manifestations for Activation of the Body's In-Built Defences," Ardeypharm GmbH 0796, D-58313 Herdecke Germany, 8 pgs (2006).

Mutaflor, "Safety of Therapy," Ardeypharm GmbH 0796, D-58313 Herdecke Germany, 4 pgs (1988).

Muto et al., "A Large Outbreak of Clostridium difficile-Associated Disease with an Unexpected Proportion of Deaths and Colectomies at a Teaching Hospital Following Increased Fluoroquinolone Use," *Infect Control Hosp Epidemiol.*, 26(3):273-80 (2005).

Nieuwdorp et al., ["Treatment of recurrent Clostridium difficile-associated diarrhoea with a suspension of donor faeces"], *Ned Tijdschr Geneeskd*, 152(35):1927-32 (2008) (English abstract).

Niu et al., "Prevalence and Impact of Bacteriophages on the Presence of *Escherichia coli* O157:H7 in Feedlot Cattle and Their Environment," Applied and Environmental Microbiology, 75(5):1271-8 (2009).

O'Hara et al., "The gut flora as a forgotten organ," *EMBO Rep.*, 7(7):688-693 (2006).

O'Brien et al., "The emerging infectious challenge of clostridium difficile-associated disease in Massachusetts hospitals: clinical and economic consequences," Infect Control Hosp Epidemiol., 28(11):1219-27 (2007).

O'Connor et al., "Clostridium difficile Infection Caused by the Epidemic BI/NAP1/027 Strain," *Gastroenterology*, 136(6):1913-1924 (2009).

Office Action dated Sep. 18, 2015, in European Patent Application No. 11 728 077.6.

O'Garra et al., "IL-10—producing and naturally occurring CD4+ Tregs: limiting collateral damage," *The Journal of Clinical Investigation*, 114:1372-1378 (2004).

O'Hara et al., "Functional modulation of human intestinal epithelial cell responses by Bifidobacterium infantis and Lactobacillus salivarius," *Immunology* 118:202-215 (2006).

Okada et al., "Effects of Fecal Microorganisms and Their Chloroform-Resistant Variants Derived from Mice, Rats, and Humans on Immunological and Physiological Characteristics of the Intestines ofExgerrnfree Mice," *Infection and Immunity*, 62(12):5442-5446 (1994).

Olson et al., "The Gut Microbiota Mediates the Anti-Seizure Effects of the Ketogenic Diet," Cell, 173:1728-1741 (2018) <https://linkinghub.elsevier.com/retrieve/pii/S0092867418305208>.

Ott et al., "Efficacy of Sterile Fecal Filtrate Transfer for Treating Patients With Clostridium difficile Infection," Gastroenterology, 152(4):799-811 (2017).

Paramsothy et al., "Gastroenterologist perceptions of faecal microbiota transplantation," *World J Gastroenterol*, 21(38): 10907-10914 (2015).

Paramsothy et al., "Multidonor intensive faecal microbiota transplantation for active ulcerative colitis: a randomised placebo-controlled trial," The Lancet, published online, 11 pages (2017).

Paterson et al., "Putting back the bugs: Bacterial treatment relieves chronic diarrhoea," *Med J Aus*, 160:232-233 (1994).

Patterson et al., "Special organism isolation: attempting to bridge the gap," *Infect Control Hosp Epidemiol.*, 15(5):335-338 (1994).

Pearce et al., "Modification of the colonic microflora using probiotics: The way forward?," *Gut*, 4l(Suppl 3):A63 (1997).

Pearce et al., "The use of probiotic therapy as a novel approach to the management of irritable bowel syndrome: a preliminary study," *J Gastroenterol & Hepatol*, 12(Suppl):A129 (1997).

Pepin et al., "Clostridium difficile-associated diarrhea in a region of Quebec from 1991 to 2003: a changing pattern of disease severity," *CMAJ*, 171(5):466-472 (2004).

Pepin et al., "Emergence of Fluoroquinolones as the Predominant Risk Factor for Clostridium difficile-Associated Diarrhea: A Cohort Study During an Epidemic in Quebec," *Clin Infect Dis.*, 41(9):1254-1260 (2005).

Pepin et al., "Management and Outcomes of a First Recurrence of Clostridium difficile-Associated Disease in Quebec, Canada," *Clin. Infect. Dis.*, 42:758-764 (2006).

Persky et al., "Treatment of recurrent Clostridium difficile-associated diarrhea by administration of donated stool directly through a colonoscope," *Am J Gastroenterol.*, 95(11):3283-3285 (2000).

Petrof et al.,"Stool substitute transplant therapy for the eradication of Clostridium difficile infection: 'RePOOPulating' the gut," *Microbiome*, 1:3 (2013).

Petrof, "Harnessing the healthy gut microbiota to cure patients with recurrent C. difficile infection," U.S. National Institutes of Health, Clinical Study No. NCT01372943, pp. 1-2, last updated Nov. 6, 2013, Web, May 22, 2014 <http://clinicaltrials.gov/ct2/show/NCT01372943>.

Pillai et al., "Probiotics for treatment of Clostridium difficile-associated colitis in adults (Review)," *Cochrane Database Syst Rev.*, (l):CD00461 I (2008).

Porter, "Coating of pharmaceutical dosage forms," In D.B. Troy (Ed.), Reminglon: The Science and Practice of Pharmacy, Chapter 46, pp. 929-938 (2005).

Poster 064-03 presented at the 14th International Congress of Immunology, Aug. 22-27, 2010, in Kyoto (Atarashi et al., Regulation of colonic regulatory T cells by *Clostridium* species).

Prakash et al., "Colon-targeted delivery of live bacterial cell biotherapeutics including microencapsulated live bacterial cells," *Biologics: Targets & Therapy*, 2(3):355-378 (2008).

Prevention of Sudden Infant Death Syndrome, Healthtouch.com, Thomson Micromedex, pp. 1-4, n.d., Web, Nov. 23, 2005.

Qiu et al., "*Faecalibacterium prausnitzii* upregulates regulatory T cells and anti-inflammatory cytokines in treating TNBS-induced colitis," *Journal of Crohn's and Colitis*, 7:e558-e568 (2013).

Rabeneck et al., "Bleeding and perforation after outpatient colonoscopy and their risk factors in usual clinical practice," *Gastroenterology*, 135(6):1899-1906 (2008).

(56) References Cited

OTHER PUBLICATIONS

Rager et al., "Evaluation of rumen transformation after surgical correction of left-sided displacement of the abomasum in cows," *J Am. Vet. Med. Assoc.*, 225(6):915-920 (2004).
Ramesh et al., "Prevention of Clostridium difficile-induced ileocecitis with Bacteriophage," *Anaerobe*, 5:69-78 (1999).
Rao et al., "Evaluation of gastrointestinal transit in clinical practice: position paper of the American and European Neurogastroenterology and Motility Societies," *Neurogastroenterol. Motil.*, 23(1):8-23 (2011).
Rautava, "Potential uses of probiotics in the neonate," Seminars in Fetal & Neonatal Medicine, 12:45-53 (2007).
Rea et al., "Gut solutions to a gut problem: bacteriocins, probiotics and bacteriophage for control of Clostridium difficile infection," Journal of Medical Microbiology, 62:1369-1378 (2013).
Redelings et al., "Increase in Clostridium difficile-related mortality rates, United States, 1999-2004," *Emerg Infect Dis.*, 13(9):1417-1419 (2007).
Response to Office Action filed Feb. 25, 2014, in European Patent Application No. 11728077.6.
Response to Office Action filed Jan. 28, 2015, in European Patent Application No. 11728077.6.
Response to Office Action filed Nov. 18, 2015, in European Patent Application No. 11728077.6.
Rex et al., "American College of Gastroenterology guidelines for colorectal cancer screening 2008," *Am. J. Gastroenterol.*, 104(3):739-750 (2009).
Ricciardi et al., "Increasing prevalence and severity of Clostridium difficile colitis in hospitalized patients in the United States," *Arch Surg.*, 142(7):624-631 (2007).
Roberts, Generation and Development Microbial Drug Products, CSO Vedanta Biosciences, 1st Microbiome Drug Development Summit, pp. 1-17 (2016).
Rodemann et al., "Incidence of Clostridium difficile infection in inflammatory bowel disease," *Clin Gastroenterol Hepatol.*, 5(3):339-344 (2007).
Rohlke et al., "Fecal flora reconstitution for recurrent Clostridium difficile infection: results and methodology," *J Clin Gastroenterol.*, 44(8):567-570 (2010).
Rolfe et al., "Bacterial interference between Clostridium difficile and normal fecal flora," *J Infect Dis.*, 143(3):470-475 (1981).
Rossen et al., "Findings From a Randomized Controlled Trial of Fecal Transplantation for Patients with Ulcerative Colitis," Gastroenterology, 149(1):110-8 (2015).
Round et al., "Inducible Foxp3+ regulatory T-cell development by a commensal bacterium of the intestinal microbiota," *PNAS*, 107(27):12204-12209 (2010).
Round et al., "The gut microbiota shapes intestinal immune responses during health and disease," *Nat. Rev. Immunol.*, 9(5):313-323 (2009).
Rupnik et al., "Clostridium difficile infection: new developments in epidemiology and pathogenesis," *Nat. Rev. Microbial.*, 7(7):526-536 (2009).
Russell et al., "Fecal bacteriotherapy for relapsing Clostridium difficile infection in a child: a proposed treatment protocol," *Pediatrics*, 126(1):e239-42 (2010).
Sambol et al., "Colonization for the prevention of *Clostridium difficile* disease in hamsters," *J Infect. Dis.*, 186(12):1781-1789 (2002).
Sanchez et al., "The Role of Natural Regulatory T cells in Infection," *Immunol Res.*, 49(0):124-134 (2011).
Sandler et al., "Possible Gut-Brain Interaction Contributing to Delayed Onset Autism Symptomatology," Fourth Int. Symp. Brain-Gut Interactions, Blackwell Science Ltd., 10(4):33 (1998).
Sandler et al., "Short-Term Benefit From Oral Vancomycin Treatment of Regressive-Onset Autism," Journal of Child Neurology, 15(7):429-435 (2000).
Sartor, "Therapeutic correction of bacterial dysbiosis discovered by molecular techniques," *PNAS*, 105(43):16413-16414 (2008).
Schiller, "Review article, the therapy of constipation," Ailment Pharmacol. Ther., 15:749-763 (2001).
Schloss, "Introducing mothur: Open-Source, Platform-Independent, Community-Supported Software for Describing and Comparing Microbial Communities," *Appl. Environ. Microbial.*, 75(23):7537-7541 (2009).
Schwan et al., "Relapsing *Clostridium difficile* Enterocolitis Cured by Rectal Infusion of Homologous Faeces," *The Lancet*, 322(8354):845 (1983).
Schwan et al., "Relapsing *Clostridium difficile* Enterocolitis Cured by Rectal Infusion of Normal Faeces," *Scand. J Infect. Dis.*, 16(2):211-215 (1984).
Seeff et al., "How many endoscopies are performed for colorectal cancer screening? Results from CDC's survey of endoscopic capacity," *Gastroenterology*, 127:1670-1677 (2004).
Sekirov et al., "Gut microbiota in health and disease," *Physiol. Rev.*, 90(3):859-904 (2010).
Sell et al., "Bacteriophage and Bacteriocin Typing Scheme for Clostridium difficile," Journal of Clinical Microbiology, 17(6):1148-1152 (1983).
Setlow, "I Will Survive: Protecting and Repairing Spore DNA," Journal of Bacteriology, 174(9):2737-2741 (1992).
Setlow, "The bacterial spore: nature's survival package," Culture, 26(2):1-4 (2005).
Sghir et al., "Quantification of Bacterial Groups within Human Fecal Flora by Oligonucleotide Prode Hybridization," *Applied and Environmental Microbiology*, 66(5):2263-2266 (2000).
Shi et al., "Fecal Microbiota Transplantation for Ulcerative Colitis: A Systematic Review and Meta-Analysis," PLOS One, 1-18 (2016).
Shim et al., "Primary symptomless colonisation by *Clostridium difficile* and decreased risk of subsequent diarrhea," *The Lancet*, 351(9103):633-666 (1998).
Silverman et al., "Success of self-administered home fecal transplantation for chronic Clostridium difficile infection," *Clin. Gastroenterol. Hepatol.*, 8(5):471-473 (2010)
Simor et al., "Clostridium difficile in long-term-care facilities for the elderly," *Infect Control Hosp Epidemiol.*, 23(11):696-703 (2002).
Singh et al., "Do NSAIDs, antibiotics, infections, or stress trigger flares in IBD?" *Am J Gastroenterol.*, 104(5): 1298-1313 (2009).
Sleator, "The human superorganism—of microbes and men," *Med. Hypotheses*, 74(2):214-215 (2010).
Smits et al., "Therapeutic potential of fecal microbiota transplantation," Gastroenterology, 145:946-953 (2013).
Sokol et al., *Faecalibacterium prausnitzii* is an anti-inflammatory commensal bacterium identified by gut microbiota analysis of Crohn disease patients, *Proceedings of the National Academy of Sciences*, 105(43):16731-16736 (2008).
Sokol et al., "Low Counts of *Faecalibacterium prausnitzii* in Colitis Microbiota," *Injlamm. Bowel Dis.*, pp. 1-7 (2009).
Sullivan et al., "Effect of supplement with lactic-acid producing bacteria on fatigue and physical activity inpatients with chronic fatigue syndrome," Nutritional Journal, 8(4):1-6 (2009).
Sunil et al., "Design and evaluation of lomoxicam bilayered tablets for biphasic release," Brazilian Journal of Pharmaceutical Sciences, 48(4):609-19 (2012).
Surawicz et al., "Treatment of refractory and recurrent Clostridium difficile infection," *Nat. Rev. Gastroenterol. Hepatol.*, 8(6):330-339 (2011).
Surawicz, "Reining in Recurrent Clostridium difficile Infection—Who's at Risk?," *Gastroenterology*, 136:1152-1154 (2009).
Sutherland et al., "Lyophilized Clostridium perfringens 3 alpha- and Clostridium bifermentans 7 alpha-hydroxysteroid dehydrogenases: two new stable enzyme preparations for routine bile acid analysis," Biochim Biophys Acta, 962(1):116-121 (1988).
Takaishi et al., "Imbalance in intestinal microflora constitution could be involved in the pathogenesis of inflammatory bowel disease," *J. Med. Microbial.*, 298:463-472 (2008).
Takeda et al., "Serum Haloperidol Levels of Schizophrenics Receiving Treatment for Tuberculosis," Clinical Neuropharmacology, 9(4):386-397 (1986).
Tannock et al., "A new macrocyclic antibiotic, fidaxomicin (OPT-80), causes less alteration to the bowel microbiota of Clostridium difficile-infected patients than does vancomycin," *Microbiology*, 156(11):3354-3359 (2010).

(56) References Cited

OTHER PUBLICATIONS

Tanoue et al., "Immune response to gut microbiota-commensals and pathogens," Gut Microbes, 1(4):224-233 (2010).
Taras et al., "Reclassification of Eubacterium formicigenerans Holdeman and Moore 1974 as Dorea formicigenerans gen. nov., comb. nov., and description of*Dorea longicatena* sp. nov., isolated from human faeces," *International Journal of Systematic and Evolutionary Microbiology*, 52:423-428 (2002).
Teasley et al., "Prospective randomised trial of metronidazole versus vancomycin for Clostridium-difficile-associated diarrhoea and colitis," *The Lancet*, 2(8358):1043-1046 (1983).
Tian et al., "Freeze-dried, Capsulized Fecal Microbiota Transplanation for Relapsing Clostridium difficile Infection," Journal of Clinical Gastroenterology, 49(6):537-538 (2015).
Tilg et al., "Gut microbiome, obesity, and metabolic dysfunction," *J Clin. Invest.*, 121(6):2126-2132 (2011).
Tvede et al., "Bacteriotherapy for chronic relapsing Clostridium difficile diarrhea in six patients," *The Lancet*, 1:1156-1160 (1989).
Van Andel et al., "Interleukin-12 Has a Role in Mediating Resistance of Murine Strains to Tyzzer's Disease," Infect. Immun., 66(10):4942-4946 (1998).
Van der Waaij et al., "Direct Flow Cytometry of Anaerobic Bacteria in Human Feces," *Cytometry*, 16:270-279 (1994).
Van Immerseel et al., "Butyric acid-producing anaerobic bacteria as a novel probiotic treatment approach for inflammatory bowel disease," *Journal of Medical Microbiology*, 59:141-143 (2010).
Van Nood et al., "Struggling with Recurrent Clostridium difficile Infections: Is Donor Faeces the Solution?," *Euro Surveill.*, 14(34):1-6 (2009).
Van Nood, "Duodenal infusion of donor feces for recurrent Clostridium difficile," *New England Journal of Medicine*, 368(5):407-415 (2013).
Vaughn et al., "Novel treatment options for ulcerative colitis," *Future Science*, 1-20 (2013).
Veldhuyzen van Zanten et al., "Drug Treatment of Functional Dyspepsia: A Systematic Analysis of Trial Methodology with Recommendations for Design of Future Trials," *Am. J Gastroenterol.*, 91(4):660-673 (1996).
Veldhuyzen van Zanten et al., "Validation of a 7-point Global Overall Symptom scale to measure the severity of dyspepsia symptoms in clinical trials," *Ailment Pharmacol. Ther.*, 23(4):521-529 (2006).
Venugopal et al., "Fidaxomicin: A Novel Macrocyclic Antibiotic Approved for Treatment of Clostridium difficile Infection," *Clin Infect Dis*, 54(4):568-74 (2012).
Vrieze et al., "The environment within: how gut microbiota may influence metabolism and body composition," *Diabetologia*, 53(4):606-613 (2010).
Vulevic et al., "Modulation of the fecal microflora profile and immune function by a novel trans-galactooligosaccharide mixture (B-GOS) in healthy elderly volunteers," Am J Clin Nutr, 88:1438-46 (2008).
Wachsmann et al., "Characterization of an Orotic Acid Fermenting Bacterium, *Zymobacterium oroticum*, nov. gen., nov. spec.," *Journal of Bacteriology*, 68(4):400-404 (1954).
Walter et al., "Host-microbial symbiosis in the vertebrate gastrointestinal tract and the Lactobacillus reuteri paradigm," PNAS USA, 108(Suppl 1):4645-4652 (2011).
Warny et al., "Toxin production by an emerging strain of Clostridium difficile associated with outbreaks of severe disease in North America and Europe," Lancet, 366(9491):1079-84 (2005).
Warren et al., "*Clostridium aldenense* sp. nov. and *Clostridium citroniae* sp. nov. Isolated from Human Clinical Infections," *Journal of Clinical Microbiology*, 44(7):2416-2422 (2006).

Wasfy et al., "Comparison of Preservation Media for Storage of Stool Samples," Journal of Clinical Microbiology, 33(8):2176-2178 (1995).
Weingarden et al., "Dynamic changes in short- and long-term bacterial composition following fecal microbiota transplantation for recurrent Clostridium difficile infection," Microbiome, 3(10), 8 pages (2015).
Weissman et al., "Stool Transplants: Ready for Prime Time?," Current Gastroenterology Reports, 14:313-316 (2012).
Wells et al., "Clostridia: Sporeforming Anaerobic Bacilli," *Medical Microbiology—NCBI Bookshelf*, 4th Edition, Chapter 18, pp. 1-20 (1996) <https://www.ncbi.nlm.nih.gov/books/NBK8219/?report=printable>.
Wenisch et al., "Comparison of Vancomycin, Teicoplanin, Metronidazole, and Fusidic Acid for the Treatment of Clostridium difficile-Associated Diarrhea," *Clin Infect Dis.*, 22(5):813-818 (1996).
Wettstein et al., "Fecal Bacteriotherapy—An effective Treatment for Relapsing Symptomatic Clostridium difficile Infection," Abstract,European 15th United Gastroenterology Week (UEGW) Poster presentations, United European Gastroenterology Federation, France, A303 (2007).
Wettstein et al., "Skewered diverticulum: another cause of abdominal pain," *Internal MedJ*, 31(8):495-496 (2001).
Wikoff et al., "Metabolomics analysis reveals large effects of gut microflora on mammalian blood metabolites," *PNAS*, 106(10):3698-3703 (2009).
Wilson et al., "Human Colonic Biota Studied by Ribosomal DNA Sequence Analysis," *Appl. Environ. Microbial.*, 62(7):2273-2278 (1996).
Yoon et al., "Treatment of Refractory/Recurrent C. difficile-associated Disease by Donated Stool Transplanted via Colonoscopy: A Case Series of 12 patients," *J Clin Gastroenterol.*, 44(8):562-566 (2010).
You et al., "Successful treatment of fulminant Clostridium difficile infection with fecal bacteriotherapy," *Ann. Intern. Med.*, 148(8):632-633 (2008).
Youngster et al., "Oral, Capsulized, Frozen Microbiota Transplantation for Relapsing Clostridium difficile Infection," *American Medical Association*, 312 (174) 1772-1778 (2014).
Yue et al., "Similarity Measure Based on Species Proportions," *Commun. Stat. Theor. Methods*, 34(11):2123-2131 (2005).
Zar et al., "A Comparison of Vancomycin and Metronidazole for the Treatment of Clostridium difficile-Associated Diarrhea, Stratified by Disease Severity," *Clin Infect Dis.*, 45(3):302-307 (2007).
Zhang et al, "Influence of Microbiota on Intestinal Immune System in Ulcerative Colitis and Its Intervention," Frontiers in Immunology, 8(Article 1674):1-11 (2017).
Zhang et al., "Altered gut microbiome composition in children with refractory epilepsy after ketogenic diet," *Epilepsy Research* (2018) <https://doi.org/10.1016/j.eplepsyres.2018.06.15>.
Zhou et al., "Total fecal microbiota transplantation alleviates high-fat diet-induced steatohepatitis in mice via beneficial regulation of gut microbiota," *Scientific Reports (Nature)*, 7(1529):1-11 (2017).
Zilberberg et al., "Clostridium difficile Infections amoung Hospitalized Children," Emerg. Infect. Dis, 16(4):604-609 (2010).
Zilberberg et al., "Clostridium difficile-related Hospitalizations amoung US Adults," Emerg. Infect. Dis, 15(1):122-124 (2009).
Zilberberg et al., "Increase in Adult Clostridium difficile-related Hospitalization and Case-Fatality Rate," Emerg. Infect. Dis, 14(6):929-931 (2008).
Zilberberg et al., "Increase in Clostridium difficile-related Hospitalizations Amoung Infants in the United States, 2001-2005" Pediatr Infect Dis. J, 27(12):1111-1113 (2008).
Zoppi et al., "Oral Bacteriotherapy in Clinical Practice," Eur J. Pediatr, 139(1):18-21 (1982).
Zoppi et al., "The Intenstinal Ecosystem in Chronic Functional Constipation," ACTA Paediatr, 836-841 (1998).

METHODS AND COMPOSITIONS FOR TREATING ULCERATIVE COLITIS

CROSS-REFERENCE TO RELATED APPLICATIONS

This application claims the benefit of U.S. Provisional Application Ser. Nos. 62/697,796 and 62/697,810, both filed Jul. 13, 2018, both of which are incorporated herein by reference in their entirety.

FIELD

The present disclosure includes and relates to methods and pharmaceutical compositions suitable for treating ulcerative colitis in a subject in need thereof.

BACKGROUND

Mammals harbor diverse microbial species in their gastrointestinal (GI) tracts. Interactions between these microbes and between microbes and the host, e.g. the host immune system, shape a microbiota. A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. An unbalanced microbiota (also called 'dysbiosis' or disrupted symbiosis) may lose its function and results in increased susceptibility to pathogens, altered metabolic profiles, or induction of proinflammatory signals that can lead to local or systemic inflammation or autoimmunity. The intestinal microbiota play a role in the pathogenesis of many disorders such as pathogenic infections of the gut.

Ulcerative colitis (UC) is a chronic disease of the large intestine, also known as the colon, in which the lining of the colon becomes inflamed and develops tiny open sores, or ulcers, that produce pus and mucous. Ulcerative colitis occurs most often in people ages 15 to 30, although the disease may afflict people of any age. It affects men and women equally and appears to run in some families.

Ulcerative colitis is a disease that is characterized by inflammation and micro-ulcers in the superficial layers of the large intestine. The inflammation usually occurs in the rectum and lower part of the colon, but it may affect the entire large intestine (pancolitis). Ulcerative colitis can very rarely affect the small intestine in its distal portion (Backwash Ileitis).

The inflammation is accompanied usually with diarrhea, which may be profuse and bloody. Micro-ulcers form in places where inflammation has destroyed the cells lining the bowel and these areas bleed and produce pus and mucus. Ulcerative colitis, especially when mild, can be difficult to diagnose because symptoms are similar to other intestinal disorders, most notably the other type of Irritable Bowel Diseases (IBD) called Crohn's disease and also irritable bowel syndrome. Crohn's disease differs from ulcerative colitis because it causes inflammation throughout the whole thickness of the intestinal wall and produces deep ulcers. Crohn's disease usually occurs in the small intestine, but it can also occur in the large intestine, anus, esophagus, stomach, appendix and mouth. Crohn's disease causes fistulae whereas ulcerative colitis does not. Both Crohn's and ulcerative colitis may co-exist in the same patient. The combination of inflammation and ulceration can cause abdominal discomfort and frequent emptying of the colon.

Existing treatments for ulcerative colitis involve intense and lengthy combinational drug therapy with side effects or even require surgery to remove part of the colon. Moreover, a substantial proportion of ulcerative colitis patients are resistant to standard drug therapy. Thus, there is a need for more effective treatments for ulcerative colitis that are easier to administer.

SUMMARY

The present disclosure provides methods and compositions for treating or preventing ulcerative colitis.

In an aspect, this application provides a pharmaceutical composition comprising viable non-pathogenic bacteria from one or more first microbial taxa selected from the group consisting of *Clostridium* cluster XVIII, *Ruminococcus, Lachnospiraceae, Roseburia, Eubacterium hallii*, and any combination thereof, wherein the pharmaceutical composition contains no bacteria from one or more second microbial taxa selected from the group consisting of *Fusobacterium, Sutterella, Haemophilus, Escherichia, Megamonas, Clostridium* cluster XIVa, *Prevotella, Dialister, Veillonella*, and *Bilophila*.

In an aspect, this application provides a pharmaceutical composition comprising a substantially entire fecal microbiota supplemented, enhanced, or spiked with viable non-pathogenic bacteria from one or more microbial taxa selected from the group consisting of *Clostridium* cluster XVIII, *Ruminococcus, Lachnospiraceae, Roseburia*, and *Eubacterium hallii*.

In an aspect, this application provides a pharmaceutical composition comprising a substantially entire fecal microbiota supplemented, enhanced, or spiked with viable non-pathogenic bacteria from a microbial taxon selected from the group consisting of *Bacteroides* OTU187, *Bacteroides fragilis*, and *Bacteroides finegoldii*.

In an aspect, this application provides a pharmaceutical composition comprising a fecal microbiota preparation having a suppressed, decreased, reduced, minimized, or undetectable level of a microbial taxon selected from the group consisting of *Clostridium* cluster XIVa (OTU173), *Streptococcus* (OTU56), *Sutterella wadsworthensis, Bacteroides uniformis*, and *Bacteroides coprocola*.

In an aspect, this application provides a method for treating ulcerative colitis (UC) in a patient in need thereof, the method comprising administering to the patient a pharmaceutical composition described here.

In an aspect, this application provides a method for treating UC in a patient in need thereof, comprising administering a pharmaceutical composition disclosed here to the patient, wherein the patient is pretested for one or more markers from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, heme biosynthesis, lipopolysaccharide biosynthesis, ubiquinone and other terpenoid quinine biosynthesis, lysine biosynthesis, and oxidative phosphorylation pathway.

In an aspect, this application provides a method for treating UC in a patient in need thereof, comprising administering a pharmaceutical composition disclosed here to the patient, wherein the patient is pretested for the relative abundance of *Fusobacterium gonidiaformans, Prevotella copri, Sutterella wadsworthensis*, or any combination thereof.

In an aspect, this application provides a method for treating UC in a patient in need thereof, comprising administering a pharmaceutical composition disclosed here to the patient, wherein the patient comprises a relative abundance of *Fusobacterium gonidiaformans, Prevotella copri*, or *Sutterella wadsworthensis* below a pre-determined highest limit.

In an aspect, this application provides a method for treating UC in a patient in need thereof, comprising administering a pharmaceutical composition disclosed here to the patient, wherein the patient comprises a relative abundance of one or more microbial taxa selected from the group consisting of *Fusobacterium, Sutterella, Haemophilus, Escherichia, Megamonas, Clostridium* cluster XIVa, *Prevotella, Dialister, Veillonella*, and *Bilophila*, below a pre-determined highest limit.

DETAILED DESCRIPTION

A randomised controlled study (ClinicalTrials.gov: NCT01896635) shows that multi-donor FMT therapy for active UC is significantly superior to placebo with 27% of patients achieving the primary endpoint of clinical remission with endoscopic remission or response compared to 7.5% with placebo, and more than half of patients on active treatment gaining a clinical response. Here, Applicant provides bacterial taxonomic and functional changes associated with FMT in UC, particularly those predictive of therapeutic success or failure. Applicant further illustrates underlying microbial basis, predictors of therapeutic outcome and the active constituent(s) of FMT mediating benefit.

Before the present compositions and methods are described, it is to be understood that the present disclosure is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular aspects of the disclosure, and not to exhaustively specify all permutations, combinations and variations thereof.

Unless defined otherwise herein, terms are to be understood according to conventional usage by those of ordinary skill in the relevant art. The terminology used in the description of the disclosure herein is for the purpose of describing particular embodiments only and is not intended to be limiting of the disclosure.

All publications, patent applications, patents and other references cited herein are incorporated by reference in their entireties.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

Methods disclosed herein can comprise one or more steps or actions for achieving the described method. The method steps and/or actions may be interchanged with one another without departing from the scope of the present invention. In other words, unless a specific order of steps or actions is required for proper operation of the embodiment, the order and/or use of specific steps and/or actions may be modified without departing from the scope of the present invention.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a percentages, density, volume and the like, is meant to encompass variations of 20%, 10%, 5%, 1%, 0.5%, or even 0.1% of the specified amount.

As used herein, the term "substantially", when used to modify a quality, generally allows certain degree of variation without that quality being lost. For example, in certain aspects such degree of variation can be less than 0.1%, about 0.1%, about 0.2%, about 0.3%, about 0.4%, about 0.5%, about 0.6%, about 0.7%, about 0.8%, about 0.9%, about 1%, between 1-2%, between 2-3%, between 3-4%, between 4-5%, or greater than 5%.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, a "taxon" refers to a particular taxonomic grouping, e.g., a particular species, genus, family, order, class, or phylum. The plural form of "taxon" is "taxa".

As used herein, a "subtaxon" refers to a taxonomic grouping at a lower level relative to and encompassed by a reference taxon. For example, all the subspecies, species, and genera within a taxon of particular family would be considered as a subtaxon of that family. The plural form of "subtaxon" is "subtaxa".

In an aspect, a marker for a pathway or a taxon (e.g., a metabolic pathway biomarker or a microbial biomarker) comprises a nucleic acid molecule, a peptide, a protein, a metabolite, a small molecule, a macromolecule, a secreted molecule, or a combination of any of the foregoing. In another aspect, a marker for a taxon comprises a 16S rDNA molecule or a 16S rRNA molecule. A marker can be identified or characterized using many methods such as those for characterizing nucleic acid and/or proteins. Nucleic acid analysis includes analysis of, for example, DNA, RNA, mRNA, rRNA, and/or tRNA, and can be accomplished using, for example, pyrosequencing, qPCR, RT-qPCR, clone libraries, denaturing gradient gel electrophoresis (DGGE), Terminal restriction fragment length polymorphism (T-RFLP), automated ribosomal intergenic spacer analysis (ARISA), microarrays, fluorescence in situ hybridization (FISH), dot-blot hybridization, next generation sequencing, and any other DNA hybridization methods that will detect a specific sequence. Protein analysis includes, for example, 2-Dimensional Gel Electrophoresis, 2-Diminsional Difference Gel Electrophoresis (2D-DIGE), MALDI TOF-MS, (2D-) LC-ESI-MS/MS, absolute quantification (AQUA), and isobaric tags for relative and absolute quantitation (iTRAQ).

In an aspect, a marker for a metabolic pathway comprises a RNA transcript molecule or a DNA molecule encoding an enzymatic polypeptide (or fragment thereof) from the metabolic pathway. In another aspect, a marker for a metabolic pathway comprises an enzymatic polypeptide (or fragment thereof) from the metabolic pathway. In an aspect, a marker for a metabolic pathway comprises an intermediary of the metabolic pathway. In an aspect, a marker for a metabolic pathway comprises the product of the metabolic pathway. For example, a marker for short chain fatty acid biosynthesis can include one or more short chain fatty acids.

As used herein, a "short chain fatty acid" or "SCFA" refers to fatty acids with an aliphatic tail of one to six carbon atoms. SCFAs can be produced by bacteria during bacterial metabolism, such as during fermentation of, for example, carbohydrates, proteins, peptides and glycoprotein precursors. Illustrative SCFAs include, but are not limited to, acetic acid (also known as acetate), butyric acid (also known as butyrate), caproic acid (also known as hexanoic acid), formic acid (also known as methanoic acid), heptanoic acid (also known as enanthic acid), isobutyric acid (also known as 2-methylpropanoic acid), isocaproic acid (also known as 4-methylpentanoic acid or 4-methylvaleric acid), isovaleric acid (also known as 3-methylbutanoic acid or β-methylbutyric acid), propionic acid (also known as propanoic acid), and valeric acid (also known as pentanoic acid).

As used herein, a "bile acid" refers to hydroxylated steroids synthesized from cholesterol in the liver, to break down fats. Examples of bile acids are cholic acid and chenodeoxycholic acid. Bile acids are conjugated with glycine or taurine prior to secretion into the bile. There are at least five major bile acid forms. Bile acids can be modified by intestinal bacteria. For example, primary bile acids are converted to secondary bile acids by dehydroxylation. Examples of secondary bile acids include lithocholic acid, deoxycholic acid, and ursodeoxycholic acid. Bile acids are reabsorbed by the entero-hepatic transport system and returned to the liver or excreted in feces. (Banerjee, A. Gastrointestinal toxicity biomarkers, *Biomarkers in Toxicology*, (2014)). Additional examples of bile acids are glycocholic acid, glycohenodeoxycholic acid, taurocholic acid, and taurochenodeoxycholic acid.

As used herein, "relative abundance" of a taxon within a community refers to the abundance of one taxon in comparison to other taxa present in that community, and reflects the evenness of distribution of individuals among a community. Example 1 provides an exemplary way of determining the relative abundance of a taxon of interest based on the number of 16S rDNA sequencing reads assigned to that taxon relative to the overall number of 16S rDNA sequencing reads from all microbes present in a community.

As used herein, "relative fecal abundance" refers to the relative abundance of a molecule or entity in a feces.

As used herein, "relative abundance ratio" refers to the ratio between the relative abundance of two or more taxa in comparison.

As used herein, the term "treating" refers to (i) completely or partially inhibiting a disease, disorder or condition, for example, arresting its development; (ii) completely or partially relieving a disease, disorder or condition, for example, causing regression of the disease, disorder and/or condition; or (iii) completely or partially preventing a disease, disorder or condition from occurring in a patient that may be predisposed to the disease, disorder and/or condition, but has not yet been diagnosed as having it. Similarly, "treatment" refers to both therapeutic treatment and prophylactic or preventative measures.

As used herein, a "therapeutically effective amount" or "pharmaceutically active dose" refers to an amount of a composition which is effective in treating the named disease, disorder or condition.

As used herein, "microbiota" refers to a community of microbes that viable in or on a patient's body, both sustainably and transiently, including eukaryotes, archaea, bacteria, and viruses (including bacterial viruses (i.e., phage)). A non-selected fecal microbiota refers to a community or mixture of fecal microbes derived from a donor's fecal sample without selection and substantially resembling microbial constituents and population structures found in such fecal sample.

As used herein, "remission rate," "cure rate," or "resolution rate" refers to the percentage of patients that are cured or obtain remission or complete resolution of a condition in response to a given treatment. As used herein, "clinical remission sustaining rate" refers to the percentage of patients remaining in clinical remission after a specified post-treatment period among all patients who achieve remission at the completion of a treatment. Quantitatively, remission, cure, or resolution is achieved when a patient's UCDAI score is below or equal to 2, assessed after 8 weeks of treatment. Remission, cure, or resolution can be further confirmed by endoscopic and mucosal healing.

As used herein, "primary outcome rate" refers to the percentage of patients achieving primary outcome after a specific treatment or treatment regimen among all patients receiving that treatment or treatment regimen.

As used herein, "response rate" refers to the percentage of patients that respond positively to a given treatment. Quantitatively, a patient responds to a treatment positively when the patient's UCDAI score decreases by at least 2 from baseline to week 8.

As used herein, "Mayo Clinic score" or "Mayo score" refers to an index system for assessing the severity of a ulcerative colitis disease condition. See Table 1 and Schoeder et al. N Engl J Med 1987; 317:1625-9. The Mayo Clinic score ranges from 0-12, with sub-scores of 0-3, where the higher scores indicate more severe disease. In an aspect, sub-scores may be rated for stool frequency, rectal bleeding, mucosal appearance at endoscopy, and physician's global assessment (PGA).

TABLE 1

Mayo Clinic Scoring System for Assessment of Ulcerative Colitis Activity (Schoeder et al. N Engl J Med 1987; 317: 1625-9)

| | score assignment |
|---|---|
| 1. Stool frequency* | |
| Normal number of stools for this patient | 0 |
| 1-2 stools more than normal | 1 |
| 3-4 stools more than normal | 2 |
| 5 or more stools more than normal | 3 |
| 2. Rectal Bleeding† | |
| No blood seen | 0 |
| Streaks of blood with stool less half the time | 1 |
| Obvious blood with stool most of the time | 2 |
| Blood alone passed | 3 |

TABLE 1-continued

Mayo Clinic Scoring System for Assessment of Ulcerative Colitis
Activity (Schoeder et al. N Engl J Med 1987; 317: 1625-9)

| | score assignment |
|---|---|
| 3. Findings of flexible proctosigmoidoscopy | |
| Normal or inactive disease | 0 |
| Mild disease (erythema, decreased vascular pattern, mild friability) | 1 |
| Moderate disease (marked erythema, absent vascular pattern, friability, erosions) | 2 |
| Severe disease (spontaneous bleeding, ulceration) | 3 |
| 4. Physician's global assessment‡ | |
| Normal | 0 |
| Mild disease | 1 |
| Moderate disease | 2 |
| Severe disease | 3 |

*Each patient served as his or her own control to establish the degree of abnormality of the stool frequency
†The daily bleeding score represented the most severe bleeding of the day
‡The physician's global assessment acknowledged the three other criteria, the patient's daily record of abdominal discomfort and general sense of well-being, and other observations, such as physical findings and the patient's performance status As used herein, "ulcerative colitis endoscopic index of severity" or "UCEIS" refers to an index for assessing endoscopic disease activity. The index assesses three criteria, including vascular pattern, bleeding, and erosions and ulcers (Table 2). See Travis et al., Developing an instrument to assess the endoscopic severity of ulcerative colitis: the Ulcerative Colitis Endoscopic Index of Severity (UCEIS), Gut 2012, 61(4): 535-42. A higher score reflects increased disease severity.

TABLE 2

Scoring System for Ulcerative Colitis Endoscopic
Index of Severity (See Travis et al.)

| | score assignment |
|---|---|
| 1. Vascular pattern | |
| Normal: Normal vascular pattern with arborization of capillaries clearly defined, or with blurring or patchy loss of capillary margins | 1 |
| Patchy obliteration: Patchy obliteration of vascular pattern | 2 |
| Obliterated: Complete obliteration of vascular pattern | 3 |
| 2. Rectal bleeding | |
| None: No visible blood | 1 |
| Mucosal: Some spots or streaks of coagulated blood on the surface of the mucosa ahead of the scope, which can be washed away | 2 |
| Luminal mild: Some free liquid blood in the lumen | 3 |
| Luminal moderate or severe: Frank blood in the lumen ahead of endoscope or visible oozing from mucosa after washing intra-luminal blood, or visible oozing from a hemorrhagic mucosa | 4 |
| 3. Erosions and ulcers | |
| None: Normal mucosa, nonvisible erosions or ulcers | 1 |
| Erosions: Tiny (≤5 mm) defects in the mucosa, of a white or yellow color with a flat edge | 2 |
| Superficial ulcer: Larger (>5 mm) defects in the mucosa, which are discrete fibrin-covered ulcers when compared to erosions, but remain superficial | 3 |
| Deep ulcer: Deeper excavated defects in the mucosa, with a slightly raised edge | 4 |

As used herein, "ulcerative colitis disease activity index" or "UCDAI" refers to an index system for assessing the symptomatic severity or response of a ulcerative colitis patient. The index assesses four variables, which include stool frequency, severity of bleeding, colonic mucosal appearance, and the physician's overall assessment of disease activity (Table 3). See Sutherland et al., 5-Aminosalicylic acid enema in the treatment of distal ulcerative colitis, proctosigmoiditis, and proctitis. Gastroenterology. 1987; 92:1 894-8. Each variable is scored from 0-3 so that the total index score ranges from 0-12; 0-2: remission; 3-6: mild; 7-10: moderate; >10: severe ulcerative colitis.

TABLE 3

Scoring System for Ulcerative Colitis Disease
Activity Index. (See Tursi et al.)

| | score assignment |
|---|---|
| 1. Stool frequency | |
| Normal | 0 |
| 1-2 Stools/day>normal | 1 |
| 3-4 Stools/day>normal | 2 |
| >4 Stools/day>normal | 3 |
| 2. Rectal bleeding | |
| None | 0 |
| Streaks of blood | 1 |
| Obvious blood | 2 |
| Mostly blood | 3 |
| 3. Mucosal appearance | |
| Normal | 0 |
| Mild friability | 1 |
| Moderate friability | 2 |
| Exudation, spontaneous bleeding | 3 |
| 4. Physician's rating of disease activity | |
| Normal | 0 |
| Mild | 1 |
| Moderate | 2 |
| Severe | 3 |

As used herein, "bacteria," "bacterium," and "archaea" refer to single-celled prokaryotes that lack membrane bound nuclei and lack organelles.

As used herein, "fecal bacteria" refers to bacteria that can be found in fecal matter.

As used herein, "viable" means possessing the ability to multiply.

As used herein, "isolated" or "purified" refers to a bacterium or other entity or substance that has been (1) separated from at least some of the components with which it was associated when initially produced (whether in nature or in an experimental setting), and/or (2) produced, prepared, purified, and/or manufactured by the hand of man. Isolated or purified bacteria can be separated from at least about 10%, about 20%, about 30%, about 40%, about 50%, about 60%, about 70%, about 80%, about 90%, or more of the other components with which they were initially associated.

As used herein, the terms "pathogen" and "pathogenic" in reference to a bacterium or any other organism or entity includes any such organism or entity that is capable of causing or affecting a disease, disorder or condition of a host organism containing the organism or entity.

As used herein, "spore" or a population of "spores" includes bacteria (or other single-celled organisms) that are generally viable, more resistant to environmental influences such as heat and bacteriocidal agents than vegetative forms of the same bacteria, and typically capable of germination and out-growth. "Spore-formers" or bacteria "capable of forming spores" are those bacteria containing the genes and other necessary abilities to produce spores under suitable environmental conditions.

As used herein, a "combination" of two or more bacteria includes the physical co-existence of the two bacteria, either in the same material or product or in physically connected products, as well as the temporal co-administration or co-localization of the two bacteria.

As used herein, a "subject" refers to a human. A subject may be healthy, or may be suffering from an infection due to a gastrointestinal pathogen or may be at risk of developing or transmitting to others an infection due to a gastrointestinal pathogen.

As used herein, "operational taxonomic unit" or "OTU" refers to a group of closely related microbial species determined based on 16S or 18S rRNA marker genes. As illustrated in Example 1, in an aspect, an OTU can share 97% similarity in 16S rRNA sequences based on a opti-clust average neighbour algorithm.

As used herein, an "intermittent dosing schedule" means that a pharmaceutical composition is administered for a period of time followed by a period of time (a treatment period) where treatment with such pharmaceutical composition is withheld (a rest period). Intermittent dosing regimens can be expressed as treatment period in days or weeks/rest period in days or weeks. For example, a 4/1 intermittent dosing schedule refers to an intermittent dosing schedule where the treatment period is four weeks/days and the rest period is one week/day.

As used herein, a "continuous dosing schedule" refers to a dosing schedule where a pharmaceutical composition is administered during a treatment period without a rest period. Throughout the treatment period of a continuous dosing schedule, a pharmaceutical composition can be administered, for example, daily, or every other day, or every third day. On a day when a pharmaceutical composition is administered, it can be administered in a single dose, or in multiple doses throughout the day.

As used herein, "dosing frequency" refers to the frequency of administering doses of a pharmaceutical composition in a given time. Dosing frequency can be indicated as the number of doses per a given time, for example, once per day, once a week, or once in two weeks.

As used herein, "dosing interval" refers to the amount of time that elapses between multiple doses being administered to a patient.

Different types of ulcerative colitis exist. As used herein, "ulcerative proctitis" refers to a disease form where bowel inflammation is limited to the rectum. Because of its limited extent (usually less than the six inches of the rectum), ulcerative proctitis tends to be a milder form of ulcerative colitis. It is associated with fewer complications and offers a better outlook than more widespread disease. For approximately 30% of all patients with ulcerative colitis, the illness begins as ulcerative proctitis.

As used herein, "proctosigmoiditis" refers to a form of colitis affecting the rectum and the sigmoid colon, the lower segment of colon located right above the rectum. Symptoms include bloody diarrhea, cramps, and a constant feeling of the need to pass stool, known as tenesmus. Moderate pain on the lower left side of the abdomen may occur in active disease.

As used herein, "left-sided colitis" refers to continuous inflammation that begins at the rectum and extends as far as a bend in the colon near the spleen called the splenic flexure. Symptoms include loss of appetite, weight loss, diarrhea, severe pain on the left side of the abdomen, and bleeding.

As used herein, "pan-ulcerative (total) colitis" affects the entire colon.

Symptoms include diarrhea, severe abdominal pain, cramps, and extensive weight loss. Potentially serious complications include massive bleeding and acute dilation of the colon (toxic megacolon), which may lead to an opening in the bowel wall. Serious complications may require surgery.

Several theories have been proposed for the cause of ulcerative colitis. There is some evidence to suggest that the body's immune system reacts to an environmental, dietary or infectious agent in genetically susceptible individuals causing inflammation in the intestinal wall. The latest postulated causal agent is the to be an infection of the lining with a *Fusobacterium varium* identified by researchers from Japan. Ulcerative colitis is not caused by emotional distress or sensitivity to certain foods or food products but these factors may trigger symptoms in some people. Ulcerative colitis is most likely not an aberrant reaction but an infection.

The most common symptoms of ulcerative colitis are bloody diarrhea and abdominal pain. Patients also may experience fever, rectal bleeding, fatigue, anaemia, loss of appetite, weight loss and loss of body fluids and nutrients resulting in nutritional deficiencies. These symptoms occur as intermittent attacks in between periods when the symptoms go away (remissions). These disease-free periods can last for months or even years. Usually an attack begins with increased urgency to defecate, mild lower abdominal cramps, and blood and mucus in the stools.

Ulcerative colitis may cause long-term problems such as arthritis, inflammation of the eye, liver disease (fatty liver, hepatitis, cirrhosis, and primary sclerosing cholangitis), osteoporosis, skin rashes, anaemia and kidney stones. These complications may occur when the immune system triggers inflammation in other parts of the body. These problems can disappear when the colitis is treated effectively.

Treatment for ulcerative colitis depends on the seriousness of the disease. Most people are treated with medication. Some people whose symptoms are triggered by certain foods are able to control the symptoms by avoiding foods that upset their intestines, like highly seasoned foods or dairy products. Each person may experience ulcerative colitis differently, so treatment is adjusted for each individual.

Many patients with mild or moderate disease are first treated with 5-ASA agents, including a combination of the drugs 5-aminosalicylic acids and sulfasalazine that helps control inflammation. Sulfasalazine is the most commonly used of these drugs. Sulfasalazine can be used for as long as needed and can be given along with other drugs. Patients who do not do well on sulfasalazine may respond to newer 5-ASA agents. Possible side effects of 5-ASA preparations include nausea, vomiting, heartburn, diarrhea and headache.

People with severe disease and those who do not respond to 5-ASA preparations may be treated with added corticosteroids. Prednisone and budesonide and hydrocortisone are corticosteroids used to reduce inflammation. They can be given orally, intravenously, through an enema, or in a suppository, depending on the location of the inflammation. Corticosteroids can cause side effects such as weight gain, acne, facial hair, hypertension, diabetes, mood swings, and increased risk of infection, so doctors carefully monitor patients taking these medications.

Immunosuppressants such as azathioprine, 6-mercaptopurine (6-MP) and methotrexate are often used and can make a marked improvement at a low dose with few side effects. Other drugs may be given to relax the patient or to relieve pain, diarrhea, or infection. Occasionally, symptoms are severe enough that the person must be hospitalized. For example, a person may have severe bleeding or severe diarrhea that causes dehydration. In such cases the doctor will try to stop diarrhea and loss of blood, fluids, and mineral salts. The patient may need a special diet, feeding through a vein, medications, or sometimes surgery.

In severe cases, a patient may need surgery to remove the diseased colon.

Sometimes the doctor will recommend removing the colon if medical treatment fails or if the side effects of corticosteroids or other drugs threaten the patient's health.

In an aspect, this application provides a microbial biomarker and its use for predicting the likelihood of a UC patient achieving a primary outcome using a fecal bacteria-based therapy. In an aspect, the disclosure provides a microbial taxon, or a subtaxon therein, in UC patients associated with UC treatment success, where the microbial taxon is selected from the group consisting of *Clostridium* cluster XVIII, *Ruminococcus, Lachnospiraceae, Roseburia inulinivorans*, and *Eubacterium hallii*.

In another aspect, this application provides a microbial biomarker and its use for screening a UC patient for the patient's suitability for a fecal bacteria-based therapy. In an aspect, this application provide a microbial taxon, or a subtaxon therein, in UC patients associated with lack of UC treatment success, where the microbial taxon is selected from the group consisting of *Fusobacterium, Sutterella, Haemophilus, Escherichia, Megamonas, Clostridium* cluster XIVa, *Prevotella, Dialister, Veillonella*, and *Bilophila*, or a subtaxon within the microbial taxon. In another aspect, this application provide a microbial taxon, or a subtaxon therein, in UC patients associated with lack of UC treatment success, where the microbial taxon is selected from the group *Fusobacterium gonidiaformans, Prevotella copri*, and *Sutterella wadsworthensis*.

In an aspect, this application provides a metabolic pathway biomarker and its use for predicting the likelihood of a UC patient achieving a primary outcome using a fecal bacteria-based therapy. In another aspect, a metabolic pathway biomarker associated with UC treatment success is selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, and starch degradation.

In an aspect, this application provides a metabolic pathway biomarker for predicting the likelihood of a UC patient not achieving a primary outcome using a fecal bacteria-based therapy. In another aspect, a metabolic pathway biomarker associated with UC treatment failure is selected from the group consisting of heme biosynthesis, lipopolysaccharide biosynthesis, ubiquinone and other terpenoid quinine biosynthesis, lysine biosynthesis and oxidative phosphorylation pathways.

In another aspect, this application provides a biomarker and its use for predicting the effectiveness of a donor fecal material for treating UC. In an aspect, a microbial taxon in donor fecal material associated with effective UC treatment is selected from the group consisting of *Bacteroides* OTU187, *Bacteroides fragilis*, and *Bacteroides finegoldii*. In another aspect, a microbial taxon in donor fecal material associated with ineffective UC treatment is selected from the group consisting of *Bacteroides uniformis, Bacteroides coprocola, Clostridium* cluster XIVa (OTU173), *Streptococcus* (OTU56), and *Sutterella wadsworthensis*. In an aspect, a metabolic pathway in donor fecal material associated with effective UC treatment is selected from the group consisting of fatty acid biosynthesis, propanoate metabolism, secondary bile acid biosynthesis, glycerophospholipid metabolism, and biosynthesis of ansamycins. In an aspect, a metabolic pathway in donor fecal material associated with ineffective UC treatment is selected from the group consisting of terpenoid backbone biosynthesis, bacterial chemotaxis, and heme biosynthesis.

In an aspect, a marker in a patient indicating positive primary outcome can also be a marker for selecting a successful source material from one or more donors. In an aspect, a successful source material is derived from one or more donors. In another aspect, a successful source material is synthetic.

In an aspect, this application provides a method for selecting a source material from a donor based on a biomarker. In an aspect the source material is derived from fecal microbiota from a donor. In another aspect, the source material is derived from the fecal microbiota of one or more donors. In yet another aspect, the source material is derived from the fecal microbiota of two or more, three or more, four or more, or five or more donors. In a further aspect, the source material is derived from the fecal microbiota of a donor related to or unrelated to the patient in need of the source material.

In an aspect a biomarker is one or more markers from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, heme biosynthesis, lipopolysaccharide biosynthesis, ubiquinone and other terpenoid quinine biosynthesis, lysine biosynthesis, and oxidative phosphorylation pathway. In another aspect, a biomarker is two or more markers from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, heme biosynthesis, lipopolysaccharide biosynthesis, ubiquinone and other terpenoid quinine biosynthesis, lysine biosynthesis, and oxidative phosphorylation pathway. In another aspect, a biomarker is three or more markers from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, heme biosynthesis, lipopolysaccharide biosynthesis, ubiquinone and other terpenoid quinine biosynthesis, lysine biosynthesis, and oxidative phosphorylation pathway. In a further aspect, a biomarker is four or more markers from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, heme biosynthesis, lipopolysaccharide biosynthesis, ubiquinone and other terpenoid quinine biosynthesis, lysine biosynthesis, and oxidative phosphorylation pathway. In another aspect, a biomarker is five or more markers from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, heme biosynthesis, lipopolysaccharide biosynthesis, ubiquinone and other terpenoid quinine biosynthesis, lysine biosynthesis, and oxidative phosphorylation pathway. In another aspect, a biomarker is six or more markers from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, heme biosynthesis, lipopolysaccharide biosynthesis, ubiquinone and other terpenoid quinine biosynthesis, lysine biosynthesis, and oxidative phosphorylation pathway. In another aspect, a biomarker is seven or more markers from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, heme biosynthesis, lipopolysaccharide biosynthesis, ubiquinone and other terpenoid quinine biosynthesis, lysine biosynthesis, and oxidative phosphorylation pathway. In another aspect, a biomarker is eight or more markers from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, heme biosynthesis, lipopolysaccharide biosynthesis, ubiquinone and other terpenoid quinine biosynthesis, lysine biosynthesis, and oxidative phosphorylation pathway. In another aspect, a biomarker is nine or more markers from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, heme biosynthesis, lipopolysaccharide biosynthesis, ubiquinone and other terpenoid quinine biosynthesis, lysine biosynthesis, and oxidative phosphorylation pathway. In another aspect, a biomarker is ten or more markers from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, heme biosynthesis, lipopolysaccharide biosynthesis, ubiquinone and other terpenoid quinine biosynthesis, lysine biosynthesis, and oxidative phosphorylation pathway. In another aspect, a biomarker is eleven or more markers from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, heme biosynthesis, lipopolysaccharide biosynthesis, ubiquinone and other terpenoid quinine biosynthesis, lysine biosynthesis, and oxidative phosphorylation pathway.

In an aspect, this application provides a microbial biomarker and its use for selecting a source material with predictive primary outcome of treatment success in a UC patient. In an aspect, the disclosure provides a microbial taxon, or a subtaxon therein, in a source material associated with UC treatment success, where the microbial taxon is selected from the group consisting of *Clostridium* cluster XVIII, *Ruminococcus, Lachnospiraceae, Roseburia inulinivorans*, and *Eubacterium hallii*.

In an aspect, this application provides a microbial biomarker and its use for selecting a source material with predictive primary outcome of treatment success in a fecal-based therapy in a UC patient. In another aspect, the microbial biomarker is a marker from the *Roseburia* genus. In another aspect the microbial biomarker is a Roseburia spp. selected from the group consisting of *R. inulinivorans, R. cecicola, R. faecis, R hominis,* and *R. intestinalis*. In another aspect, a microbial biomarker is *Roseburia faecis*.

In another aspect, this application provides a microbial biomarker and its use for screening a source material for suitability for a fecal bacteria-based therapy. In an aspect, this application provides a microbial taxon, or a subtaxon therein, in a source material associated with lack of UC treatment success, where the microbial taxon is selected from the group consisting of *Fusobacterium, Sutterella, Haemophilus, Escherichia, Megamonas, Clostridium* cluster XIVa, *Prevotella, Dialister, Veillonella,* and *Bilophila,* or a subtaxon within the microbial taxon. In another aspect, this application provide a microbial taxon, or a subtaxon therein, in a source material associated with lack of UC treatment success, where the microbial taxon is selected from the group *Fusobacterium gonidiaformans, Prevotella copri,* and *Sutterella wadsworthensis*.

In another aspect, this application provides a method for selecting a source material for suitability in a fecal bacteria-based therapy based on the small chain fatty acid content of the material.

In an aspect, a method for selecting a source material for suitability in a fecal bacteria-based therapy comprises selecting based on pyruvate fermentation to acetate and lactate. In another aspect, selection is based on specific bacterial functional pathways associated with primary outcome of patients treated with a fecal bacteria-based therapy. In another aspect, Benzoate degradation, glycerophospholipid metabolism, secondary bile acid biosynthesis, guanosine penta/tetraphosphate biosynthesis, pyruvate fermentation to acetate and lactate (short-chain fatty acid biosynthesis), biosynthesis of ansamycins, and starch degradation are associated with positive primary outcome.

In an aspect, a method for selecting a source material for suitability in a fecal bacteria-based therapy comprises selecting based taxa contributing to positive outcomes of patients treated with fecal bacteria-based therapy. In an aspect, source material for fecal bacteria-based therapy is selected from *Eubacterium, Ruminococcus, Lachnospiraceae, Roseburia, Dorea,* and *Coprococcus* species. In another aspect, source material for fecal bacteria-based therapy is selected based on two or more of *Eubacterium, Ruminococcus, Lachnospiraceae, Roseburia, Dorea,* and *Coprococcus* species. In another aspect, source material for fecal bacteria-based therapy is selected based on three or more of *Eubacterium, Ruminococcus, Lachnospiraceae, Roseburia, Dorea,* and *Coprococcus* species. In another aspect, source material for fecal bacteria-based therapy is selected based on three or more of *Eubacterium, Ruminococcus, Lachnospiraceae, Roseburia, Dorea,* and *Coprococcus* species. In yet another aspect, source material for fecal bacteria-based therapy is selected based on *Eubacterium, Ruminococcus, Lachnospiraceae, Roseburia, Dorea,* or *Coprococcus* species being present in a source material at a level higher than a predetermined level.

In an aspect, source material for fecal bacteria-based therapy is selected based on levels of taxa selected from the group consisting of *Eubacterium hallii, Roseburia inulivorans, Ruminococcus bromii*. In another aspect, source material is selected based on the levels of one or more *Eubacterium hallii, Roseburia inulivorans,* and *Ruminococcus bromii,* being above a pre-determined level. In another aspect, source material is selected based on the levels of two or more of *Eubacterium hallii*, *Roseburia inulivorans*, and *Ruminococcus bromii*, being above a pre-determined level. In another aspect, source material is selected based on the levels of *Eubacterium hallii*, *Roseburia inulivorans*, and *Ruminococcus bromii*, being above a pre-determined level.

In an aspect, this application provides a method for selecting a source material for suitability in a fecal bacteria-based therapy based on the level of *Bacteroides* in the source material. In an aspect, the level of *Bacteroides* in a source material selected for use in a fecal bacteria-based therapy is higher than a predetermined level.

In an aspect, this application provides a method for selecting a source material for suitability in a fecal bacteria-based therapy based on the level of Streptococcus species in the source material. In an aspect, the level of Streptococcus species in a source material selected for use in a fecal bacteria-based therapy is lower than a predetermined level.

In an aspect, this application provides a metabolic pathway biomarker and its use for predicting the likelihood of a source material achieving a primary outcome in a patient in need thereof. In another aspect, a metabolic pathway biomarker associated with predictive source material success is selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, and starch degradation.

In an aspect, this application provides a metabolic pathway biomarker for predicting treatment failure of a source material when used in a fecal bacteria-based therapy. In another aspect, a metabolic pathway biomarker associated with UC treatment failure is selected from the group consisting of heme biosynthesis, lipopolysaccharide biosynthesis, ubiquinone and other terpenoid quinine biosynthesis, lysine biosynthesis and oxidative phosphorylation pathways. In an aspect, this application provides for selection of a source material for use in a fecal bacteria-based therapy comprising selecting the source material with reduced metabolic pathway biomarkers for predicting treatment failure in patients.

In an aspect, this application provides a method for selecting a source material for a fecal bacteria-based therapy based on a reduced presence of biomarkers shown to indicate a lack of remission (or negative primary outcomes) in UC patients. In an aspect, microbial taxa associated with lack of remission are selected from *Fusobacterium*, *Sutterella*, *Haemophilus*, *Escherichia*, *Megamonas*, *Clostridium* XIVa, *Prevotalla*, *Dialister*, *Veillonella*, and *Bilophila*. In another aspect, *Fusobacterium gonidiaformans* and *Prevotella* OTU2 are associated with lack of remission. In yet another aspect, *Bacteroides uniformis* and *Bacteroides coprocola* are associated with lack of remission. In a further aspect, *Streptococcus* species (OTU56) is associated with lack of remission is a treated UC patient. In another aspect, heme biosynthesis is a marker for negative primary patent outcome.

In an aspect, this disclosure provides a method for treating UC by decreasing the relative abundance of *Bacteroides clarus* and/or *Akkermansia muciniphila*. In an aspect, this disclosure provides a method for treating UC by increasing the relative abundance of *Faecalibacterium prausnitzii*, *Eubacterium rectale*, and/or *Eubacterium siraeum*. In a further aspect, this disclosure provides a method for treating UC by administering to a patient a pharmaceutical composition comprising one or more viable bacteria selected from the group consisting of *Faecalibacterium prausnitzii*, *Eubacterium rectale*, and *Eubacterium siraeum*.

In an aspect, this application provides a pharmaceutical composition comprising viable non-pathogenic bacteria from one or more first microbial taxa selected from the group consisting of *Clostridium* cluster XVIII, *Ruminococcus*, *Lachnospiraceae*, *Roseburia inulinivorans*, *Eubacterium hallii*, and any combination thereof, wherein the pharmaceutical composition contains no bacteria from one or more second microbial taxa selected from the group consisting of Fusobacterium, *Sutterella*, *Haemophilus*, *Escherichia*, *Megamonas*, *Clostridium* cluster XIVa, *Prevotella*, *Dialister*, *Veillonella*, and *Bilophila*.

In another aspect, this application provides a pharmaceutical composition comprising viable non-pathogenic bacteria from one or more first microbial taxa selected from the group consisting of *Clostridium* cluster XVIII, *Ruminococcus*, *Lachnospiraceae*, *Roseburia inulinivorans*, and *Eubacterium hallii*, wherein the pharmaceutical composition contains no bacteria from a second microbial taxon selected from the group consisting of *Fusobacterium gonidiaformans*, *Prevotella copri*, and *Sutterella wadsworthensis*.

In an aspect, this application provides a pharmaceutical composition comprising a substantially entire fecal microbiota supplemented, enhanced, or spiked with viable non-pathogenic bacteria from one or more microbial taxa selected from the group consisting of *Clostridium* cluster XVIII, *Ruminococcus*, *Lachnospiraceae*, *Roseburia inulinivorans*, and *Eubacterium hallii*.

In an aspect, this application provides a pharmaceutical composition comprising a fecal microbe preparation having a relative abundance ratio of 2 or more between a first microbial taxon selected from the group consisting of *Clostridium* cluster XVIII, *Ruminococcus*, *Lachnospiraceae*, *Roseburia inulinivorans*, and *Eubacterium hallii*, and a second microbial taxon selected from the group consisting of *Fusobacterium*, *Sutterella*, *Haemophilus*, *Escherichia*, *Megamonas*, *Clostridium* cluster XIVa, *Prevotella*, *Dialister*, *Veillonella*, and *Bilophila*. In an aspect, a second microbial taxon is selected from the group consisting of *Fusobacterium gonidiaformans*, *Prevotella copri*, and *Sutterella wadsworthensis*. In another aspect, the relative abundance ratio between the first and second microbial taxa is selected from the group consisting of 3 or more, 4 or more, 5 or more, 10 or more, 20 or more, 30 or more, 50 or more, 100 or more, and 200 or more.

In an aspect, this application provides a pharmaceutical composition comprising a substantially entire fecal microbiota supplemented, enhanced, or spiked with viable non-pathogenic bacteria from a microbial taxon selected from the group consisting of *Bacteroides* OTU187, *Bacteroides fragilis*, and *Bacteroides finegoldii*.

In an aspect, this application provides a pharmaceutical composition comprising viable non-pathogenic bacteria from a first microbial taxon selected from the group consisting of *Bacteroides* OTU187, *Bacteroides fragilis*, and *Bacteroides finegoldii*. In another aspect, a pharmaceutical composition contains no bacteria from a second microbial taxon selected from the group consisting of *Fusobacterium gonidiaformans*, *Prevotella copri*, and *Sutterella wadsworthensis*. In a further aspect, a pharmaceutical composition contains no bacteria from a second microbial taxon selected from the group consisting of *Clostridium* cluster XIVa (OTU173), *Streptococcus* (OTU56), *Sutterella wadsworthensis*, *Bacteroides uniformis*, and *Bacteroides coprocola*.

In an aspect, this application provides a pharmaceutical composition comprising viable non-pathogenic bacteria from the *Roseburia* spp. In another aspect, a pharmaceutical composition comprises viable non-pathogenic bacteria selected from the group consisting of *R. inulinivorans, R. cecicola, R. faecis, R. hominis,* and *R. intestinalis*. In another aspect, a pharmaceutical composition comprises viable non-pathogenic *Roseburia faecis*.

In an aspect, this application provides a pharmaceutical composition comprising viable non-pathogenic bacteria from one or more first microbial taxa selected from the group consisting of *Clostridium* cluster XVIII, *Ruminococcus, Lachnospiraceae, Roseburia inulinovorans, Eubacterium hallii*, and any combination thereof, wherein the pharmaceutical composition contains no bacteria from one or more second microbial taxa selected from the group consisting of *Fusobacterium, Sutterella, Haemophilus, Escherichia, Megamonas, Clostridium* cluster XIVa, *Prevotella, Dialister, Veillonella*, and *Bilophila*.

In an aspect, this application provides a pharmaceutical composition comprising viable non-pathogenic bacteria from one or more first microbial taxa selected from the group consisting of *Clostridium* cluster XVIII, *Ruminococcus, Lachnospiraceae, Roseburia faecis, Eubacterium hallii*, and any combination thereof, wherein the pharmaceutical composition contains no bacteria from one or more second microbial taxa selected from the group consisting of *Fusobacterium, Sutterella, Haemophilus, Escherichia, Megamonas, Clostridium* cluster XIVa, *Prevotella, Dialister, Veillonella*, and *Bilophila*.

In an aspect, this application provides a pharmaceutical composition comprising a substantially entire fecal microbiota supplemented, enhanced, or spiked with viable non-pathogenic bacteria from one or more microbial taxa selected from the group consisting of *Clostridium* cluster XVIII, *Ruminococcus, Lachnospiraceae, Roseburia inulinivorans*, and *Eubacterium hallii*.

In an aspect, this application provides a pharmaceutical composition comprising a substantially entire fecal microbiota supplemented, enhanced, or spiked with viable non-pathogenic bacteria from one or more microbial taxa selected from the group consisting of *Clostridium* cluster XVIII, *Ruminococcus, Lachnospiraceae, Roseburia faecis*, and *Eubacterium hallii*.

In an aspect, a pharmaceutical composition comprises viable non-pathogenic bacteria or a fecal microbe preparation from a synthetic culture.

In an aspect, this application provides a pharmaceutical composition comprising a fecal microbiota preparation having a suppressed, decreased, reduced, minimized, or undetectable level of a microbial taxon selected from the group consisting of *Clostridium* cluster XIVa (OTU173), *Streptococcus* (OTU56), *Sutterella wadsworthensis, Bacteroides uniformis*, and *Bacteroides coprocola*. In an aspect, a microbial taxon is suppressed or decreased relative to the level of that taxon in a control fecal microbiota preparation. In an aspect, a microbial taxon is suppressed or decreased relative to the level of that taxon in a healthy adult donor fecal material. In an aspect, a microbial taxon is suppressed or decreased in a treated fecal donor-derived microbe preparation relative to the untreated source fecal material from the fecal donor. In another aspect, an antibiotic specific to a taxon or a heat, ethanol, or chloroform-based treatment is used to suppress or decrease that taxon. In an aspect, a fecal donor is screened for a reduced, minimized, or undetectable level of a microbial taxon mentioned in this paragraph. In another aspect, a synthetic fecal composition is provided with a lower level of a microbial taxon selected from the group consisting of *Clostridium* cluster XIVa (OTU173), *Streptococcus* (OTU56), *Sutterella wadsworthensis, Bacteroides uniformis*, and *Bacteroides coprocola*, relative to a fecal microbiota prepared from a healthy adult donor fecal material.

In an aspect, this application provides a method for treating ulcerative colitis (UC) in a patient in need thereof, the method comprising administering to the patient a pharmaceutical composition described here.

In an aspect, this application provides a method for modulating a metabolic marker from a pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, and starch degradation, in a UC patient in need thereof, the method comprising administering to the patient a pharmaceutical composition described here.

In an aspect, this application provides a method for treating UC in a patient in need thereof, comprising administering to the patient a modulator of a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, and any combination thereof. In an aspect, a modulator comprises a pharmaceutical composition described here. In another aspect, a method comprises upregulating or promoting the metabolic pathway in a patient's fecal microbiome.

In an aspect, this application provides a method for treating UC in a patient in need thereof, comprising administering a pharmaceutical composition disclosed here to the patient, wherein the patient is pretested for one or more markers from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, heme biosynthesis, lipopolysaccharide biosynthesis, ubiquinone and other terpenoid quinine biosynthesis, lysine biosynthesis, and oxidative phosphorylation pathway.

In an aspect, this application provides a method for treating UC in a patient in need thereof, comprising administering a pharmaceutical composition disclosed here to the patient, wherein the patient is pretested for the relative abundance of *Fusobacterium gonidiaformans, Prevotella copri*, or *Sutterella wadsworthensis*.

In an aspect, this application provides a method for treating UC in a patient in need thereof, comprising administering a pharmaceutical composition disclosed here to the patient, wherein the patient comprises a relative abundance of *Fusobacterium gonidiaformans, Prevotella copri*, or *Sutterella wadsworthensis* below a pre-determined highest limit.

In an aspect, this application provides a method for treating UC in a patient in need thereof, comprising administering a pharmaceutical composition disclosed here to the patient, wherein the patient comprises a relative abundance of one or more microbial taxa selected from the group consisting of *Fusobacterium, Sutterella, Haemophilus, Escherichia, Megamonas, Clostridium* cluster XIVa, *Prevotella, Dialister, Veillonella*, and *Bilophila*, below a pre-determined highest limit.

In an aspect, this application provides a method for treating UC in a patient in need thereof, comprising administering a pharmaceutical composition disclosed here to the patient, wherein the patient comprises one or more markers, above a pre-determined lowest level, from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, and starch degradation.

In an aspect, this application provides a method for treating UC in a patient in need thereof, comprising administering a pharmaceutical composition disclosed here to the patient, wherein the patient comprises one or more markers, below a pre-determined highest level, from a metabolic pathway selected from the group consisting of heme biosynthesis, lipopolysaccharide biosynthesis, ubiquinone and other terpenoid quinine biosynthesis, lysine biosynthesis, and oxidative phosphorylation pathway.

In an aspect, this application provides a method for modulating a marker from a pathway selected from the group consisting of heme biosynthesis, lipopolysaccharide biosynthesis, ubiquinone and other terpenoid quinine biosynthesis, lysine biosynthesis, and oxidative phosphorylation pathway, in a UC patient in need thereof, the method comprising administering to the patient a pharmaceutical composition disclosed here.

In an aspect of this disclosure, one or more markers are metabolic markers. In another aspect, one or more markers comprise one or more metabolic pathway genes.

In an aspect, this application provides a method for treating UC in a patient in need thereof, comprising administering to the patient a modulator of a metabolic pathway selected from the group consisting of heme biosynthesis, lipopolysaccharide biosynthesis, ubiquinone and other terpenoid quinine biosynthesis, lysine biosynthesis, oxidative phosphorylation pathway, and any combination thereof.

In an aspect, a modulator comprises a pharmaceutical composition disclosed here. In another aspect, a method comprises downregulating or suppressing the metabolic pathway in the patient's fecal microbiome.

In an aspect, this application provides a method for producing a pharmaceutical composition, the method comprising: a) determining in a candidate fecal microbe source material the relative abundance of one or more bacterial markers selected from the group consisting of *Bacteroides* OTU187, *Bacteroides fragilis*, *Bacteroides finegoldii*, *Clostridium* cluster XIVa (OTU173), *Streptococcus* (OTU56), *Sutterella wadsworthensis, Bacteroides uniformis*, and *Bacteroides coprocola*; b) selecting the candidate fecal microbe source material if the relative abundance of *Bacteroides* OTU187, *Bacteroides fragilis*, or *Bacteroides finegoldii* is above a pre-determined lowest limit, and/or if the relative abundance of *Clostridium* cluster XIVa (OTU173), *Streptococcus* (OTU56), *Sutterella wadsworthensis, Bacteroides uniformis*, or *Bacteroides coprocola* is below a pre-determined highest limit; and c) producing a pharmaceutical composition from the selected fecal microbe source material. In another aspect, a pharmaceutical composition is produced for treating UC.

In an aspect, this application provides a method for selecting a fecal donor, the method comprising: a) determining in a candidate fecal donor the relative fecal abundance of one or more bacterial markers selected from the group consisting of *Bacteroides* OTU187, *Bacteroides fragilis, Bacteroides finegoldii, Clostridium* cluster XIVa (OTU173), *Streptococcus* (OTU56), *Sutterella wadsworthensis, Bacteroides uniformis*, and *Bacteroides coprocola*; and b) selecting the candidate fecal donor for future fecal donation, if the relative fecal abundance of *Bacteroides* OTU187, *Bacteroides fragilis*, or *Bacteroides finegoldii* is above a pre-determined lowest limit, and/or if the relative fecal abundance of *Clostridium* cluster XIVa (OTU173), *Streptococcus* (OTU56), *Sutterella wadsworthensis, Bacteroides uniformis*, or *Bacteroides coprocola* is below a pre-determined highest limit. In another aspect, a donor is selected for producing a pharmaceutical composition for treating UC.

In an aspect, this application provides a method for selecting a fecal microbe source material, the method comprising: a) determining in a candidate fecal microbe source material the relative abundance of one or more markers from a metabolic pathway selected from the group consisting of fatty acid biosynthesis, propanoate metabolism, secondary bile acid biosynthesis, glycerophospholipid metabolism, and biosynthesis of ansamycins; and b) selecting the candidate fecal microbe source material if the relative abundance of the one or more markers is above a pre-determined lowest limit.

In an aspect, this application provides a method for selecting a fecal microbe source material, the method comprising a.) determining in a candidate fecal microbe source material the relative abundance of one or more markers from a metabolic pathway selected from the group consisting of fatty acid biosynthesis, propanoate metabolism, secondary bile acid biosynthesis, glycerophospholipid metabolism, biosynthesis of ansamycins, terpenoid backbone biosynthesis, bacterial chemotaxis, heme biosynthesis, and short chain fatty acid (SCFA) biosynthesis; and b.) selecting a candidate fecal microbe source material based on the relative abundance of one or more markers.

In an aspect, this application provides a method for selecting a fecal microbe source material, the method comprising: a) determining in a candidate fecal microbe source material the relative abundance of one or more markers from a metabolic pathway selected from the group consisting of terpenoid backbone biosynthesis, bacterial chemotaxis, and heme biosynthesis; and b) selecting the candidate fecal microbe source material if the relative abundance of the one or more markers is below a pre-determined highest limit.

In another aspect, a fecal microbe source material is selected for producing a pharmaceutical composition for treating UC. In another aspect, one or more markers are metabolic markers. In another aspect, one or more markers comprise one or more metabolic pathway genes.

In an aspect, this application provides a method for selecting a UC patient for a fecal microbe-based therapy, the method comprising: a) determining in a UC patient one or more markers for the relative fecal abundance of a taxon selected from the group consisting of *Clostridium* cluster XVIII, *Ruminococcus, Lachnospiraceae, Roseburia inulinivorans, Eubacterium hallii, Fusobacterium, Sutterella, Haemophilus, Escherichia, Megamonas, Clostridium* cluster XIVa, *Prevotella, Dialister, Veillonella*, and *Bilophila*; and b) selecting the UC patient for a fecal microbe-based therapy, if the relative fecal abundance of *Clostridium* cluster XVIII, *Ruminococcus, Lachnospiraceae, Roseburia inulinivorans*, or *Eubacterium hallii* is above a pre-determined lowest limit, and/or if the relative fecal abundance of *Fusobacterium, Sutterella, Haemophilus, Escherichia, Megamonas, Clostridium* cluster XIVa, *Prevotella, Dialister, Veillonella*, or *Bilophila* is below a pre-determined highest limit.

In an aspect, this application provides a method for selecting a UC patient for a fecal microbe-based therapy, the method comprising: a) determining in a UC patient one or more markers for the relative fecal abundance of a taxon selected from the group consisting of *Fusobacterium gonidiaformans*, *Prevotella copri*, and *Sutterella wadsworthensis*; and b) selecting the UC patient for a fecal microbe-based therapy, if the relative fecal abundance of the taxon is below a pre-determined highest limit.

In an aspect, this application provides a method for selecting a UC patient for a fecal microbe-based therapy, the method comprising: a) determining in a UC patient the relative fecal abundance of one or more markers for a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, and starch degradation; and b) selecting the UC patient for a fecal microbe-based therapy, if the relative fecal abundance is above a pre-determined lowest limit.

In an aspect, this application provides a method for selecting a UC patient for a fecal microbe-based therapy, the method comprising: a) determining in a UC patient the relative fecal abundance of one or more markers for a metabolic pathway selected from the group consisting of heme biosynthesis, lipopolysaccharide biosynthesis, ubiquinone and other terpenoid quinine biosynthesis, lysine biosynthesis, and oxidative phosphorylation pathway; and b) selecting the UC patient for a fecal microbe-based therapy, if the relative fecal abundance is below a pre-determined highest limit.

In another aspect, a method for selecting a UC patient further comprises subjecting a selected UC patient to a fecal microbe-based therapy.

In an aspect, a UC patient of the present disclosure exhibits a Mayo score of at least 4 prior to treatment, such as a Mayo score of 4, 5, 6, 7, 8, 9, 10. In an aspect, a UC patient of the present disclosure exhibits a Mayo score of 4 to 10 prior to treatment, such as 4 to 9, 5 to 10, 5 to 8, or 6 to 8.

In an aspect, a UC patient of the present disclosure exhibits an UCEIS score of at least 4 prior to treatment, such as an UCEIS score of 4, 5, 6, 7, 8, 9, 10. In an aspect, a UC patient of the present disclosure exhibits a UCEIS score of 4 to 10 prior to treatment, such as 4 to 9, 5 to 10, 5 to 8, or 6 to 8.

In an aspect, a UC patient of the present disclosure is capable of achieving a primary outcome at the end of a treatment regimen, where the primary outcome is defined as a steroid-free clinical remission and endoscopic remission or response at the end of the treatment regimen, where the steroid free clinical remission is defined as a total Mayo score of 2 or lower with sub-scores of 1 or lower, and where the endoscopic remission or response is defined as a reduction of at least 1 point from baseline in endoscopy score. In another aspect, a UC patient of the present disclosure is capable of achieving a primary outcome at the end of a treatment regimen, where the primary outcome is defined as a steroid-free clinical remission which is defined as a total Mayo score of 2 or lower with sub-scores of 1 or lower. In a further aspect, a UC patient of the present disclosure is capable of achieving a primary outcome at the end of a treatment regimen, where the primary outcome is defined as a steroid-free endoscopic remission or response which is defined as a reduction of at least 1 point from baseline in endoscopy score.

In an aspect, a patient of the present disclosure has no steroid use within at least one week prior to commencing the methods provided herein. In another aspect, a patient of the present disclosure has no steroid use within at least two, three, four, or five weeks prior to commencing the methods provided herein. In a further aspect, a patient of the present disclosure has no steroid use within at least 1, 2, 3, 4, 5, 6, 7, 8, 9, 10, 11, 12, 13, or 14 days prior to commencing the methods provided herein. In an aspect, a steroid may be prednisone, budesonide, or hydrocortisone. In an aspect, a patient of the present disclosure has no corticosteroid use within at least one week prior to commencing the methods provided herein. In an aspect, a patient of the present disclosure has no corticosteroid use prior to commencing the methods provided herein.

In an aspect, a method of the present disclosure further comprise determining the patient's baseline gut bacterial diversity. In an aspect, a patient's baseline gut bacterial diversity is assessed by analyzing Shannon's diversity of the patient's fecal sample prior to the treating step. In an aspect, a patient's baseline fecal Shannon diversity is between 0.5 and 2.2 based on bacterial species level, such as between 0.5 and 2.0, between 1.0 and 2.2, or between 1.0 and 1.5. In an aspect, a patient's fecal Shannon diversity increases by at least 50%, 60%, 70%, 80%, 90%, 95%, 98%, 99%, 99.5%, 99.8%, or 99.9% compared to before treatment. In an aspect, a patient's fecal Shannon diversity increases by at least 1, 2, 3, 4, 5, 6, 7, 8, 9, 10, 11, 15, 20, or 30 folds compared to before treatment. In an aspect, a patient's post-treatment fecal Shannon diversity is between 1.5 and 6.0 based on bacterial species level, such as between 1.5 and 5.0, between 1.5 and 4.5, between 1.5 and 4.0, between 1.5 and 3.5, between 1.5 and 3.0, between 1.5 and 2.5, between 1.5 and 2.0, between 2.0 and 4.5, between 2.5 and 4.0, between 3.0 and 3.5, between 2.0 and 6.0, between 2.5 and 6.0, between 3.0 and 6.0, between 3.5 and 6.0, between 4.0 and 6.0, between 4.5 and 6.0, between 5.0 and 6.0, and between 5.5 and 6.0.

In an aspect, the present disclosure provides a UC treatment that is capable of achieving a primary outcome rate of at least two fold higher relative to a primary outcome rate from placebo, where the primary outcome is defined as a steroid-free clinical remission and endoscopic remission or response at the end of the UC treatment, where the clinical remission is defined as a total Mayo score of 2 or lower with all sub-scores of 1 or lower, and where the endoscopic remission or response is defined as a reduction of at least 1 point from baseline in Mayo endoscopy score. In an aspect, the present disclosure provides a UC treatment that is capable of achieving a primary outcome rate higher than a primary outcome rate from placebo, where the primary outcome is defined as a steroid-free clinical remission and endoscopic remission or response at the end of the UC treatment, where the clinical remission is defined as a total Mayo score of 2 or lower with all sub-scores of 1 or lower, and where the endoscopic remission or response is defined as a reduction of at least 1 point from baseline in Mayo endoscopy score.

In an aspect, a UC treatment in accordance with the present disclosure is capable of achieving a primary outcome rate of at least 25%, such as at least 20%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, at least 99.5%, or at least 99.9%. In an aspect, a UC treatment is capable of achieving a primary outcome rate of between 20% to 40%, such as between 20% and 35%, between 25% and 40%, between 25% and 35%, between 25% and 30%, or between 30% and 35%.

In an aspect, a UC treatment in accordance with the present disclosure is capable of achieving a clinical remission sustaining rate of at least 40% at 8 weeks after the completion of the UC treatment. In an aspect, a UC treatment is capable of achieving a clinical remission sustaining rate of at least 45%, such as at least 50%, at least 55%, at least 60%, at least 65%, at least 70%, at least 75%, at least 80%, at least 85%, at least 90%, at least 95%, at least 98%, at least 99%, at least 99.5%, or at least 99.9% at 8 weeks after the completion of the UC treatment. In an aspect, a UC treatment is capable of achieving a clinical remission sustaining rate of between 35% and 60%, such as between 35% and 55%, between 40% and 60%, between 40% and 55%, between 40% and 50%, between 45% and 55%, or between 45% and 50% at 8 weeks after the completion of the UC treatment.

In an aspect, a UC treatment in accordance with the present disclosure is capable of achieving a steroid-free clinical remission rate of at least two fold higher relative to a steroid-free clinical remission rate from placebo, where the clinical remission is defined as a combined Mayo score of 1 or lower for rectal bleeding and stool frequency. In an aspect, a UC treatment in accordance with the present disclosure is capable of achieving a steroid-free clinical remission rate higher than a steroid-free clinical remission rate from placebo, where the clinical remission is defined as a combined Mayo score of 1 or lower for rectal bleeding and stool frequency. In an aspect, a UC treatment is capable of achieving a steroid-free clinical remission rate of at least 40%, such as at least 45%, at least 50%, at least 55%, at least 60%, at least 65%, at least 70%, at least 75%, at least 80%, at least 85%, at least 90%, at least 95%, at least 98%, at least 99%, at least 99.5%, or at least 99.9%. In an aspect, a UC treatment is capable of achieving a steroid-free clinical remission rate of between 35% and 55%, such as between 40% and 55%, between 35% and 50%, between 40% and 50%, between 40% and 45%, or between 45% and 50%.

In an aspect, a UC treatment in accordance with the present disclosure is capable of achieving a steroid-free clinical response rate of at least two fold higher relative to a steroid-free clinical response rate from placebo, where the clinical response is defined as a total Mayo score decrease of 3 or higher or a 50% higher reduction from baseline in combined score for rectal bleeding and stool frequency. In an aspect, a UC treatment in accordance with the present disclosure is capable of achieving a steroid-free clinical response rate higher than a steroid-free clinical response rate from placebo, where the clinical response is defined as a total Mayo score decrease of 3 or higher or a 50% higher reduction from baseline in combined score for rectal bleeding and stool frequency. In an aspect, a UC treatment is capable of achieving a steroid-free clinical response rate of at least 50%, such as at least 55%, at least 60%, at least 65%, at least 70%, at least 75%, at least 80%, at least 85%, at least 90%, at least 95%, at least 98%, at least 99%, at least 99.5%, or at least 99.9%. In an aspect, a UC treatment in accordance with the present disclosure is capable of achieving a steroid-free clinical response rate between 45% and 65%, such as between 45% and 60%, between 50% and 65%, between 50% and 60%, between 50% and 55%, or between 55% and 60%.

In an aspect, a UC treatment in accordance with the present disclosure is capable of achieving an endoscopic response rate of at least two fold higher relative to an endoscopic response rate from placebo, where the endoscopic response is defined as a total UCEIS score decrease of 3 or higher or a 50% or higher reduction from baseline. In an aspect, a UC treatment in accordance with the present disclosure is capable of achieving an endoscopic response rate higher than an endoscopic response rate from placebo, where the endoscopic response is defined as a total UCEIS score decrease of 3 or higher or a 50% or higher reduction from baseline. In an aspect, a UC treatment is capable of achieving an endoscopic rate of at least 30%, such as at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, at least 99.5%, or at least 99.9%. In an aspect, a UC treatment is capable of achieving an endoscopic response rate between 30% and 45%, such as between 30% and 40%, between 35% and 45%, or between 35% and 40%.

In an aspect, the present disclosure provides a method for treating ulcerative colitis in a patient in need thereof, where the method comprises administering to a UC patient a pharmaceutically active dose of a pharmaceutical composition comprising viable non-pathogenic fecal bacteria described here. In another aspect, this disclosure provides use of a composition comprising viable non-pathogenic fecal bacteria in the manufacture of a medication for the treatment of ulcerative colitis.

In an aspect, a method of the present disclosure treats a form of ulcerative colitis selected from the group consisting of ulcerative proctitis, proctosigmoiditis, left-sided colitis, and pan-ulcerative colitis. In an aspect, a pharmaceutical composition in accordance with the present disclosure comprises a fecal microbiota preparation. In an aspect, a pharmaceutical composition comprises an isolated or purified population of viable non-pathogenic fecal bacteria. In an aspect, a pharmaceutical composition comprises a non-selective fecal microbiota. In an aspect, a pharmaceutical composition comprises a non-selected and substantially complete fecal microbiota. In another aspect, a pharmaceutical composition comprises a substantially complete fecal microbiota. In an aspect, a method further comprises administering a 5-aminosalicylic acid agent, a corticosteroid, an immunosuppressant, or a combination thereof. In another aspect, a method further comprises administering 5-aminosalicylic acid or a derivative thereof, sulfasalazine or a derivative thereof, or a combination thereof.

In an aspect, the present disclosure provides a method for selecting a treatment plan for treating ulcerative colitis in a patient in need thereof, where the method comprises determining the level of *Fusobacterium gonidiaformans, Prevotella copri,* and/or *Sutterella wadsworthensis* in the patient's gut; and recommending a fecal bacteria-based therapy when the level of *Fusobacterium gonidiaformans, Prevotella copri,* and/or *Sutterella wadsworthensis* is above a predetermined level. In an aspect, the level of *Fusobacterium gonidiaformans, Prevotella copri,* and/or *Sutterella wadsworthensis* is about 8% above a predetermined level, such as about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, or about 200% above a predetermined level. In an aspect, the present disclosure provides a method for selecting a treatment plan for treating ulcerative colitis in a patient in need thereof, where the method comprises determining the level of *Fusobacterium gonidiaformans, Prevotella copri,* and/or *Sutterella wadsworthensis* in the patient's gut; and recommending a fecal bacteria-based therapy when the level of *Fusobacterium gonidiaformans,*

*Prevotella copri*, and/or *Sutterella wadsworthensis* is between a predetermined range. In an aspect, the predetermined range is about 8% to about 50% above a predetermined level, such as about 8% to about 40%, about 10% to 50%, about 15% to about 40%, about 20% to about 35%, or about 25% to about 30% above a predetermined level. In an aspect, the predetermined range is about 50% to about 200% above a predetermined level, such as about 50% to about 150%, about 50% to about 100%, about 100% to 150%, about 80% to about 120%, about 90% to about 110%, or about 98% to about 100% above a predetermined level. In an aspect, the level of one or more bacteria is determined via analyzing a patient's feces.

In an aspect, the present disclosure provides a method for selecting a treatment plan for treating ulcerative colitis in a patient in need thereof, where the method comprises determining the level of one or more bacteria selected from the group consisting of *Clostridium* cluster XVIII, *Ruminococcus, Lachnospiraceae, Roseburia inulinivorans*, and *Eubacterium hallii* in the patient's gut; and recommending a fecal bacteria-based therapy when the level of the one or more selected bacteria is above a predetermined level. In an aspect, the level of the one or more selected bacteria is about 8% above a predetermined level, such as about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, or about 200% above a predetermined level. In an aspect, the present disclosure provides a method for selecting a treatment plan for treating ulcerative colitis in a patient in need thereof, where the method comprises determining the level of one or more bacteria selected from the group consisting of *Clostridium* cluster XVIII, *Ruminococcus, Lachnospiraceae, Roseburia inulinivorans*, and *Eubacterium hallii* in the patient's gut; and recommending a fecal bacteria-based therapy when the level of the one or more selected bacteria is between a predetermined range. In an aspect, the predetermined range is about 8% to about 50% above a predetermined level, such as about 8% to about 40%, about 10% to 50%, about 15% to about 40%, about 20% to about 35%, or about 25% to about 30% above a predetermined level. In an aspect, the predetermined range is about 50% to about 200% above a predetermined level, such as about 50% to about 150%, about 50% to about 100%, about 100% to 150%, about 80% to about 120%, about 90% to about 110%, or about 98% to about 100% above a predetermined level. In an aspect, the level of one or more bacteria is determined via analyzing a patient's feces.

In an aspect, a predetermined level, a predetermined highest limit, or a predetermined lowest limit is established by the corresponding level of the one or more selected bacteria in healthy subjects. In an aspect, a predetermined level, a predetermined highest limit, or a predetermined lowest limit is established by the corresponding level of the one or more selected bacteria in healthy subjects in the same demographic category as the subject. In an aspect, a predetermined level, a predetermined highest limit, or a predetermined lowest limit is established by the abundance of the total *Clostridium* or *Bacteriodetes* population in the same subject.

In an aspect, the present disclosure provides a method which eliminates or reduces one or more ulcerative colitis symptoms selected from the group consisting of diarrhea, cramp, tenesmus, weight loss, bleeding, loss of appetite, abdominal pain, fever, fatigue, anaemia, inflammation, and micro-ulcers.

In an aspect, the present disclosure provides a method for treating ulcerative colitis in a patient in need thereof, where the method comprises administering to a UC patient a pharmaceutically active dose of a pharmaceutical composition comprising viable non-pathogenic bacteria described here. In an aspect, the present disclosure provides a method for treating ulcerative colitis in a patient in need thereof, where the method comprises administering daily to a UC patient a pharmaceutically active dose of a pharmaceutical composition comprising viable non-pathogenic fecal bacteria. In an aspect, a pharmaceutical composition is administered to an ulcerative colitis patient in need thereof at least once daily for at least two consecutive days. In an aspect, a pharmaceutical composition is administered at least once daily for at least 3, 4, 5, 6, 7, 8, 9, 10, 11, 12, 13, 14, or 15 consecutive days. In another aspect, a pharmaceutical composition is administered at least once daily for at least 1, 2, 3, 4, 5, 6, 7, 8, 9, 10, 11, or 12 consecutive weeks. In an aspect, a pharmaceutical composition is administered at least once daily for at most 4, 5, 6, 7, 8, 9, 10, 11, 12, 13, 14, 15, 16, 17, 18, 19, or 20 consecutive days or weeks. In another aspect, a pharmaceutical composition is administered at least once daily for at most 1, 2, 3, 4, 5, 6, 7, 8, 9, 10, 11, or 12 consecutive weeks or months. In a further aspect, a pharmaceutical composition is administered at least once for at least 1, 2, 3, 4, 5, 6, 7, 8, 9, 10, 11, or 12 consecutive months or years, chronically for a patient's entire life span, or an indefinite period of time.

In an aspect, a pharmaceutical composition is administered to an ulcerative colitis patient in need thereof at least twice daily for at least two consecutive days. In an aspect, a pharmaceutical composition is administered at least twice daily for at least 3, 4, 5, 6, 7, 8, 9, 10, 11, 12, 13, 14, or 15 consecutive days. In another aspect, a pharmaceutical composition is administered at least twice daily for at least 1, 2, 3, 4, 5, 6, 7, 8, 9, 10, 11, or 12 consecutive weeks. In an aspect, a pharmaceutical composition is administered at least twice daily for at most 4, 5, 6, 7, 8, 9, 10, 11, 12, 13, 14, 15, 16, 17, 18, 19, or 20 consecutive days or week. In another aspect, a pharmaceutical composition is administered at least twice daily for at most 1, 2, 3, 4, 5, 6, 7, 8, 9, 10, 11, or 12 consecutive weeks or months. In a further aspect, a pharmaceutical composition is administered at least twice for at least 1, 2, 3, 4, 5, 6, 7, 8, 9, 10, 11, or 12 consecutive months or years, chronically for a patient's entire life span, or an indefinite period of time.

In an aspect, a pharmaceutical composition is administered to an ulcerative colitis patient in need thereof at least three times daily for at least two consecutive days. In an aspect, a pharmaceutical composition is administered at least three times daily for at least 3, 4, 5, 6, 7, 8, 9, 10, 11, 12, 13, 14, or 15 consecutive days. In another aspect, a pharmaceutical composition is administered at least three times daily for at least 1, 2, 3, 4, 5, 6, 7, 8, 9, 10, 11, or 12 consecutive weeks. In an aspect, a pharmaceutical composition is administered at least three times daily for at most 4, 5, 6, 7, 8, 9, 10, 11, 12, 13, 14, 15, 16, 17, 18, 19, or 20 consecutive days or weeks. In another aspect, a pharmaceutical composition is administered at least three times daily for at most 1, 2, 3, 4, 5, 6, 7, 8, 9, 10, 11, or 12 consecutive weeks or months. In a further aspect, a pharmaceutical composition is administered at least three times for at least 1, 2, 3, 4, 5, 6, 7, 8, 9, 10, 11, or 12 consecutive months or years, chronically for a patient's entire life span, or an indefinite period of time.

In an aspect, the present disclosure provides a method for treating ulcerative colitis in a patient in need thereof, where the method comprises administering orally to a UC patient a pharmaceutically active dose of a pharmaceutical composition comprising viable, non-pathogenic, synthetic bacterial mixture or viable, non-pathogenic, purified or extracted, fecal microbiota, where the dose is administered at a dosing schedule of at least once or twice daily for at least three consecutive days or weeks. In another aspect, a dose is administered at least once, twice, or three times daily for a period between 1 and 12 weeks, between 2 and 12 weeks, between 3 and 12 weeks, between 4 and 12 weeks, between 5 and 12 weeks, between 6 and 12 weeks, between 7 and 12 weeks, between 8 and 12 weeks, between 9 and 12 weeks, between 10 and 12 weeks, between 1 and 2 weeks, between 2 and 3 weeks, between 3 and 4 weeks, between 4 and 5 weeks, between 5 and 6 weeks, between 6 and 7 weeks, between 7 and 8 weeks, between 8 and 9 weeks, between 9 and 10 weeks, or between 10 and 11 weeks.

In an aspect, the present disclosure provides a method for treating ulcerative colitis in a patient in need thereof, where the method comprises a first dosing schedule followed by a second dosing schedule. In an aspect, a first dosing schedule comprises a treatment or induction dose. In an aspect, a first dosing schedule comprises a continuous dosing schedule. In another aspect, a second dosing schedule comprises a maintenance dose lower than or equal to a pharmaceutically active dose of a first dosing schedule. In another aspect, a second dosing schedule lasts for at least about 2, 4, 6, 8, 10, 12, 18, 24, 36, 48, 72, or 96 months. In an aspect, a second dosing schedule lasts permanently, for a treated patient's entire life span, or an indefinite period of time. In an aspect, a second dosing schedule is a continuous dosing schedule. In another aspect, a second dosing schedule is an intermittent dosing schedule. In a further aspect, a second dosing schedule is an intermittent dosing schedule comprising a treatment period of at least 1, 2, 3, 4, 5, 6, 7, 8, 9, 10, 11, 12, 13, or 14 days followed by a resting period of at least 1, 2, 3, 4, 5, 6, 7, 8, 9, 10, 11, 12, 13, or 14 days. In another aspect, a second dosing schedule comprises administering a second dose (e.g., a maintenance dose) every other day, every two days, or every 3, 4, 5, 6, 7, 8 days. In another aspect, a maintenance dose is administered for an extended period of time with or without titration (or otherwise changing the dosage or dosing schedule). In an aspect, the interval between a first and a second dosing schedule is at least about 1, 2, 3, 4, 5, 6, 7, 8, 9, 10, 11, or 12 weeks. In another aspect, a second dosing schedule (e.g., a maintenance dose) comprises a dosage about 2, 5, 10, 50, 100, 200, 400, 800, 1000, 5000 or more folds lower than the dosage used in a first dosing schedule (e.g., an initial treatment dose). In another aspect, a second dosing schedule (e.g., a maintenance dosing schedule) has an equal or lower dosing frequency than a first dosing schedule (e.g., an initial treatment dosing schedule). In another aspect, a second dosing schedule (e.g., a maintenance dosing schedule) has a higher dosing interval than a first dosing schedule (e.g., an initial treatment dosing schedule).

In an aspect, a first or second dosing schedule used in a method can be once-a-week, twice-a-week, or thrice-a-week. The term "once-a-week" means that a dose is administered once in a week, preferably on the same day of each week. "Twice-a-week" means that a dose is administered two times in a week, preferably on the same two days of each weekly period. "Thrice-a-week" means that a dose is administered three times in a week, preferably on the same three days of each weekly period.

In an aspect, a patient being treated is a patient already with ulcerative colitis. Administration of a disclosed pharmaceutical composition to a clinically symptomatic human subject who is genetically predisposed or prone to ulcerative colitis is also useful in preventing or inhibiting the onset of clinical symptoms of ulcerative colitis. A human subject genetically predisposed or prone to ulcerative colitis can be a human subject having a close family member or relative exhibiting or having suffered ulcerative colitis. In another aspect, a subject being treated is a subject in which ulcerative colitis is to be prevented or inhibited. In another aspect, a subject being treated is predisposed or susceptible to ulcerative colitis. In another aspect, a patient being treated is a patient diagnosed as having ulcerative colitis. In an aspect, a patient being treated is a patient in need thereof.

In an aspect, a patient is a male patient. In an aspect, a patient is a female patient. In an aspect, a patient is a premature newborn. In an aspect, a patient is a term newborn. In an aspect, a patient is a neonate. In an aspect, a patient is an infant. In an aspect, a patient is a toddler. In an aspect, a patient is a young child. In an aspect, a patient is a child. In an aspect, a patient is an adolescent. In an aspect, a patient is a pediatric patient. In an aspect, a patient is a geriatric patient. In an aspect, a human patient is a child patient below about 18, 15, 12, 10, 8, 6, 4, 3, 2, or 1 year old. In another aspect, a human patient is an adult patient. In another aspect, a human patient is an elderly patient. In a further aspect, a human patient is a patient above about 30, 35, 40, 45, 50, 55, 60, 65, 70, 75, 80, 85, 90, or 95 years old. In another aspect, a patient is about between 1 and 5, between 2 and 10, between 3 and 18, between 21 and 50, between 21 and 40, between 21 and 30, between 50 and 90, between 60 and 90, between 70 and 90, between 60 and 80, or between 65 and 75 years old. In an aspect, a patient is a young old patient (65-74 years). In an aspect, a patient is a middle old patient (75-84 years). In an aspect, a patient is an old patient (>85 years).

In an aspect, a method comprises administering a pharmaceutical composition orally, by enema, or via rectal suppository. In an aspect, a pharmaceutical composition administered herein is formulated as an enteric coated (and/or acid-resistant) capsule or microcapsule, or formulated as part of or administered together with a food, a food additive, a dairy-based product, a soy-based product or a derivative thereof, a jelly, or a yogurt. In another aspect, a pharmaceutical composition administered herein is formulated as an acid-resistant enteric coated capsule. A pharmaceutical composition can be provided as a powder for sale in combination with a food or drink. A food or drink can be a dairy-based product or a soy-based product. In another aspect, a food or food supplement contains enteric-coated and/or acid-resistant microcapsules containing a pharmaceutical composition.

In an aspect, a pharmaceutical composition comprises a liquid culture. In another aspect, a pharmaceutical composition is lyophilized, pulverized and powdered. It may then be infused, dissolved such as in saline, as an enema. Alternatively the powder may be encapsulated as enteric-coated and/or acid-resistant capsules for oral administration. These capsules may take the form of enteric-coated and/or acid-resistant microcapsules. A powder can preferably be provided in a palatable form for reconstitution for drinking or for reconstitution as a food additive. In a further aspect, a food is yogurt. In an aspect, a powder may be reconstituted to be infused via naso-duodenal infusion.

In another aspect, a pharmaceutical composition administered herein is in a liquid, frozen, freeze-dried, spray-dried, lyophilized, or powder form. In a further aspect, a pharmaceutical composition administered herein is formulated as a delayed or gradual enteric release form. In another aspect, a pharmaceutical composition administered herein comprises an excipient, a saline, a buffer, a buffering agent, or a fluid-glucose-cellobiose agar (RGCA) media. In another aspect, a pharmaceutical composition administered herein comprises a cryoprotectant. In an aspect, a cryoprotectant comprises polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof.

In one aspect, a pharmaceutical composition comprises a lyophilized formulation further comprising a reducing agent. In certain embodiments, the reducing agent comprises cysteine selected from the group consisting of D-cysteine and L-cysteine. In another aspect, cysteine is at a concentration of at least about 0.025%. In one aspect, cysteine is at a concentration of about 0.025%. In another aspect, cysteine is at a concentration of 0.025%. In another aspect, another reducing agent other than cysteine is used in lieu of, or in combination with cysteine. In an aspect, another reducing agent is selected from the group comprising ascorbic acid, sodium ascorbate, thioglycolic acid, sodium sulfite, sodium bisulfate, sodium metabisulfite, potassium metabisulfite, Glutathione, Methionine, thioglycerol, and alpha tocopherol.

In one aspect, cysteine is at a concentration of at least about 0.005%, at least about 0.01%, at least about 0.015%, at least about 0.02%, at least about 0.025%, at least about 0.03%, at least about 0.035%, at least about 0.04%, at least about 0.045%, at least about 0.05%, at least about 0.055%, at least about 0.06%, at least about 0.065%, at least about 0.07%, at least about 0.075%, at least about 0.08%, at least about 0.085%, at least about 0.09%, at least about 0.095%, at least about 0.1%, at least about 0.12%, at least about 0.14%, at least about 0.16%, at least about 0.18%, at least about 0.2%, at least about 0.25%, at least about 0.3%, at least about 0.4%, at least about 0.5%, at least about 0.6%, at least about 0.7%, at least about 0.8%, at least about 0.9%, at least about 1%, at least about 2%, at least about 4%, at least about 6%, at least about 8%, at least about 10%, at least about 12%, at least about 14%, at least about 16%, at least about 18%, at least about 20%, at least about 22%, at least about 24%, or at least about 26%.

In one aspect, a therapeutic composition comprises a cryoprotectant. As used herein, a "cryoprotectant" refers to a substance that is added to a formulation in order to protect an active ingredient during freezing. In an aspect, a cryoprotectant comprises, consists essentially of, or consists of polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof. In an aspect of the present disclosure, a cryoprotectant can be selected from the group comprising 5% Sucrose; 10% Sucrose; 10% Skim milk; 10% Trehalose with 2.5% sucrose; 5% Trehalose with 2.5% sucrose; 5% Mannitol; 5% Mannitol with 0.1% Polysorbate 80; 10% Mannitol; 10% Mannitol with 0.1% Polysorbate 80; 5% Trehalose; 5% Trehalose with 0.1% Polysorbate 80; 10% Trehalose; and 10% Trehalose with 0.1% Polysorbate 80.

In another aspect, a therapeutic composition comprises a lyoprotectant. As used herein, a "lyoprotectant" refers to a substance that is added to a formulation in order to protect an active ingredient during the drying stage of a lyophilization (also known as freeze-drying) process. In one aspect, the same substance or the same substance combination is used as both a cryoprotectant and a lyoprotectant. Exemplary lyoprotectants include sugars such as sucrose or trehalose; an amino acid such as monosodium glutamate or histidine; a methylamine such as betaine; a lyotropic salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. In one aspect, a lyoprotectant is a non-reducing sugar, such as trehalose or sucrose. In one aspect, a cryoprotectant or a lyoprotectant consists essentially of, or consists of, one or more substances mentioned in this paragraph and the paragraph above.

In one aspect, a cryoprotectant or a lyoprotectant comprise an intracellular agent, e.g., DMSO, Glycerol, or PEG, which penetrates inside the cell preventing the formation of ice crystals that could result in membrane rupture. In another aspect, a cryoprotectant or a lyoprotectant comprise an extracellular agent, e.g., sucrose, trehalose, or dextrose, which does not penetrate into the cell membrane but acts to improve the osmotic imbalance that occurs during freezing.

In one aspect, the present disclosure provides a pharmaceutical composition comprising a lyophilized fecal microbe preparation comprising a lyophilization formulation comprising at least about 12.5% trehalose.

In one aspect, a lyophilization formulation comprises at least about 5%, at least about 7.5%, at least about 10%, at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20%, at least about 22.5%, at least about 25%, at least about 27.5%, at least about 30%, at least about 32.5%, at least about 35%, at least about 37.5%, at least about 40%, at least about 42.5%, at least about 45%, at least about 47.5%, at least about 50%, at least about 52.5%, at least about 55%, at least about 57.5%, or at least about 60% of trehalose.

In an aspect, a pharmaceutical composition administered herein further comprises an acid suppressant, an antacid, an H2 antagonist, a proton pump inhibitor or a combination thereof. In an aspect, a pharmaceutical composition administered herein is substantially free of non-living matter. In another aspect, a pharmaceutical composition administered herein is substantially free of acellular material selected from the group consisting of residual fiber, DNA, viral coat material, and non-viable material.

The compositions and methods of the present invention may further comprise one or more prebiotics.

A prebiotic is a substrate that is selectively used by a host microorganism to produce a health benefit in a subject/patient. Without wishing to be bound by theory, prebiotics are added to nutritionally supplement bacteria in the microbiome and/or in a microbial composition, e.g., to stimulate the growth or activity of one or more strains of beneficial bacteria. Additionally, the prebiotics may be added to prevent "shock" to bacterial strains subsequent to their isolation or purification, freezing, freeze-drying, spray-drying, reconstitution in solution and the like.

Examples of prebiotics include amino acids, ammonium nitrate, amylose, barley mulch, biotin, carbonate, cellulose, chitin, choline, fructooligosaccharides (FOSs), fructose, galactooligosaccharides (GOSs), glucose, glycerol, heteropolysaccharide, histidine, homopolysaccharide, hydroxyapatite, inulin, isomaltulose, lactose, lactulose, maltodextrins, maltose, mannooligosaccharides, tagatose, nitrogen, oligodextrose, oligofructoses, oligofructose-enriched inulin, oligosaccharides, pectin, phosphate salts, phosphorus, polydextroses, polyols, potash, potassium, sodium nitrate, starch, sucrose, sulfur, sun fiber, tagatose, thiamine, trans-galactooligosaccharides, trehalose, vitamins, a water-soluble carbohydrate, and/or xylooligosaccharides (XOSs).

In embodiments, a prebiotic can be added (e.g., in dry or liquid forms) to a microbial composition of the present invention.

Alternately, or additionally, a prebiotic can be included (e.g., in dry or liquid forms) in a distinct pharmaceutical composition which lacks a microbial composition of the present invention.

A prebiotic may be provided to a subject before, contemporaneously with, and/or after a pharmaceutical composition comprising a microbial composition of the present invention is administered, either in a pharmaceutical composition comprising the microbial composition or in a pharmaceutical composition lacking a microbial composition.

A prebiotic may be provided in a single dose or in multiple doses. When provided as a single composition, the single composition may comprise a single prebiotic or a mixture of prebiotics. When provided in multiple compositions, each composition may comprise a single prebiotic or a mixture of prebiotics.

As examples, when multiple doses are provided, a first composition comprising a prebiotic may include one specific prebiotic, e.g., inulin, and a second composition may include a second specific prebiotic, e.g., pectin. Alternately, a first composition may include a mixture of prebiotics, e.g., inulin and pectin and a second composition may include different mixture of prebiotics, e.g., inulin and a FOS. A first composition may include a mixture of prebiotics and a second composition may include one specific prebiotic.

The amount of prebiotic provided to a subject/patient and/or included in a composition depends on the specific prebiotic, the specific bacterial strain of beneficial bacteria, and/or the disease state of the subject/patient.

In an aspect, a method further comprises pretreating a subject with an antibiotic composition prior to administering a pharmaceutical bacterial or microbiota composition. In an aspect, an antibiotic composition administered herein comprises an antibiotic selected from the group consisting of rifabutin, clarithromycin, clofazimine, vancomycin, rifampicin, nitroimidazole, chloramphenicol, and a combination thereof. In another aspect, an antibiotic composition administered herein comprises an antibiotic selected from the group consisting of rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, and a combination thereof. In a further aspect, a method further comprises pretreating a subject with an anti-inflammatory drug prior to administration of a pharmaceutical bacterial or microbiota composition.

In an aspect, a method achieves a remission, cure, response, or resolution rate of ulcerative colitis of at least about 10%, 15%, 20%, 25%, 30%, 35%, 40%, 45%, 50%, 55%, 60%, 65%, 70%, 75%, 80%, 85%, 90%, 95%, 97%, or 99%. In an aspect, a treatment method achieves a reduction of ulcerative colitis disease activity index (UCDAI) after 8 weeks of treatment by more than 2, 3, 4, 5, 6, 7, 8, 9, 10, or 11. In another aspect, a treatment method achieves a reduction of ulcerative colitis disease activity index (UCDAI) after 8 weeks of treatment by more than 2, 3, 4, 5, 6, 7, 8, 9, 10, or 11 in at least 10%, 20%, 30%, 50%, 60%, 70%, 80%, or 90% patients in a patient population. In an aspect, a treatment method achieves at least 10%, 20%, 30%, 50%, 60%, 70%, 80%, or 90% reduction of ulcerative colitis disease activity index (UCDAI) after 8 weeks of treatment compared to baseline (e.g., immediately prior to treatment). In an aspect, a treatment method achieves at least 10%, 20%, 30%, 50%, 60%, 70%, 80%, or 90% reduction of ulcerative colitis disease activity index (UCDAI) in at least 10%, 20%, 30%, 50%, 60%, 70%, 80%, or 90% patients after 8 weeks of treatment compared to baseline (e.g., immediately prior to treatment).

In a further aspect, a patient is assessed using the Disease Activity Index (DAI) or Mayo score system as described in Schroeder et al., Coated oral 5-aminosalcylic acid therapy for mildly to moderately active ulcerative colitis. *N Eng J Med.* 1987; 317: 1625-1629. In an aspect, a treatment method achieves at least 10%, 20%, 30%, 50%, 60%, 70%, 80%, or 90% reduction of Mayo score after 8 weeks of treatment compared to baseline (e.g., immediately prior to treatment). In an aspect, a treatment method achieves at least 10%, 20%, 30%, 50%, 60%, 70%, 80%, or 90% reduction of Mayo score in at least 10%, 20%, 30%, 50%, 60%, 70%, 80%, or 90% patients after 8 weeks of treatment compared to baseline (e.g., immediately prior to treatment).

In an aspect, a pharmaceutically active or therapeutically effective dose comprises at least about $10^5$, $10^6$, $10^7$, $10^8$, $10^9$, $10^{10}$, $10^{11}$, $10^{12}$, or $10^{13}$ cfu. In another aspect, a pharmaceutically active therapeutically effective dose comprises at most about $10^5$, $10^6$, $10^7$, $10^8$, $10^9$, $10^{10}$, $10^{11}$, $10^{12}$, or $10^{13}$ cfu. In a further aspect, a pharmacologically active therapeutically effective dose is selected from the group consisting of from $10^8$ cfu to $10^{14}$ cfu, from $10^9$ cfu to $10^{13}$ cfu, from $10^{10}$ cfu to $10^{12}$ cfu, from $10^9$ cfu to $10^{14}$ cfu, from $10^9$ cfu to $10^{12}$ cfu, from $10^9$ cfu to $10^{11}$ cfu, from $10^9$ cfu to $10^{10}$ cfu, from $10^{10}$ cfu to $10^{14}$ cfu, from $10^{10}$ cfu to $10^{13}$ cfu, from $10^{11}$ cfu to $10^{14}$ cfu, from $10^{11}$ cfu to $10^{13}$ cfu, from $10^{12}$ cfu to $10^{14}$ cfu, and from $10^{13}$ cfu to $10^{14}$ cfu.

In an aspect, a pharmaceutically active or therapeutically effective dose comprises at least about $10^5$, $10^6$, $10^7$, $10^8$, $10^9$, $10^{10}$, $10^{11}$, $10^{12}$, or $10^{13}$ cells or spores. In another aspect, a pharmaceutically active or therapeutically effective dose comprises at most about $10^5$, $10^6$, $10^7$, $10^8$, $10^9$, $10^{10}$, $10^{11}$, $10^{12}$, or $10^{13}$ total cells or spores. In a further aspect, a pharmacologically active or therapeutically effective dose is selected from the group consisting of from $10^8$ to $10^{14}$, from $10^9$ to $10^{13}$, from $10^{10}$ to $10^{12}$, from $10^9$ to $10^{14}$, from $10^9$ to $10^{12}$, from $10^9$ to $10^{11}$, from $10^9$ to $10^{10}$, from $10^{10}$ to $10^{14}$, from $10^{10}$ to $10^{13}$, from $10^{11}$ to $10^{14}$, from $10^{11}$ to $10^{13}$, from $10^{12}$ to $10^{14}$, and from $10^{13}$ to $10^{14}$ cells or spores. In an aspect, the pharmaceutically active or therapeutically effective dose cell count is directed to viable cells.

In an aspect, a pharmaceutical composition administered herein comprises a fecal microbiota. In another aspect, the preparation of a fecal microbiota used herein involves a treatment selected from the group consisting of ethanol treatment, detergent treatment, heat treatment, irradiation, and sonication. In another aspect, the preparation of a fecal microbiota used herein involves no treatment selected from the group consisting of ethanol treatment, detergent treatment, heat treatment, irradiation, and sonication. In an aspect, the preparation of a fecal microbiota used herein involves a separation step selected from the group consisting of density gradients, filtration (e.g., sieves, nylon mesh), and chromatography. In another aspect, the preparation of a fecal microbiota used herein involves no separation step selected from the group consisting of density gradients, filtration (e.g., sieves, nylon mesh), and chromatography. In another aspect, a fecal microbiota used herein comprises a donor's entire fecal microbiota. In another aspect, a pharmaceutical composition administered herein comprises a fecal microbiota substantially free of eukaryotic cells from the fecal microbiota's donor.

In another aspect, a pharmaceutical composition administered herein comprises a fecal microbiota further supplemented, spiked, or enhanced with a fecal microorganism. In an aspect, a fecal microbiota is supplemented with a non-pathogenic (or with attenuated pathogenicity) bacterium of *Clostridium, Collinsella, Dorea, Ruminococcus, Coprococcus, Prevotella, Veillonella, Bacteroides, Baccillus*, or a combination thereof. In another aspect, a pharmaceutical composition administered herein comprises a fecal microbiota further supplemented, spiked, or enhanced with a species of *Veillonellaceae, Firmicutes, Gammaproteobacteria, Bacteroidetes*, or a combination thereof. In another aspect, a pharmaceutical composition administered herein comprises a fecal microbiota further supplemented with fecal bacterial spores. In an aspect, fecal bacterial spores are *Clostridium* spores, *Bacillus* spores, or both.

In a further aspect, a pharmaceutical composition comprises fecal bacteria from at least 1, 2, 3, 4, 5, 6, 7, 8, 9, or 10 different families. In a further aspect, a pharmaceutical composition comprises fecal bacteria from multiple donors. In an aspect, a pharmaceutical composition provided or administered herein comprises a fecal microbiota comprising no greater than 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material. In another aspect, a pharmaceutical composition provided or administered herein comprises a fecal microbiota comprising no greater than 20%, 25%, 30%, 35%, 40%, 45%, 50%, 55%, 60%, 65%, 70%, 75%, 80%, 85%, 90%, or 95% weight non-living material/weight biological material. In another aspect, a pharmaceutical composition provided or administered herein comprises, consists of, or consists essentially of, particles of non-living material and/or particles of biological material of a fecal sample that passes through a sieve, a column, or a similar filtering device having a sieve, exclusion, or particle filter size of 2.0 mm, 1.0 mm, 0.5 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.2 mm. "Non-living material" does not include an excipient, e.g., a pharmaceutically inactive substance, such as a cryoprotectant, added to a processed fecal material. "Biological material" refers to the living material in fecal material, and includes microbes including prokaryotic cells, such as bacteria and archaea (e.g., living prokaryotic cells and spores that can sporulate to become living prokaryotic cells), eukaryotic cells such as protozoa and fungi, and viruses. In one embodiment, "biological material" refers to the living material, e.g., the microbes, eukaryotic cells, and viruses, which are present in the colon of a normal healthy human. In an aspect, a pharmaceutical composition provided or administered herein comprises an extract of human feces where the composition is substantially odorless. In an aspect, a pharmaceutical composition provided or administered herein comprises fecal material or a fecal floral preparation in a lyophilized, crude, semi-purified or purified formulation.

In an aspect, a fecal microbiota in a pharmaceutical composition comprises highly refined or purified fecal flora, e.g., substantially free of non-floral fecal material. In an aspect, a fecal microbiota can be further processed, e.g., to undergo microfiltration before, after, or before and after sieving. In another aspect, a highly purified fecal microbiota product is ultra-filtrated to remove large molecules but retain the pharmaceutical microflora, e.g., bacteria.

In another aspect, a fecal microbiota in a pharmaceutical composition used herein comprises or consists essentially of a substantially isolated or a purified fecal flora or entire (or substantially entire) microbiota that is (or comprises) an isolate of fecal flora that is at least about 90%, 91%, 92%, 93%, 94%, 95%, 96%, 97%, 98%, 99%, 99.5%, 99.6%, 99.7%, 99.8% or 99.9% isolated or pure, or having no more than about 0.1%, 0.2%, 0.3%, 0.4%, 0.5%, 0.6%, 0.7%, 0.8%, 0.9% or 1.0% or more non-fecal floral material; or, a substantially isolated, purified, or substantially entire microbiota as described in Sadowsky et al., WO 2012/122478 A1, or as described in Borody et al., WO 2012/016287 A2.

In an aspect, a fecal microbiota in a pharmaceutical composition comprises a donor's substantially entire or non-selected fecal microbiota, reconstituted fecal material, or synthetic fecal material. In another aspect, the fecal microbiota in a pharmaceutical composition comprises no antibiotic resistant population. In another aspect, a pharmaceutical composition comprises a fecal microbiota and is largely free of extraneous matter (e.g., non-living matter including acellular matter such as residual fiber, DNA, RNA, viral coat material, non-viable material; and living matter such as eukaryotic cells from the fecal matter's donor).

In an aspect, a fecal microbiota in a pharmaceutical composition used herein is derived from disease-screened fresh homologous feces or equivalent freeze-dried and reconstituted feces. In an aspect, a fresh homologous feces does not include an antibiotic resistant population. In another aspect, a fecal microbiota in a pharmaceutical composition is derived from a synthetic fecal composition. In an aspect, a synthetic fecal composition comprises a preparation of viable flora which preferably in proportional content, resembles normal healthy human fecal flora which does not include antibiotic resistant populations. Suitable microorganisms may be selected from the following: *Bacteroides, Eubacterium, Fusobacterium, Propionibacterium, Lactobacillus, Ruminococcus, Escherichia coli, Gemmiger, Clostridium, Desulfomonas, Peptostreptococcus, Bifidobacterium, Collinsella, Coprococcus, Dorea*, and *Ruminococcus*.

In one aspect, an exemplary therapeutic composition comprises starting material from a donor from a defined donor pool, where this donor contributes a stool that is centrifuged, then filtered with very high-level filtration using e.g., either metal sieving or Millipore filters, or equivalent, to ultimately permit only cells of bacterial origin to remain, e.g., often less than about 5 micrometers diameter. After the initial centrifugation, the solid material is separated from the liquid, and the solid is then filtered in progressively reducing size filters and tangential filters, e.g., using a Millipore filtration, and optionally, also comprising use of nano-membrane filtering. The filtering can also be done by sieves as described in WO 2012/122478, but in contrast using sieves that are smaller than 0.0120 mm, down to about 0.0110 mm, which ultimately result in having only bacterial cells present.

The supernatant separated during centrifugation is now taken and filtered progressively in a filtering, e.g., a Millipore filtering or equivalent systems, to end up with liquid which is finely filtered through an about 0.22 micron filter.

This removes all particulate matter including all living matter, including bacteria and viruses. The product then is sterile, but the aim is to remove the bacteria but to keep their secretions, especially antimicrobial bacteriocins, bacteria-derived cytokine-like products and all accompanying Biologically Active Molecules (BAMs), including: thuricin (which is secreted by bacilli in donor stools), bacteriocins (including colicin, troudulixine or putaindicine, or microcin or subtilosin A), lanbiotics (including nisin, subtilin, epidermin, mutacin, mersacidin, actagardine, cinnamycin), lacticins and other antimicrobial or anti-inflammatory compounds.

In one aspect, a therapeutic composition used here comprises a reconstituted fecal flora consisting essentially of a combination of a purified fecal microbiota and a non-cellular fecal filtrate. In another aspect, a therapeutic composition used here comprises a purified fecal microbiota supplemented with one or more non-cellular non-particulate fecal components. In one aspect, a therapeutic composition used here comprises one or more non-cellular non-particulate fecal components. In one aspect, one or more non-cellular non-particulate fecal components comprise synthetic molecules, biologically active molecules produced by a fecal microorganism, or both. In another aspect, one or more non-cellular non-particulate fecal components comprise biologically active proteins or peptides, micronutrients, fats, sugars, small carbohydrates, trace elements, mineral salts, ash, mucous, amino acids, nutrients, vitamins, minerals, or any combination thereof. In one aspect, one or more non-cellular non-particulate fecal components comprise one or more biologically active molecules selected from the group consisting of bacteriocin, lanbiotic, and lacticin. In another aspect, one or more non-cellular non-particulate fecal components comprise one or more bacteriocins selected from the group consisting of colicin, troudulixine, putaindicine, microcin, and subtilosin A. In one aspect, one or more non-cellular non-particulate fecal components comprise one or more lanbiotics selected from the group consisting of thuricin, nisin, subtilin, epidermin, mutacin, mersacidin, actagardine, and cinnamycin. In another aspect, one or more non-cellular non-particulate fecal components comprise an anti-spore compound, an antimicrobial compound, an anti-inflammatory compound, or any combination thereof. In a further aspect, one or more non-cellular non-particulate fecal components comprise an interleukin, a cytokine, a leukotriene, an eicosanoid, or any combination thereof.

In another aspect, a treatment method provided here comprises the use of both fecal bacterial cells, e.g., a partial or a complete representation of the human GI microbiota, and an isolated, processed, filtered, concentrated, reconstituted and/or artificial liquid component (e.g., fecal filtrate) of the flora (the microbiota) which comprises, among others ingredients, bacterial secretory products such as e.g., bacteriocins (proteinaceous toxins produced by bacteria, including colicin, troudulixine or putaindicine, or microcin or subtilosin A), lanbiotics (a class of peptide antibiotics that contain a characteristic polycyclic thioether amino acid lanthionine or methyllanthionine, and unsaturated amino acids dehydroalanine and 2-aminoisobutyric acid; which include thuricin (which is secreted by bacilli in donor stools), nisin, subtilin, epidermin, mutacin, mersacidin, actagardine, cinnamycin), a lacticin (a family of pore-forming peptidic toxins) and other antimicrobial or anti-inflammatory compounds and/or additional biologically active molecules (BAMs) produced by bacteria or other microorganisms of the microbiota, and/or which are found in the "liquid component" of a microbiota.

In one aspect, a fecal bacteria-based therapeutic composition is used concurrently with a fecal non-cellular filtrate-based therapeutic composition. In another aspect, a patient is treated with a first fecal non-cellular filtrate-based therapeutic composition before being given a second fecal bacteria-based therapeutic composition, or vice versa. In a further aspect, a treatment method comprises three steps: first, antibiotic pretreatment to non-selectively remove infectious pathogen(s); second, a fecal non-cellular filtrate-based treatment step to further suppress selected infectious pathogen(s); and third, giving the patient a fecal bacteria-based therapeutic composition to re-establish a functional intestinal microbiome.

In an aspect, a pharmaceutical composition is combined with other adjuvants such as antacids to dampen bacterial inactivation in the stomach. (e.g., Mylanta, Mucaine, Gastrogel). In another aspect, acid secretion in the stomach could also be pharmacologically suppressed using H2-antagonists or proton pump inhibitors. An example H2-antagonist is ranitidine. An example proton pump inhibitor is omeprazole. In an aspect, an acid suppressant is administered prior to administering, or in co-administration with, a pharmaceutical composition.

In an aspect, a pharmaceutical composition is in the form of: an enema composition which can be reconstituted with an appropriate diluent; enteric-coated capsules; enteric-coated microcapsules; acid-resistant tablet; acid-resistant capsules; acid-resistant microcapsules; powder for reconstitution with an appropriate diluent for naso-enteric infusion or colonoscopic infusion; powder for reconstitution with appropriate diluent, flavoring and gastric acid suppression agent for oral ingestion; powder for reconstitution with food or drink; or food or food supplement comprising enteric-coated and/or acid-resistant microcapsules of the composition, powder, jelly, or liquid.

In an aspect, a treatment method effects a cure, reduction of the symptoms, or a percentage reduction of symptoms of ulcerative colitis. The change of flora is preferably as "near-complete" as possible and, in an aspect, the flora is replaced by viable organisms which will crowd out any remaining, original flora. Typically the change in enteric flora comprises introduction of an array of predetermined flora into the gastro-intestinal system, and thus in a preferred form the method of treatment comprises substantially or completely displacing pathogenic enteric flora in patients requiring such treatment.

In another aspect, a pharmaceutical composition can be provided together with a pharmaceutically acceptable carrier. As used herein, a "pharmaceutically acceptable carrier" refers to a non-toxic solvent, dispersant, excipient, adjuvant, or other material which is mixed with a viable bacterium in order to permit the formation of a pharmaceutical composition, e.g., a dosage form capable of administration to the patient. A pharmaceutically acceptable carrier can be liquid (e.g., saline), gel or solid form of diluents, adjuvant, excipients or an acid resistant encapsulated ingredient. Suitable diluents and excipients include pharmaceutical grades of physiological saline, dextrose, glycerol, mannitol, lactose, starch, magnesium stearate, sodium saccharin, cellulose, magnesium carbonate, and the like, and combinations thereof. In another aspect, a pharmaceutical composition may contain auxiliary substances such as wetting or emulsifying agents, stabilizing or pH buffering agents. In an aspect, a pharmaceutical composition contains about 1%-5%, 5%-10%, 10%-15%, 15-20%, 20%-25%, 25-30%, 30-35%, 40-45%, 50%-55%, 1%-95%, 2%-95%, 5%-95%, 10%-95%, 15%-95%, 20%-95%, 25%-95%, 30%-95%, 35%-95%, 40%-95%, 45%-95%, 50%-95%, 55%-95%, 60%-95%, 65%-95%, 70%-95%, 45%-95%, 80%-95%, or 85%-95% of active ingredient. In an aspect, a pharmaceutical composition contains about 2%-70%, 5%-60%, 10%-50%, 15%-40%, 20%-30%, 25%-60%, 30%-60%, or 35%-60% of active ingredient.

In an aspect, a pharmaceutical composition can be incorporated into tablets, drenches, boluses, capsules or premixes. Formulation of these active ingredients into such dosage forms can be accomplished by means of methods well known in the pharmaceutical formulation arts. See, e.g., U.S. Pat. No. 4,394,377. Filling gelatin capsules with any desired form of the active ingredients readily produces capsules. If desired, these materials can be diluted with an inert powdered diluent, such as sugar, starch, powdered milk, purified crystalline cellulose, or the like to increase the volume for convenience of filling capsules.

In an aspect, conventional formulation processes can be used to prepare tablets containing a pharmaceutical composition. In addition to the active ingredients, tablets may contain a base, a disintegrator, an absorbent, a binder, and a lubricant. Typical bases include lactose, sugar, sodium chloride, starch and mannitol. Starch is also a good disintegrator as is alginic acid. Surface-active agents such as sodium lauryl sulfate and dioctyl sodium sulphosuccinate are also sometimes used. Commonly used absorbents include starch and lactose. Magnesium carbonate is also useful for oily substances. As a binder there can be used, for example, gelatin, gums, starch, dextrin, polyvinyl pyrrolidone and various cellulose derivatives. Among the commonly used lubricants are magnesium stearate, talc, paraffin wax, various metallic soaps, and polyethylene glycol.

In an aspect, for preparing solid compositions such as tablets, an active ingredient is mixed with a pharmaceutical carrier, e.g., conventional tableting ingredients such as corn starch, lactose, sucrose, sorbitol, talc, stearic acid, magnesium stearate, dicalcium phosphate or gums, or other pharmaceutical diluents, e.g. water, to form a solid preformulation composition containing a homogeneous mixture of a composition of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing a desired amount of an active ingredient (e.g., at least about $10^5$, $10^6$, $10^7$, $10^8$, $10^9$, $10^{10}$, $10^{11}$, $10^{12}$, or $10^{13}$ cfu). A pharmaceutical composition used herein can be flavored.

In an aspect, a pharmaceutical composition can be a tablet or a pill. In an aspect, a tablet or a pill can be coated or otherwise compounded to provide a dosage form affording the advantage of prolonged action. For example, a tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

In an aspect, a pharmaceutical composition can be a drench. In an aspect, a drench is prepared by choosing a saline-suspended form of a pharmaceutical composition. A water-soluble form of one ingredient can be used in conjunction with a water-insoluble form of the other by preparing a suspension of one with an aqueous solution of the other. Water-insoluble forms of either active ingredient may be prepared as a suspension or in some physiologically acceptable solvent such as polyethylene glycol. Suspensions of water-insoluble forms of either active ingredient can be prepared in oils such as peanut, corn, sesame oil or the like; in a glycol such as propylene glycol or a polyethylene glycol; or in water depending on the solubility of a particular active ingredient. Suitable physiologically acceptable adjuvants may be necessary in order to keep the active ingredients suspended. Adjuvants can include and be chosen from among the thickeners, such as carboxymethylcellulose, polyvinyl pyrrolidone, gelatin and the alginates. Surfactants generally will serve to suspend the active ingredients, particularly the fat-soluble propionate-enhancing compounds. Most useful for making suspensions in liquid nonsolvents are alkylphenol polyethylene oxide adducts, naphthalene-sulfonates, alkylbenzene-sulfonates, and the polyoxyethylene sorbitan esters. In addition many substances, which affect the hydrophilicity, density and surface tension of the liquid, can assist in making suspensions in individual cases. For example, silicone anti-foams, glycols, sorbitol, and sugars can be useful suspending agents.

In an aspect, a pharmaceutical composition comprises at least about $10^5$, $10^6$, $10^7$, $10^8$, $10^9$, $10^{10}$, $10^{11}$, $10^{12}$, or $10^{13}$ cfu. In another aspect, a pharmaceutical composition comprises at most about $10^5$, $10^6$, $10^7$, $10^8$, $10^9$, $10^{10}$, $10^{11}$, $10^{12}$, $10^{13}$ or $10^{14}$ cfu.

In another aspect, a pharmaceutical composition comprises at least about $10^5$, $10^6$, $10^7$, $10^8$, $10^9$, $10^{10}$, $10^{11}$, $10^{12}$, or $10^{13}$ cells. In another aspect, a pharmaceutical composition comprises at most about $10^5$, $10^6$, $10^7$, $10^8$, $10^9$, $10^{10}$, $10^{11}$, $10^{12}$, $10^{13}$ or $10^{14}$ cells.

In another aspect, a pharmaceutical composition and methods thereof comprise the following embodiments:

Embodiment 1. A pharmaceutical composition comprising viable non-pathogenic bacteria from one or more first microbial taxa selected from the group consisting of *Clostridium* cluster XVIII, *Ruminococcus*, *Lachnospiraceae*, *Roseburia inulinivorans*, *Eubacterium hallii*, and any combination thereof, wherein said pharmaceutical composition contains no bacteria from one or more second microbial taxa selected from the group consisting of *Fusobacterium*, *Sutterella*, *Haemophilus*, *Escherichia*, *Megamonas*, *Clostridium* cluster XIVa, *Prevotella*, *Dialister*, *Veillonella*, and *Bilophila*.

Embodiment 2. A pharmaceutical composition comprising viable non-pathogenic bacteria from one or more first microbial taxa selected from the group consisting of *Clostridium* cluster XVIII, *Ruminococcus*, *Lachnospiraceae*, *Roseburia inulinivorans*, and *Eubacterium hallii*, wherein said pharmaceutical composition contains no bacteria from a second microbial taxon selected from the group consisting of *Fusobacterium gonidiaformans*, *Prevotella copri*, and *Sutterella wadsworthensis*.

Embodiment 3. A pharmaceutical composition comprising a substantially entire fecal microbiota supplemented, enhanced, or spiked with viable non-pathogenic bacteria from one or more microbial taxa selected from the group consisting of *Clostridium* cluster XVIII, *Ruminococcus*, *Lachnospiraceae*, *Roseburia inulinivorans*, and *Eubacterium hallii*.

Embodiment 4. A pharmaceutical composition comprising a fecal microbe preparation having a relative abundance ratio of 2 or more between a first microbial taxon selected from the group consisting of *Clostridium* cluster XVIII, *Ruminococcus, Lachnospiraceae, Roseburia inulinivorans*, and *Eubacterium hallii*, and a second microbial taxon selected from the group consisting of *Fusobacterium, Sutterella, Haemophilus, Escherichia, Megamonas, Clostridium* cluster XIVa, *Prevotella, Dialister, Veillonella*, and *Bilophila*.

Embodiment 5. The pharmaceutical composition of embodiment 4, wherein said second microbial taxon is selected from the group consisting of *Fusobacterium gonidiaformans, Prevotella copri*, and *Sutterella wadsworthensis*.

Embodiment 6. The pharmaceutical composition of embodiment 4, wherein said relative abundance ratio is selected from the group consisting of 3 or more, 4 or more, 5 or more, 10 or more, 20 or more, 30 or more, 50 or more, 100 or more, and 200 or more.

Embodiment 7. A pharmaceutical composition comprising a substantially entire fecal microbiota supplemented, enhanced, or spiked with viable non-pathogenic bacteria from a microbial taxon selected from the group consisting of *Bacteroides* OTU187, *Bacteroides fragilis*, and *Bacteroides finegoldii*.

Embodiment 8. A pharmaceutical composition comprising viable non-pathogenic bacteria from a first microbial taxon selected from the group consisting of *Bacteroides* OTU187, *Bacteroides fragilis*, and *Bacteroides finegoldii*.

Embodiment 9. The pharmaceutical composition of embodiment 8, wherein said pharmaceutical composition contains no bacteria from a second microbial taxon selected from the group consisting of *Fusobacterium gonidiaformans, Prevotella copri*, and *Sutterella wadsworthensis*.

Embodiment 10. The pharmaceutical composition of embodiment 8, wherein said pharmaceutical composition contains no bacteria from a second microbial taxon selected from the group consisting of *Clostridium* cluster XIVa (OTU173), *Streptococcus* (OTU56), *Sutterella wadsworthensis, Bacteroides uniformis*, and *Bacteroides coprocola*.

Embodiment 11. The pharmaceutical composition of any one of the preceding embodiments, wherein said viable non-pathogenic bacteria or said fecal microbe preparation are from a synthetic culture.

Embodiment 12. A pharmaceutical composition comprising a fecal microbiota preparation having a suppressed, decreased, reduced, minimized, or undetectable level of a microbial taxon selected from the group consisting of *Clostridium* cluster XIVa (OTU173), *Streptococcus* (OTU56), *Sutterella wadsworthensis, Bacteroides uniformis*, and *Bacteroides coprocola*.

Embodiment 13. The pharmaceutical composition of any one of embodiments 1 to 12, wherein said pharmaceutical composition is in an anaerobic package or container.

Embodiment 14. The pharmaceutical composition of any one of embodiments 1 to 12, wherein said pharmaceutical composition is in a liquid, frozen, freeze-dried, spray-dried, lyophilized, or powder form.

Embodiment 15. The pharmaceutical composition of any one of embodiments 1 to 12, wherein said pharmaceutical composition comprises an excipient, a saline, a buffer, a buffering agent, or a fluid-glucose-cellobiose agar (RGCA) media.

Embodiment 16. The pharmaceutical composition of any one of embodiments 1 to 12, wherein said pharmaceutical composition is formulated as an enteric coated capsule or microcapsule, an acid-resistant capsule or microcapsule, an enteric coated tablet, an acid-resistant tablet, a powder suitable for reconstitution, a naso-duodenal infusion, or for delivery in the form of an enema or a colonoscopic infusion.

Embodiment 17. The pharmaceutical composition of any one of embodiments 1 to 12, wherein said pharmaceutical composition is formulated as a delayed or gradual enteric release form.

Embodiment 18. The pharmaceutical composition of any one of embodiments 1 to 12, wherein said pharmaceutical composition is administered together with a food, a liquid beverage, a food additive, a dairy-based product, a soy-based product or a derivative thereof, a jelly, or a yogurt.

Embodiment 19. The pharmaceutical composition of any one of embodiments 1 to 12, wherein said pharmaceutical composition comprises a cryoprotectant.

Embodiment 20. The pharmaceutical composition of any one of embodiments 1 to 12, wherein said pharmaceutical composition comprises a cryoprotectant comprises polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof.

Embodiment 21. The pharmaceutical composition of any one of embodiments 1 to 12, wherein said pharmaceutical composition further comprises an acid suppressant, an antacid, an H2 antagonist, a proton pump inhibitor or a combination thereof.

Embodiment 22. A method for treating ulcerative colitis (UC) in a patient in need thereof, said method comprising administering to said patient the pharmaceutical composition of any one of embodiments 1 to 21.

Embodiment 23. A method for modulating a metabolic marker from a pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, and starch degradation, in a UC patient in need thereof, said method comprising administering to said patient the pharmaceutical composition of any one of embodiments 1 to 21.

Embodiment 24. A method for treating UC in a patient in need thereof, comprising administering to said patient a modulator of a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, and any combination thereof.

Embodiment 25. The method of embodiment 24, wherein said modulator comprises the pharmaceutical composition of any one of embodiments 1 to 21.

Embodiment 26. The method of embodiment 24, wherein said method comprises upregulating or promoting said metabolic pathway in said patient's fecal microbiome.

Embodiment 27. A method for treating UC in a patient in need thereof, comprising administering the pharmaceutical composition of any one of embodiments 1 to 21 to said patient, wherein said patient is pretested for one or more markers from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, starch degradation, heme biosynthesis, lipopolysaccharide biosynthesis, ubiquinone and other terpenoid quinine biosynthesis, lysine biosynthesis, and oxidative phosphorylation pathway.

Embodiment 28. A method for treating UC in a patient in need thereof, comprising administering the pharmaceutical composition of any one of embodiments 1 to 21 to said patient, wherein said patient is pretested for the relative abundance of *Fusobacterium gonidiaformans*, *Prevotella copri*, or *Sutterella wadsworthensis*.

Embodiment 29. A method for treating UC in a patient in need thereof, comprising administering the pharmaceutical composition of any one of embodiments 1 to 21 to said patient, wherein said patient comprises a relative abundance of *Fusobacterium gonidiaformans*, *Prevotella copri*, or *Sutterella wadsworthensis* below a pre-determined highest limit.

Embodiment 30. A method for treating UC in a patient in need thereof, comprising administering the pharmaceutical composition of any one of embodiments 1 to 21 to said patient, wherein said patient comprises a relative abundance of one or more microbial taxa selected from the group consisting of *Fusobacterium*, *Sutterella*, *Haemophilus*, *Escherichia*, *Megamonas*, *Clostridium* cluster XIVa, *Prevotella*, *Dialister*, *Veillonella*, and *Bilophila*, below a pre-determined highest limit.

Embodiment 31. A method for treating UC in a patient in need thereof, comprising administering the pharmaceutical composition of any one of embodiments 1 to 21 to said patient, wherein said patient comprises one or more markers, above a pre-determined lowest level, from a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, and starch degradation.

Embodiment 32. A method for treating UC in a patient in need thereof, comprising administering the pharmaceutical composition of any one of embodiments 1 to 21 to said patient, wherein said patient comprises one or more markers, below a pre-determined highest level, from a metabolic pathway selected from the group consisting of heme biosynthesis, lipopolysaccharide biosynthesis, ubiquinone and other terpenoid quinine biosynthesis, lysine biosynthesis, and oxidative phosphorylation pathway.

Embodiment 33. A method for modulating a marker from a pathway selected from the group consisting of heme biosynthesis, lipopolysaccharide biosynthesis, ubiquinone and other terpenoid quinine biosynthesis, lysine biosynthesis, and oxidative phosphorylation pathway, in a UC patient in need thereof, said method comprising administering to said patient the pharmaceutical composition of any one of embodiments 1 to 21.

Embodiment 34. The method of any one of embodiments 27 to 33, wherein said one or more markers are metabolic markers.

Embodiment 35. The method of any one of embodiments 27 to 33, wherein said one or more markers comprise one or more metabolic pathway genes.

Embodiment 36. A method for treating UC in a patient in need thereof, comprising administering to said patient a modulator of a metabolic pathway selected from the group consisting of heme biosynthesis, lipopolysaccharide biosynthesis, ubiquinone and other terpenoid quinine biosynthesis, lysine biosynthesis, oxidative phosphorylation pathway, and any combination thereof.

Embodiment 37. The method of embodiment 36, wherein said modulator comprises the pharmaceutical composition of any one of embodiments 1 to 21.

Embodiment 38. The method of embodiment 36, wherein said method comprises downregulating or suppressing said metabolic pathway in said patient's fecal microbiome.

Embodiment 39. A method for producing a pharmaceutical composition, said method comprising
a) determining in a candidate fecal microbe source material the relative abundance of one or more bacterial markers selected from the group consisting of *Bacteroides* OTU187, *Bacteroides fragilis*, *Bacteroides finegoldii*, *Clostridium* cluster XIVa (OTU173), *Streptococcus* (OTU56), *Sutterella wadsworthensis*, *Bacteroides uniformis*, and *Bacteroides coprocola*;
b) selecting said candidate fecal microbe source material if the relative abundance of *Bacteroides* OTU187, *Bacteroides fragilis*, or *Bacteroides finegoldii* is above a pre-determined lowest limit, and/or if the relative abundance of *Clostridium* cluster XIVa (OTU173), *Streptococcus* (OTU56), *Sutterella wadsworthensis*, *Bacteroides uniformis*, or *Bacteroides coprocola* is below a pre-determined highest limit; and
c) producing a pharmaceutical composition from said selected fecal microbe source material.

Embodiment 40. The method of embodiment 39, wherein said pharmaceutical composition is for treating UC.

Embodiment 41. A method for selecting a fecal donor, said method comprising
a) determining in a candidate fecal donor the relative fecal abundance of one or more bacterial markers selected from the group consisting of *Bacteroides* OTU187, *Bacteroides fragilis*, *Bacteroides finegoldii*, *Clostridium* cluster XIVa (OTU173), *Streptococcus* (OTU56), *Sutterella wadsworthensis*, *Bacteroides uniformis*, and *Bacteroides coprocola*; and
b) selecting said candidate fecal donor for future fecal donation, if the relative fecal abundance of *Bacteroides* OTU187, *Bacteroides fragilis*, or *Bacteroides finegoldii* is above a pre-determined lowest limit, and/or if the relative fecal abundance of *Clostridium* cluster XIVa (OTU173), *Streptococcus* (OTU56), *Sutterella wadsworthensis*, *Bacteroides uniformis*, or *Bacteroides coprocola* is below a pre-determined highest limit.

Embodiment 42. The method of embodiment 41, wherein said donor is selected for producing a pharmaceutical composition for treating UC.

Embodiment 43. A method for selecting a fecal microbe source material, said method comprising
a) Determining in a candidate fecal microbe source material the relative abundance of one or more markers from a metabolic pathway selected from the group consisting of fatty acid biosynthesis, propanoate metabolism, secondary bile acid biosynthesis, glycerophospholipid metabolism, and biosynthesis of ansamycins; and
b) selecting said candidate fecal microbe source material if the relative abundance of said one or more markers is above a pre-determined lowest limit.

Embodiment 44. The method of embodiment 43, wherein said fecal microbe source material is selected for producing a pharmaceutical composition for treating UC.

Embodiment 45. The method of embodiment 43, wherein said one or more markers are metabolic markers.

Embodiment 46. The method of embodiment 43, wherein said one or more markers comprise one or more metabolic pathway genes.

Embodiment 47. A method for selecting a fecal microbe source material, said method comprising
a) determining in a candidate fecal microbe source material the relative abundance of one or more markers from a metabolic pathway selected from the group consisting of terpenoid backbone biosynthesis, bacterial chemotaxis, and heme biosynthesis; and b) selecting said candidate fecal microbe source material if the relative abundance of said one or more markers is below a pre-determined highest limit.

Embodiment 48. The method of embodiment 47, wherein said fecal microbe source material is selected for producing a pharmaceutical composition for treating UC.

Embodiment 49. The method of embodiment 47, wherein said one or more markers are metabolic markers.

Embodiment 50. The method of embodiment 47, wherein said one or more markers comprise one or more metabolic pathway genes.

Embodiment 51. A method for selecting a UC patient for a fecal microbe-based therapy, said method comprising
a) determining in a UC patient one or more markers for the relative fecal abundance of a taxon selected from the group consisting of *Clostridium* cluster XVIII, *Ruminococcus*, *Lachnospiraceae*, *Roseburia inulinivorans*, *Eubacterium hallii*, *Fusobacterium*, *Sutterella*, *Haemophilus*, *Escherichia*, *Megamonas*, *Clostridium* cluster XIVa, *Prevotella*, *Dialister*, *Veillonella*, and *Bilophila*; and
b) selecting said UC patient for a fecal microbe-based therapy, if the relative fecal abundance of *Clostridium* cluster XVIII, *Ruminococcus*, *Lachnospiraceae*, *Roseburia inulinivorans*, or *Eubacterium hallii* is above a pre-determined lowest limit, and/or if the relative fecal abundance of *Fusobacterium*, *Sutterella*, *Haemophilus*, *Escherichia*, *Megamonas*, *Clostridium* cluster XIVa, *Prevotella*, *Dialister*, *Veillonella*, or *Bilophila* is below a pre-determined highest limit.

Embodiment 52. A method for selecting a UC patient for a fecal microbe-based therapy, said method comprising
a) determining in a UC patient one or more markers for the relative fecal abundance of a taxon selected from the group consisting of *Fusobacterium gonidiaformans*, *Prevotella copri*, and *Sutterella wadsworthensis*; and
b) selecting said UC patient for a fecal microbe-based therapy, if the relative fecal abundance of said taxon is below a pre-determined highest limit.

Embodiment 53. A method for selecting a UC patient for a fecal microbe-based therapy, said method comprising
a) determining in a UC patient the relative fecal abundance of one or more markers for a metabolic pathway selected from the group consisting of benzoate degradation, glycerophospholipid metabolism, secondary bile acid biosynthesis, ppGpp biosynthesis, pyruvate fermentation to acetate and lactate, short chain fatty acid biosynthesis, biosynthesis of ansamycins, and starch degradation; and
b) selecting said UC patient for a fecal microbe-based therapy, if the relative fecal abundance is above a pre-determined lowest limit.

Embodiment 54. A method for selecting a UC patient for a fecal microbe-based therapy, said method comprising
a) determining in a UC patient the relative fecal abundance of one or more markers for a metabolic pathway selected from the group consisting of heme biosynthesis, lipopolysaccharide biosynthesis, ubiquinone and other terpenoid quinine biosynthesis, lysine biosynthesis, and oxidative phosphorylation pathway; and
b) selecting said UC patient for a fecal microbe-based therapy, if the relative fecal abundance is below a pre-determined highest limit.

Embodiment 55. The method of any one of embodiments 51 to 54, further comprising subjecting said selected UC patient to a fecal microbe-based therapy.

EXAMPLES

Example 1

Trial Design and Microbiome Characterization of a FMT-Based Therapy of UC

Patients with active UC are randomised in a double-blind controlled trial to intensive multi-donor FMT or placebo enemas 5 days per week for 8 weeks. Patients randomised to placebo are eligible to receive open-label FMT after the double-blind study period. FMT infusions are constituted from the blended homogenised stool of 3 to 7 unrelated donors, to increase microbial heterogeneity. Each patient receives all their FMT infusions from the same donor batch. See ClinicalTrials.gov at NCT01896635 and Paramsothy et al., *Lancet* 2017; 389: 1218-28, both of which are incorporated by reference in their entirety.

Fecal samples are collected from individual donors, multi-donor FMT batches and study patients for molecular microbiological analyses and gastrointestinal microbial community profiling. Donor fecal samples (n=105) are collected from the 14 individual donors (n=55) and the 21 multi-donor FMT batches (n=50); eight samples are also taken from 4 placebo batches to serve as control.

Seventy study patients provide a total of 314 fecal samples at screening, then every 4 weeks during treatment (blinded, and open label if applicable) and eight weeks after completing blinded or open-label FMT therapy. These patients also contribute 160 colonoscopic large bowel biopsies at study entry prior to treatment, after eight weeks of active or placebo treatment (the primary study endpoint), and where relevant after a further eight weeks of open-label treatment.

All samples are stored at −80° C. immediately after collection until nucleic acid extraction. Fecal samples are homogenised and both DNA and RNA extracted using the MOBIO PowerViral RNA/DNA Isolation kit. Fecal RNA is then isolated from DNA using the MOBIO On-Spin Column DNase kit and Bioline Isolate II RNA micro clean-up kit. Colonic biopsy samples are homogenised and bacterial DNA and RNA extracted using the Macherey-Nagel RNA Isolation Kit. Colonic RNA is then isolated from DNA using the MOBIO On-Spin Column DNase kit and Macherey-Nagel RNA clean-up kit. Fecal and colonic RNA is then converted to cDNA using the SensiFAST cDNA Synthesis Kit (Bioline).

The 16S rRNA gene fragment of the extracted DNA and RNA converted to cDNA is amplified using the Immolase DNA polymerase (95° C. for 10 min, 35 cycles of 94° C. for 30 s 55° C. for 10 s, 72° C. for 45 s, followed by a final step of 72° C. for 10 min) and the primers F27-519R. Sample indices and Illumina sequencing adapters are attached using the Nextera XT Index Kit according to the manufacturer's instructions. Amplicon sequencing is performed with the Illumina MiSeq Reagent kit v3 (2×300 bp) at the Ramaciotti Centre for Genomics. Shotgun metagenomics is performed on DNA extracted from 285 donor and patient fecal samples using Nextera XT DNA library prep kit and 2×250 bp HiSeq 2500 chemistry. This results in five datasets including fecal 16S DNA, fecal 16S cDNA, colonic biopsy 16S DNA, colonic biopsy 16S cDNA, and fecal shotgun DNA.

Quality filtering of 16S rRNA sequences is conducted using software package mothur (Schloss (2009). "Introducing mothur: open-source, platform-independent, community-supported software for describing and comparing microbial communities." *Applied and Environmental Micro-*

*biology* 75(23): 7537-7541) and follows the mothur MiSeq SOP (Kozich (2013). "Development of a Dual-Index Sequencing Strategy and Curation Pipeline for Analyzing Amplicon Sequence Data on the MiSeq Illumina Sequencing Platform." *Applied and Environmental Microbiology* 79(17): 5112-5120). Paired-end sequences are merged into contigs, and poor quality contigs removed based on alignment quality and ambiguous base calls. A multiple sequence alignment is constructed using the SILVA SEED 16S rRNA reference alignment (Quast The SILVA ribosomal RNA gene database project: improved data processing and web-based tools. *Nucleic Acids Res* 2013; 41: D590-6), and poorly aligned sequences removed. To eliminate artefacts of sequencing at high frequency, rare sequences with high similarity to abundant sequences are clustered together. Chimeric sequences are removed using uchime (Edgar *Bioinformatics,* 2011; 27: 2194-200). Sequences are taxonomically classified using the Ribosomal Database project taxonomic outline (Wang *Appl Environ Microbiol,* 2007; 73: 5261-7) and those without classification at the kingdom level (unknown) or classified as mitochondrial or chloroplast are removed. Quality filtered sequences are then clustered into operational taxonomic units (OTUs) at 97% similarity using the opti-dust average neighbour algorithm (Westcott OptiClust, an Improved Method for Assigning Amplicon-Based Sequence Data to Operational Taxonomic Units. *mSphere* 2017; 2), and consensus taxonomies of the OTUs obtained using the classifications of sequences within each OTU. The resulting OTU count by sample data matrix is used for data analysis.

Shotgun metagenomic DNA sequence reads are first analysed with DeconSeq (Schmieder Fast identification and removal of sequence contamination from genomic and metagenomic datasets. *PLoS One* 2011; 6: e17288) for identification and filtering of human DNA sequences. Sequencing reads are assessed for quality using FastQC (version 0.11.2). SolexaQA is then applied to calculate sequence quality statistics and perform quality filtering of the Illumina reads. Paired-end raw reads are trimmed with the BWA trimming mode at a threshold of Q13 (P=0.05) using the read trimmer module DynamicTrim. Filtered reads that are less than 50 bp in length are then discarded using LengthSort. The average microbial read counts per sample are 4,590,171±119,145 reads. MetaPhlAn2 (Truong et al. MetaPhlAn2 for enhanced metagenomic taxonomic profiling. *Nat Methods* 2015; 12: 902-3) is employed to generate taxonomic profiles from the shotgun reads, while HUMAnN2 (HMP Unified Metabolic Analysis Network) (Hall et al. A novel Ruminococcus gnavus clade enriched in inflammatory bowel disease patients. *Genome medicine* 2017; 9: 103) is used to determine the metabolic contributions within the samples. The HUMAnN2 pipeline involved mapping of the metagenomic reads against Uniref orthologous gene family, MetCyc UniPathway, and KEGG.

During the initial double-blind FMT trial patients are allocated to active FMT treatment or placebo groups (FMT: two levels—Placebo or FMT, factor type—fixed) and each patient is sampled at three time points over eight weeks (Time: three levels—0, 4 and 8 weeks, factor type—fixed). Each patient is included in the experimental design as a random factor. After 8 weeks, the initial placebo group receive active FMT and are sampled further at weeks 4 and 8 of the open-label (non-blind) period. All patients receiving active FMT are also sampled at 8 weeks after completing active FMT therapy (blinded or open-label).

To examine which microbial taxa differed between patients showing remission, data are combined from the blinded and open-label study periods, and then groups are created based on remission (Remission, two levels—Yes or No, factor type—fixed) and treatment group (FMT: three levels—Placebo, FMTblind or FMTopen). We then examined the effect of different categories of remission, including remission within the blinded trial (Remission among Placebo and FMTblind), and regardless of study phase (Remission among Placebo, FMTblind and FMTopen). Analyses are made using four different endpoint classifications—primary endpoint, clinical remission, endoscopic response, and endoscopic remission (steroid free endoscopic Mayo score of 0) (Paramsothy et al., *Lancet* 2017; 389: 1218-28).

The effect of donor batch on remission is examined by allocating donor batches into two groups based on the number of patient remissions observed for each batch (DonorRemission, two levels—Yes or No, factor type—fixed). If more than 50% of the patients receiving a particular donor batch showed remission, the donor batch is allocated to the DonorRemission=Yes group, while all other donors are allocated to the DonorRemission=No group.

Microbial communities are examined with respect to the above analyses in terms of alpha-diversity and beta-diversity, as well as comparing each taxon individually. Prior to diversity comparisons, the OTU counts are rarefied to account for uneven sequencing depths among samples (35, 371,968 total clean reads; rarefied to 6447 clean reads/ sample). Linear mixed models (LMMs) are used to examine the effects of the various predictors mentioned above. Models are created using the R packages LME4 (Bates et al., (2015). "Fitting Linear Mixed-Effects Models Using lme4." Journal of Statistical Software 2015 67(1): 48) and lmerTest (Kuznetsova et al., (2017). "lmerTest Package: Tests in Linear Mixed Effects Models." Journal of Statistical Software 82(13): 1-26).

The Bray-Curtis (BC) dissimilarity coefficient for beta-diversity comparisons is employed, and prior to calculation of BC dissimilarities, OTU counts are transformed into square-root relative abundances. The BC distance matrix is visualized using non-metric multidimensional scaling (nMDS). PERMANOVA is used to examine the effects of the various predictors mentioned above. Dissimilarities, Figures and models are created using the R package 'vegan' (Oksanen, (2017) *Vegan: Community Ecology Package*). For per taxon comparisons, un-rarefied OTU counts are used in negative binomial generalised linear models (GLMs) with the sample totals used as an offset term. Contrasts are employed to examine the comparisons of interest within each analysis. Models are created using the R package DESeq2 (Love et al., Moderated estimation of fold change and dispersion for RNA-seq data with DESeq2." Genome Biology 15(12): 550). For confirmation, Linear Discriminant Analysis Effect Size (LEfSe) analyses are also performed (Segata et al. Metagenomic biomarker discovery and explanation. *Genome biology* 2011; 12: R60).

Example 2

Specific Bacterial Taxa Associated with Therapeutic Outcome

Despite FMT therapy, five patients do not appear to have a major change in overall microbial structure, with their baseline samples clustering tightly with their samples during and post-FMT. Surprisingly, one of these patients achieves the primary outcome, and on further analysis, their overall microbiota structure is similar at baseline and during and post-FMT except for replacement of key species *Bacteroides*

*clarus* (11.5% to 0.06%) and *Akkermansia muciniphila* (11.1% to 0%) with *Faecalibacterium prausnitzii* (4.9% to 11.1%), *Eubacterium rectale* (0.19% to 9.9%), and *Eubacterium siraeum* (0.96% to 14.2%).

To identify specific microbial taxa significantly associated with achieving or not achieving the primary outcome across all patients, the abundances of each OTU is modeled in each dataset using negative binomial GLMs with remission as a predictor and presented the most discriminating taxa as potential biomarkers. A range of microbial taxa associated with lack of remission including *Fusobacterium, Sutterella, Haemophilus, Escherichia, Megamonas, Clostridium* cluster XIVa, *Prevotella, Dialister, Veillonella* and *Bilophila*, and these associations are in some datasets clearer when blinded and open label patients are stratified. The most consistent association with lack of achieving primary outcome is with *Fusobacterium gonidiaformans*, with this taxon identified in fecal 16S rRNA gene, mucosal 16S rRNA gene and transcript, and shotgun sequencing data. Of interest, *Prevotella* OTU2 (*Prevotella copri* in shotgun data) appears to flourish in several patients with FMT; however, this OTU is associated with lack of remission and patients who achieve remission tend to be those who resist dominance by *Prevotella*, having lower levels relative to patients who do not achieve remission.

There is less consistency in taxa associated with remission across the datasets—these most commonly involved members of Firmicutes e.g. *Clostridium* cluster XVIII, *Ruminococcus, Lachnospiraceae, Roseburia inulinivorans,* and *Eubacterium hallii*. The associations among a range of these microbial taxa and primary outcome are confirmed using LEfSe.

To further examine the consistency of these associations, GLMs is used with three other therapeutic outcomes including the stricter endpoint of complete endoscopic remission (steroid free endoscopic Mayo 0), endoscopic response, and clinical remission. *Fusobacterium gonidiaformans, Sutterella wadsworthensis, Haemophilus, Escherichia, Megamonas, Clostridium* cluster XIVa, *Prevotella, Dialister, Veillonella* and *Bilophila* are all consistently associated with lack of endoscopic remission. Analyses of endoscopic response and clinical remission are less consistent, likely due to the less strict nature of these endpoints; however, a range of the above taxa (including *Fusobacterium, Haemophilus, Escherichia, Dialister* and *Veillonella*) are still associated with negative outcomes.

Example 3

FMT Results in Functional Changes Associated with Therapeutic Outcome

Microbial functional changes across FMT therapy and therapeutic outcome are characterised, with analysis focusing on outputs from KEGG and MetaCyc pathways. FMT, but not placebo, resulted in significant changes in microbial KEGG ($F_{1,42}$=2.5, P=0.027) and MetaCyc pathways ($F_{1,43}$=2.3, P=0.010). Despite intense FMT, patient microbial functional profiles remain significantly different to that of the donors (475)=2.0, P=0.001, Permutations=999). Similar to the taxonomic profiles, FMT increases homogeneity (reduced dispersion) in the functional profiles across patient samples, but not to the level of individual donors or donor batches. Due to the significant patient variability that is observed in the data, a constraint on the factor 'patient' is applied, which shows a clearer delineation between FMT and placebo.

Specific pathways associated with primary outcome are then identified using GLMs. Pathways such as benzoate degradation, glycerophospholipid metabolism, secondary bile acid biosynthesis, ppGpp biosynthesis, pyruvate fermentation to acetate and lactate (short chain fatty acid biosynthesis), biosynthesis of ansamycins, and starch degradation are all associated with positive primary outcome. Taxa contributing to beneficial pathways included *Eubacterium, Ruminococcus, Lachnospiraceae, Roseburia, Dorea* and *Coprococcus*, consistent with the taxonomic analysis associating these species with positive therapeutic outcome. Furthermore, the relationship between short chain fatty acid biosynthesis and positive primary outcome is confirmed in the predicted metagenome (PICRUSt) of the mucosal microbiome. In contrast, heme biosynthesis, lipopolysaccharide biosynthesis, ubiquinone and other terpenoid quinine biosynthesis, lysine biosynthesis and oxidative phosphorylation pathways are all associated with negative primary outcome. The relationships between a range of these pathways and primary outcome are confirmed using LEfSe.

Similar to the taxonomic analysis, the analyses are replicated against the three other therapeutic outcomes of complete endoscopic remission, endoscopic response, and clinical remission. The results from these endpoints show consistent associations as those observed for the primary study outcome.

Example 4

Donor Taxonomic and Functional Profiles Associated with Therapeutic Outcome

Despite FMT therapy over 8 weeks, patient taxonomic and functional profiles remain different to those of individual donors and donor batches. Thus, specific factors associated with donor suitability are evaluated by analysis of the donor fecal samples (16S rRNA gene and transcript, as well as shotgun metagenomic datasets) relative to the four different therapeutic outcomes.

Donor batches are categorised based on the total number of samples and number of patients that achieved a positive primary outcome, with donor batches leading to >50% remission classified as effective and the rest as ineffective. α-diversity and β-diversity within effective and ineffective batches are compared in all datasets, with no clear patterns emerging between the two groups. While some differences in global β-diversity are observed ($F_{1,18}$=1.7, P=0.071), this is likely due to the high inter-donor variability.

Specific taxonomic differences between effective and ineffective batches are then analysed using GLMs. *Bacteroides* OTU187 is in higher abundance in effective batches, and consistently *Bacteroides fragilis*, as well as *Bacteroides finegoldii*, are identified as taxonomic markers in these batches. In contrast, *Bacteroides uniformis* and *Bacteroides coprocola* are associated with ineffective batches. Other donor microbial taxa associated with ineffective batches included *Clostridium* cluster XIVa (OTU173), a taxon that is associated with negative primary outcomes, and *Streptococcus* (OTU56), which is found in both the 16S rRNA gene and transcript datasets.

No clear differences in global pathway compositions are found between effective and ineffective batches. However, a range of pathways are identified to be in higher abundance in either effective or ineffective batches. Specifically, pathways such as fatty acid biosynthesis and propanoate metabolism are higher in effective batches while terpenoid backbone biosynthesis and bacterial chemotaxis are higher in ineffective batches.

Similar analyses are conducted for the three other therapeutic endpoints. The strict endpoint of endoscopic remission and the less strict endpoint of endoscopic response showed similar outcomes to the primary study endpoint. One notable difference is the clustering of effective batches at the higher end of α-diversity when shotgun taxonomic data is classified by endoscopic response. This higher level of α-diversity is also identified for effective batches classified by the clinical remission endpoint. In fact, classification of donor batch effectiveness based on the clinical remission endpoint showed the strongest signs of consistency with the results of the patient analysis. *Sutterella wadsworthensis*, previously associated with lack of remission in patients, is associated with ineffective batches in clinical remission. Further, pathways such as secondary bile acid biosynthesis, glycerophospholipid metabolism and biosynthesis of ansamycins are all associated with positive patient outcomes and are associated with effective batches. Moreover, heme biosynthesis is a strong marker for negative primary outcome in patients and is higher in ineffective batches.

The invention claimed is:

1. A method of manufacturing a fecal microbe preparation comprising a bacterial strain for incorporation into a pharmaceutical composition, the method comprising:
   a) selecting a source material from a human donor based on a higher relative abundance of a metabolite in the source material, wherein the metabolite is selected from the group consisting of a secondary bile acid, a short chain fatty acid (SCFA), and a combination thereof, wherein the human donor is a member of a plurality of donors, and the higher relative abundance is relative to the average relative abundance of the metabolite in source material of the plurality of donors; and
   b) harvesting the bacterial strain from the selected source material to produce the fecal microbe preparation.

2. The method of claim 1, wherein the pharmaceutical composition is formulated so as to be suitable for treating ulcerative colitis (UC).

3. The method of claim 1, wherein the metabolite is the secondary bile acid.

4. The method of claim 1, wherein a plurality of samples of source material from the human donor are selected.

5. The method of claim 1, wherein the harvesting comprises culturing the bacterial strain.

6. The method of claim 5, wherein the cultured bacterial strain is from a genus selected from the group consisting of *Eubacterium*, *Bacteroides*, *Faecalibacterium* and *Roseburia*.

7. The method of claim 6, wherein the genus is *Eubacterium* and the bacterial species is *Eubacterium* rectale.

8. The method of claim 6, wherein the genus is *Faecalibacterium* and the bacterial species is *Faecalibacterium prausnitzii*.

9. The method of claim 5, wherein the method further comprises supplementing the fecal microbe preparation with viable cultured bacteria.

10. The method of claim 9, wherein the viable cultured bacteria comprise lyophilized bacteria.

11. The method of claim 1, wherein the pharmaceutical composition comprises a capsule, and the method further comprises incorporating the fecal microbe preparation into the capsule.

12. The method of claim 1, wherein the metabolite is a SCFA.

13. The method of claim 12, wherein the SCFA is butyrate.

14. The method of claim 1, wherein the metabolite comprises both the SCFA and the secondary bile acid.

15. The method of claim 1, further comprising lyophilizing the fecal microbe preparation in the presence of a cryoprotectant.

16. The method of claim 1, further comprising spray-drying the fecal microbe preparation.

17. The method of claim 15, wherein the cryoprotectant is selected from the group consisting of polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof.

18. The method of claim 17, wherein the cryoprotectant is trehalose.

19. The method of claim 1, wherein the fecal microbe preparation comprises a community of microbes harvested from the source material.

20. The method of claim 3, wherein the secondary bile acid is selected from the group consisting of lithocholic acid, deoxycholic acid, ursodeoxycholic acid, and a combination thereof.

* * * * *